US010221447B2

(12) United States Patent
Barany

(10) Patent No.: US 10,221,447 B2
(45) Date of Patent: Mar. 5, 2019

(54) DETECTION OF DNA METHYLATION USING COMBINED NUCLEASE LIGATION REACTIONS

(71) Applicant: CORNELL UNIVERSITY, Ithaca, NY (US)

(72) Inventor: Francis Barany, New York, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 15/300,399

(22) PCT Filed: Mar. 31, 2015

(86) PCT No.: PCT/US2015/023535
§ 371 (c)(1),
(2) Date: Sep. 29, 2016

(87) PCT Pub. No.: WO2015/153571
PCT Pub. Date: Oct. 8, 2015

(65) Prior Publication Data
US 2017/0191113 A1    Jul. 6, 2017

Related U.S. Application Data

(60) Provisional application No. 61/973,496, filed on Apr. 1, 2014.

(51) Int. Cl.
*C12Q 1/68* (2018.01)
*C12Q 1/683* (2018.01)
(Continued)

(52) U.S. Cl.
CPC .................................. *C12Q 1/683* (2013.01)

(58) Field of Classification Search
None
See application file for complete search history.

(56) References Cited

U.S. PATENT DOCUMENTS 5,573,907 A    11/1996    Carrino et al.
5,854,033 A    12/1998    Lizardi
(Continued)

FOREIGN PATENT DOCUMENTS

WO    2013/123220 A1    8/2013
WO    2016/154337 A2    9/2016

OTHER PUBLICATIONS

Extended European Search Report for Corresponding EP Patent Application No. 15772834.6 (dated Jan. 25, 2018).
Zou et al., "Quantification of Methylated Markers with a Multiplex Methylation-Specific Technology," Clinical Chemistry 58(2):375-83 (2011).
(Continued)

*Primary Examiner* — Joseph G. Dauner
(74) *Attorney, Agent, or Firm* — LeClairRyan PLLC

(57) ABSTRACT

The present invention is directed to methods for identifying the presence of one or more methylated or unmethylated target nucleotide sequences in a sample that involve coupled methylation sensitive restriction enzyme digestion-ligation and/or extension processes. In some embodiments, the ligation and primary extension products formed in the reaction processes of the present invention are subsequently amplified using a polymerase chain reaction. The ligation products or primary extension products are detected, and the presence of one or more methylated or unmethylated target nucleotide sequences in the sample is identified based on the detection.

18 Claims, 36 Drawing Sheets

(51) Int. Cl.
*C12Q 1/6858* (2018.01)
*C12Q 1/6886* (2018.01)

(56) References Cited

U.S. PATENT DOCUMENTS

| | | |
|---|---|---|
| 6,270,967 B1 | 8/2001 | Whitcombe et al. |
| 7,601,821 B2 | 10/2009 | Andersen et al. |
| 2002/0137036 A1 | 9/2002 | Sorge et al. |
| 2005/0142543 A1 | 6/2005 | Barany et al. |
| 2005/0239089 A1 | 10/2005 | Johnson et al. |
| 2006/0234252 A1 | 10/2006 | Andersen |
| 2007/0092880 A1 | 4/2007 | Crothers et al. |
| 2007/0092883 A1 | 4/2007 | Schouten et al. |
| 2007/0275375 A1 | 11/2007 | Van Eijk |
| 2011/0212846 A1 | 9/2011 | Spier |
| 2012/0021949 A1* | 1/2012 | Benhattar ............ C12Q 1/6827 506/9 |
| 2012/0122088 A1 | 5/2012 | Zou et al. |

OTHER PUBLICATIONS

Zou et al., "Ultrasensitive DNA Detection by Cascade Enzymatic Signal Amplification Based on Afu Flap Endonuclease Coupled with Nicking Endonuclease," Angewandte Chemie International Edition 50 (32):7395-8 (2011).

Eijk-Van Os et al., "Multiplex Ligation-dependent Probe Amplification (MLPA®) for the Detection of Copy Number Variation in Genomic Sequences," Method Mol Biol 668:97-126 (2011).

PCT International Search Report and Written Opinion corresponding to PCT/US2015/023535, dated Oct. 29, 2015.

Dobosy et al., "RNase H-Dependent PCR (rhPCR): Improved Specificity and Single Nucleotide Polymorphism Detection Using Blocked Cleavable Primers," BMC Biotechnol. 11:80 (2011).

Lyamichev et al., "Comparison of the 5' Nuclease Activities of Taq DNA Polymerase and its Isolated Nuclease Domain," Proc. Nat. Acad. Sci. U.S.A. 96:6143-6148 (1999).

Haqqi, "Direct Ligation of PCR Products for Cloning and Sequencing," Nucleic Acids Res. 20(23):6427 (1992).

* cited by examiner

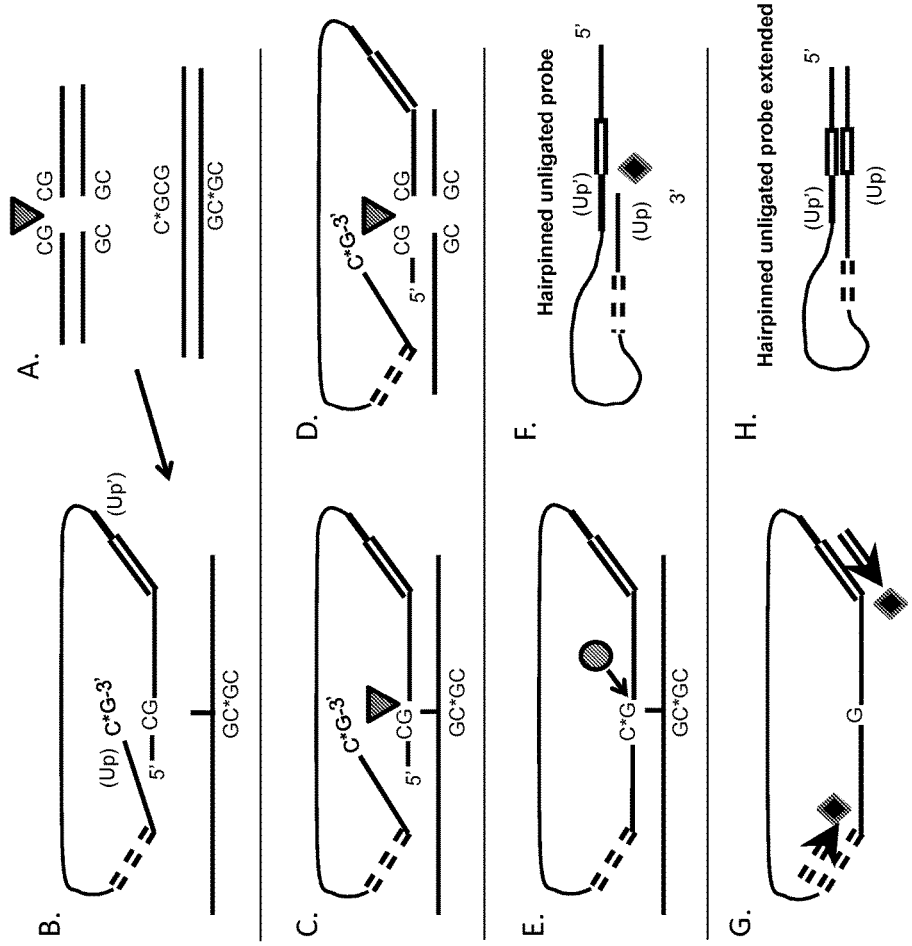

Figures 6A-6H

1. Restriction enzyme digestion-ligation reaction to detect hemi-methylation at BstUI sites. Cleave genomic DNA with BstUI (CGCG) (Fig. 6A). Coupled oligonucleotide probes hybridize to complementary target nucleic acid molecule (Fig. 6B).

2. Following probe hybridization, BstUI nicks matching 5'-end, leaving ligation-competent 5'-phospate, if template is hemi-methylated at BstUI sequence (Fig. 6C). If target was unmethylated, BstUI will cleave both probe and target (Fig. 6D).

3. Ligase covalently seals the two free ends of the coupled probes to create covalently closed ligation products. Optional use of methylated C*G on 3' end prevents recleavage with BstUI (Fig. 6E). Unligated probes form hairpins via hybridization between complementary (Up) and (Up') regions (Fig. 6F).

4. PCR amplifies only ligation products for the hemi-methylated target (Fig. 6G). Unligated hairpinned probes are extended by polymerase to occlude binding of, and subsequent extension or amplification by, the secondary primer (Fig. 6H).

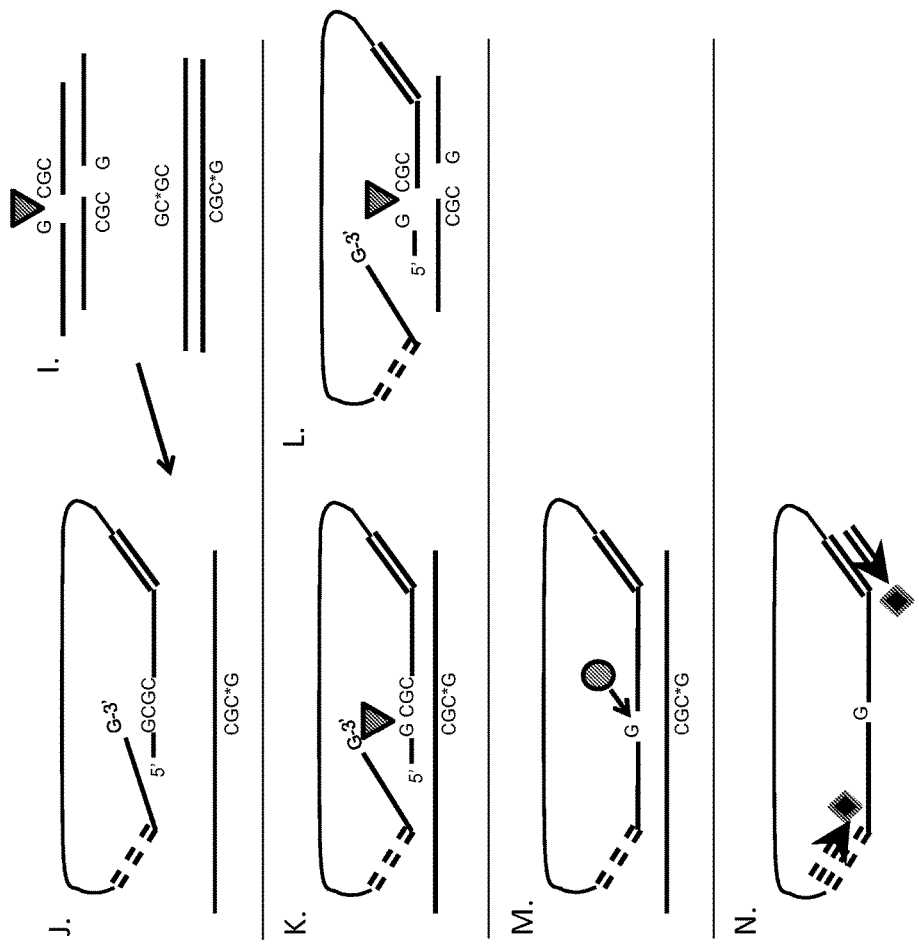

1. Restriction enzyme digestion-ligation reaction to detect methylation at HinP1I sites. Cleave genomic DNA with HinP1I (GCGC) (Fig. 8I).

2. Use coupled probe design with a G base on the 3' end of the upstream probe and with an unmethylated HinP1I sequence near the 5' end of the downstream probe (Fig. 8J).

3. Oligonucleotide hybridizes to target, with HinP1I nicking of matching 5'-end, leaving ligation-competent 5'-phospate, if template is methylated at HinP1I sequence (Fig. 8K). If target was unmethylated, HinP1I will cleave both probe and target (Fig. 8L).

4. Ligase covalently seals the two free ends of the coupled probes to create covalently closed ligation products (Fig. 8M). Prior thermal inactivation of HinP1I prevents recleavage with HinP1I. After ligation, exonuclease(s) digest all unligated primers and target DNA.

5. PCR amplifies only ligation products for the methylated target (Fig. 8N).

Figures 8I-8N

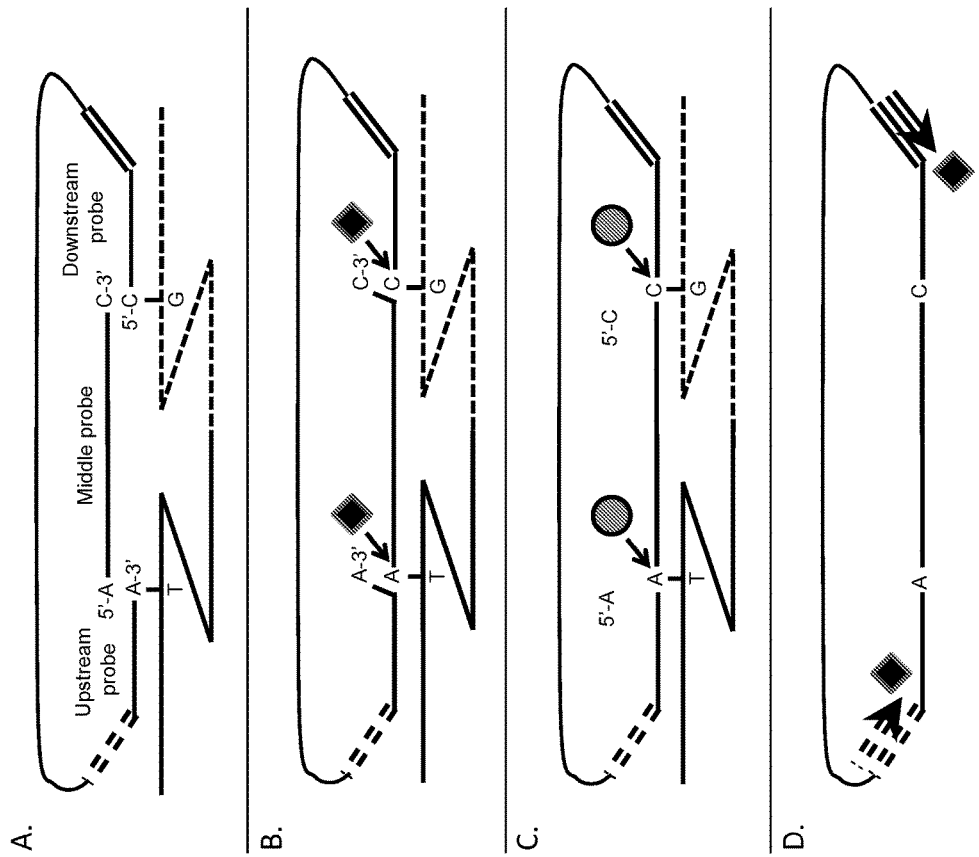

1. Nuclease-ligation reaction to detect gene translocation where precise junction position is unknown. Coupled probe contains a first probe having an upstream tag sequence and upstream gene target region, and a second probe having a downstream gene target region and complementary downstream tag sequence. Middle probe contains adjacent 5' upstream gene target and adjacent 3' downstream gene target regions (Fig. 14A).

2. 5'-nuclease activity of polymerase cleaves 5'-overlapping base of the middle and second probes when they match the 3' residue of the first and middle probes, respectively, leaving ligation-competent 5'-phospate ends on the middle and second probes (Fig. 14B).

3. Ligation covalently seals the coupled and middle probes together. After ligation, exonuclease(s) digest all unligated primers and target DNA (Fig. 14C).

4. PCR amplifies only ligation products for the gene translocation (Fig. 14D).

Figures 14A-14D

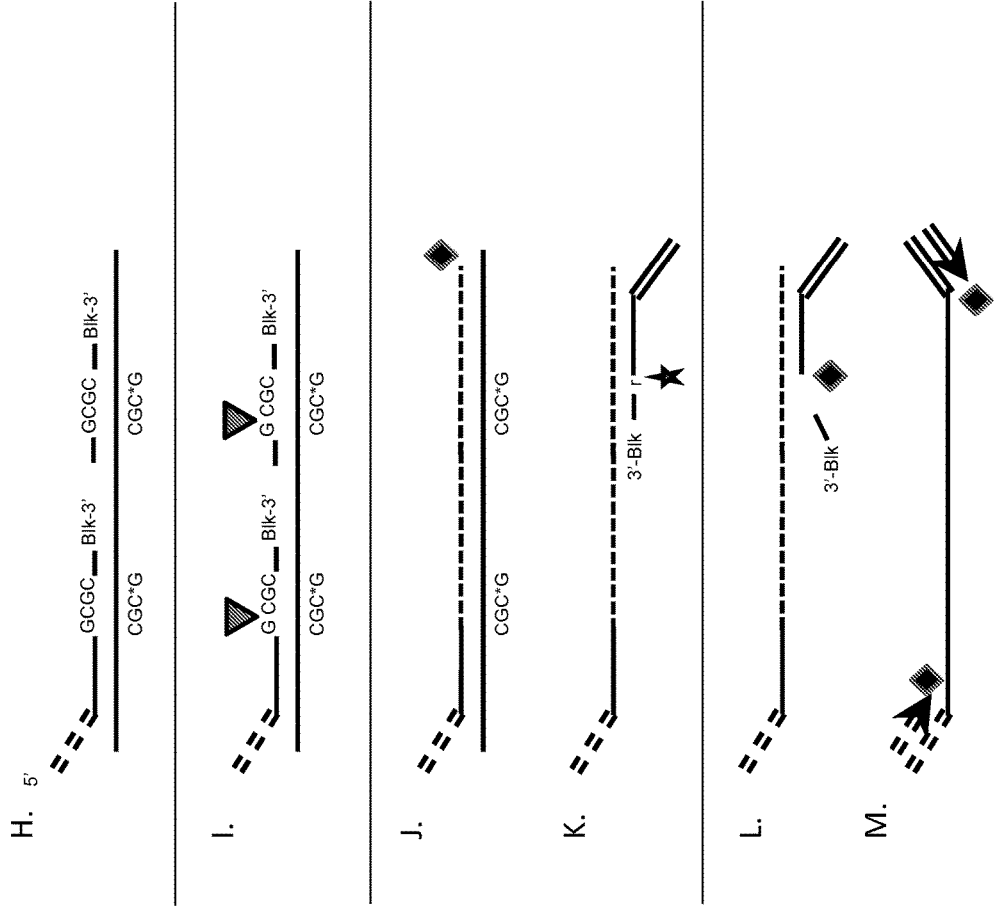

Figures 18H-18M

1. Restriction enzyme digestion-extension reaction to detect methylation at one or more HinP1I sites. Cleave genomic DNA with HinP1I (GCGC).

2. Upstream first probe contains unmethylated HinP1I sequence near the 3' end, which is blocked (Fig. 18H). Optional additional probe(s) contains unmethylated HinP1I sequence(s).

3. Oligonucleotides hybridize to target, with HinP1I nicking of one or more sites, leaving an extension competent 3' OH, provided template is methylated at one or more HinP1I sequences (Fig. 18I). If target was unmethylated, HinP1I will cleave both probe and target.

4. Polymerase extends the liberated 3' end. Prior thermal inactivation of HinP1I, or polymerase incorporation of modified nucleotides prevents recleavage with HinP1I (Fig. 18J).

5. Downstream blocked primer hybridizes to extension product. RNaseH cleaves ribo-base liberating 3' OH (Fig. 18K).

6. Polymerase extends liberated 3' end of downstream primer, allows for formation of extension product with secondary binding sites on both ends (Fig. 18L). PCR amplifies only extension products for the methylated target (Fig. 18M).

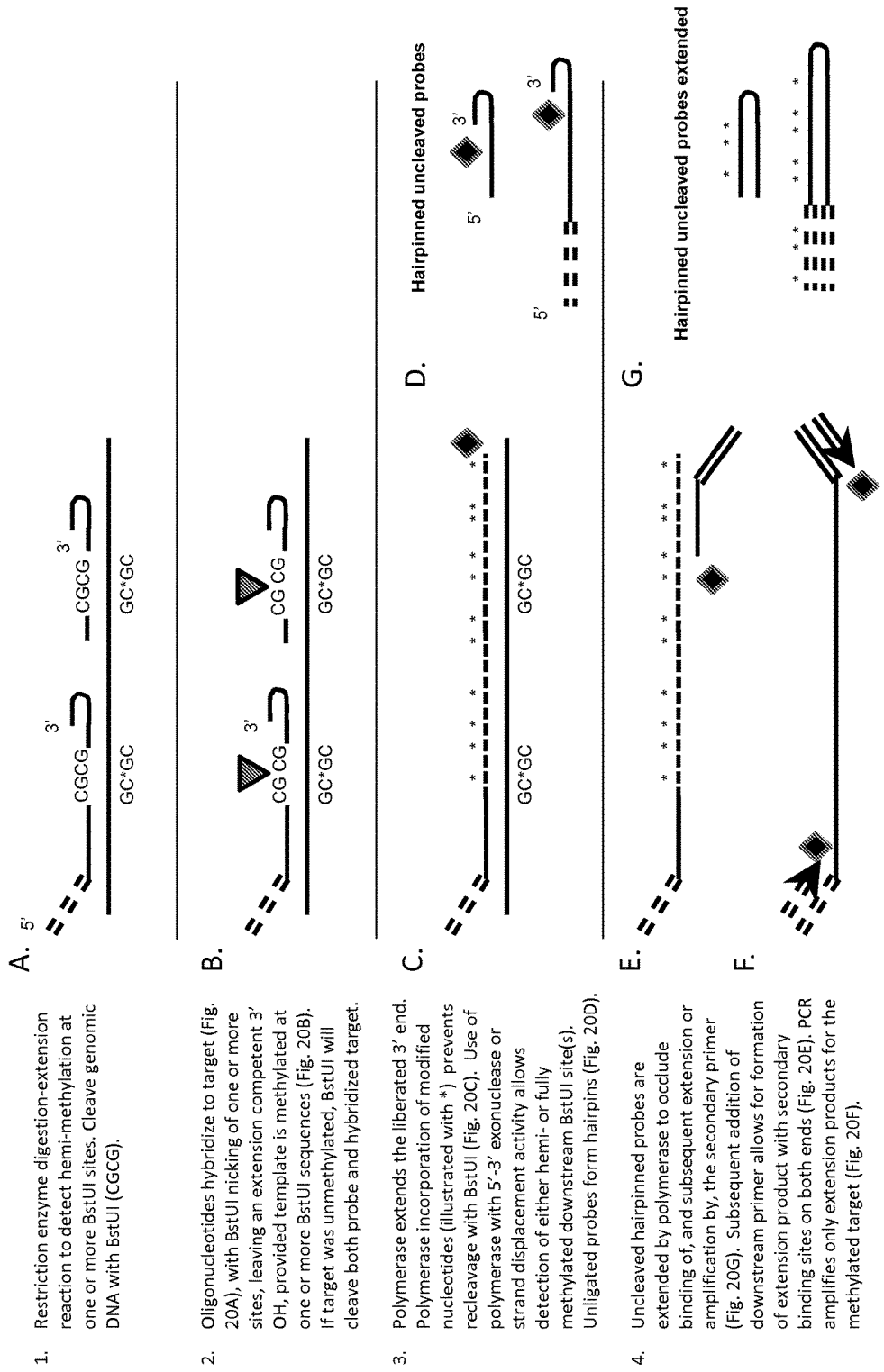

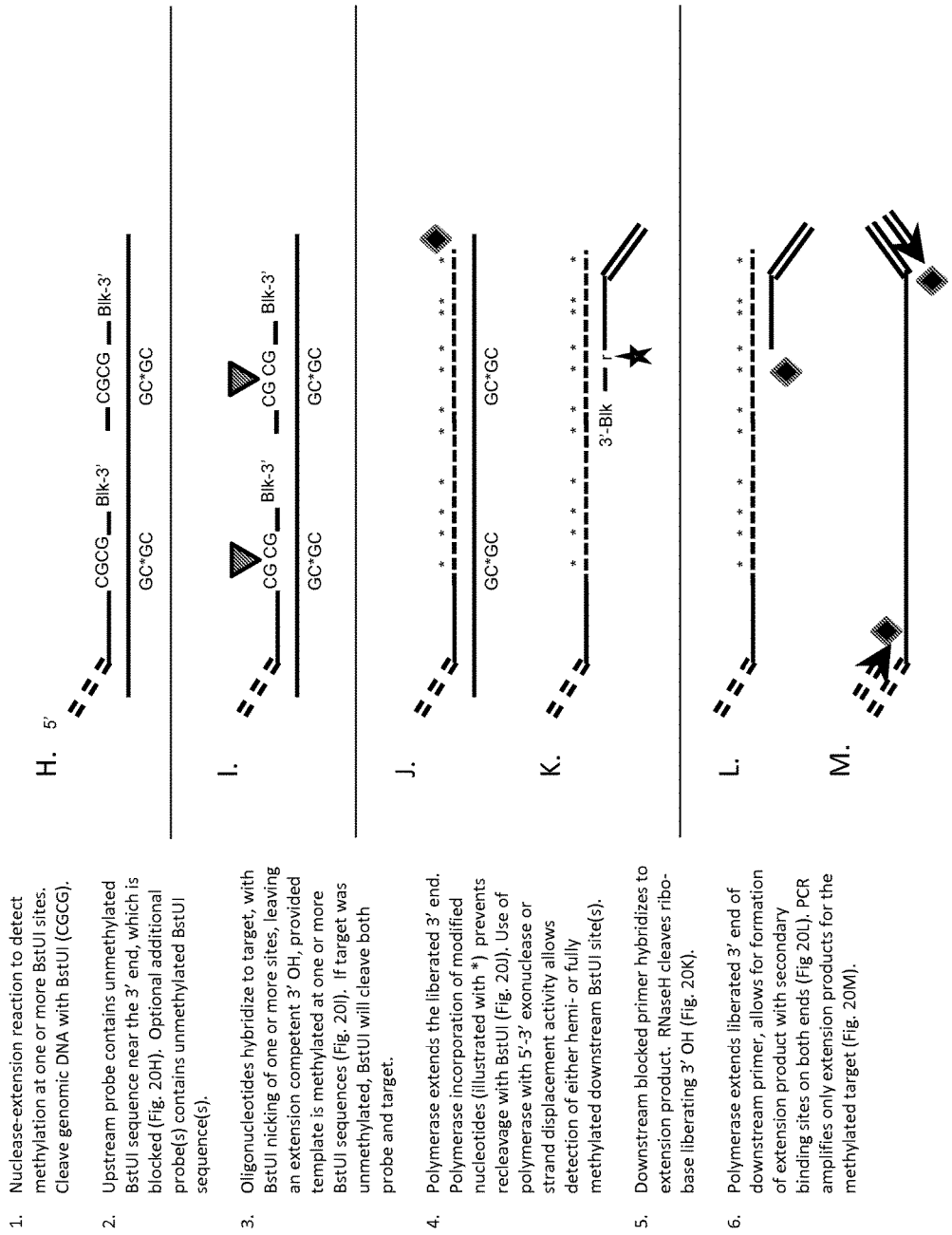

Figures 20H-20M

1. Nuclease-extension reaction to detect methylation at one or more BstUI sites. Cleave genomic DNA with BstUI (CGCG).

2. Upstream probe contains unmethylated BstUI sequence near the 3' end, which is blocked (Fig. 20H). Optional additional probe(s) contains unmethylated BstUI sequence(s).

3. Oligonucleotides hybridize to target, with BstUI nicking of one or more sites, leaving an extension competent 3' OH, provided template is methylated at one or more BstUI sequences (Fig. 20I). If target was unmethylated, BstUI will cleave both probe and target.

4. Polymerase extends the liberated 3' end. Polymerase incorporation of modified nucleotides (illustrated with *) prevents recleavage with BstUI (Fig. 20J). Use of polymerase with 5'-3' exonuclease or strand displacement activity allows detection of either hemi- or fully methylated downstream BstUI site(s).

5. Downstream blocked primer hybridizes to extension product. RNaseH cleaves ribobase liberating 3' OH (Fig. 20K).

6. Polymerase extends liberated 3' end of downstream primer, allows for formation of extension product with secondary binding sites on both ends (Fig 20L). PCR amplifies only extension products for the methylated target (Fig. 20M).

DETECTION OF DNA METHYLATION USING COMBINED NUCLEASE LIGATION REACTIONS

This application is a national stage application under 35 U.S.C. § 371 of PCT Application No. PCT/US2015/023535, filed Mar. 31, 2015, which claims priority benefit of U.S. Provisional Patent Application Ser. No. 61/973,496, filed Apr. 1, 2014, which are hereby incorporated by reference in their entirety.

FIELD OF THE INVENTION

The present invention relates to a method for relative quantification of changes in DNA methylation using combined nuclease, ligation, and polymerase reactions.

BACKGROUND OF THE INVENTION

Cancers contain altered methylation patterns that result in aberrant expression of critical genes. Hypermethylation turns off expression of genes required to regulate normal growth while hypomethylation allows for inappropriate expression of genes that allow cells to proliferate. Promoters for genes often have regions of high CpG content known as "CpG Islands". When genes, such as tumor suppressor genes, with promoter CpG islands are turned off, this is usually accompanied with methylation of most CpG sequences within the promoter and 1st intron regions. Aberrant promoter hypermethylation occurs at the 5-position of cytosine within the CpG dinucleotide (Gardiner-Garden et al., *J. Mol. Biol.*, 196(2): 261-82 (1987)). It inactivates the expression of critical genes that are involved in tumor suppression, DNA repair, control of tumor metastasis, and invasion (Cheng et al., Genome Res. 16(2): 282-89 (2005), Feinberg et al., *Nature*, 301: 89-92 (1983); Jones et al., *Nat. Rev. Genet.*, 3(6): 415-28 (2002)). There is a great need in both basic and clinical research to identify promoter DNA methylation status with high efficiency and accuracy for disease diagnoses and prognoses.

The presence and absence of methylation in certain genetic regions has prenatal diagnostic and prognostic applications. For example, aberrant methylation on regions on chromosomes 13, 18, 21, X, and Y can be used to diagnose Down syndrome (Patsalis et al., *Exp. Opin. Biol. Ther.* 12 (Suppl. 1): S155-S161 (2012). Because fetal DNA and maternal DNA are differentially methylated, cell-free DNA in maternal plasma can provide a source of fetal DNA, which can be obtained non-invasively and utilized to assess the methylation state of the aforementioned chromosomes.

Currently, a number of groups have used bisulfite approaches to detect the presence of low levels of methylated DNA in serum, as a marker of early cancer (deVos, *Clinical Chemistry* 55(7):1337-1346 (2009), Lind et al., *Molecular Cancer* 10:85 (2011)). However, often a single marker gives unacceptably high false-positive and false-negative results (Alquist et al., *Clin. Gastroenterol. Hepatol.* 10(3): 272-277 (2012)). Thus, a single or a few methylation markers is insufficient for robust detection of early cancer from the serum. There is an urgent need for methods with multiplexed detection of very low levels of methylated DNA when the majority of DNA with the same sequence is unmethylated. For example, detection of multiple methylated DNA sequences in cell-free DNA isolated from serum may enable early detection of cancer. Likewise, methods for multiplexed detection of very low levels of unmethylated DNA when the majority of DNA with the same sequence is methylated are also urgently needed for applications such as early detection of cancer.

Various methods have been developed for the study of promoter DNA methylation status of known genes (Laird P. W., *Nature Review Cancer*, 3: 253-266 (2003)). These methods can generally be grouped into two categories: methylation-sensitive restriction endonuclease assays and sodium bisulfite conversion based approaches.

Methylation-Sensitive Restriction Endonuclease Digestion Methods:

This approach takes advantage of methyl-sensitive restriction enzymes, wherein genomic DNA is cleaved when unmethylated, and this is followed by a PCR amplification using primers that flank the site(s) (Singer-Sam et al., *Nucleic Acids Res.*, 18(3): 687 (1990), Singer-Sam et al., *Mol. Cell. Biol.*, 10(9): 4987-9 (1990)). A methylated restriction endonuclease site results in the presence of the proper PCR product. The credibility of this method depends on the complete digestion of unmethylated DNA by the restriction endonuclease. This problem is exacerbated by: (i) limiting amounts of methylated DNA in the sample, (ii) the requirement of some restriction enzymes to bind two unmethylated sites simultaneously, and (iii) the lack of, or poor activity of restriction enzymes to single-stranded DNA that may arise during sample preparation. It is difficult to drive endonuclease digestions to completion. Thus, it is sometimes difficult to determine whether PCR amplicons result from incomplete digestion (i.e. false positives) or from those of low abundance methylation sites (i.e. true positives). Restriction enzyme techniques are based on removing the unmethylated DNA, and assuming that PCR amplification of the remaining DNA arises because it was methylated, and consequently the method is susceptible to false positives arising from incomplete removal of unmethylated DNA. This technique has the disadvantage that it is not accurate for finding low levels of methylated DNA when the majority of the same sequence is unmethylated, as would be the case with detection of cancer-associated methylation at multiple markers in cell free DNA from the serum.

Sodium-Bisulfite-Based Chemical Conversion.

Chemical conversion of cytosines to uracils using bisulfite can be used to detect DNA methylation differences. 5-methylcytosines are resistant to conversion, and deamination only occurs on unmethylated cytosines (Frommer et al., *Proc. Natl. Acad. Sci. USA*, 89(5): 1827-31 (1992)). Bisulfite can be quantitatively added to the 5-6 double bonds of cytosine if there is no methyl group on the 5 position. Bisulfite addition renders the cytosine susceptible to hydrolytic deamination; subsequent elimination of the bisulfite results in the formation of uracil (Voss et al., *Anal. Chem.*, 70(18): 3818-3823 (1998)). One strand of the modified DNA sequences can then be PCR amplified and sequenced. However, due to stromal cell contamination in a typical clinical sample, direct sequencing without cloning the PCR products reduces the sensitivity of the technique. It requires about 25% of the alleles to be methylated for accurate detection (Myohanen et al., *DNA Sequence*, 5: 1-8 (1994).

Development of methylation-specific PCR (MSP) has allowed the sensitive and specific study of low abundance methylation sequences (Herman et al., *Proc. Natl. Acad. Sci. USA*, 93(18): 9821-6 (1996)). MSP relies upon chemical modification of DNA using bisulfite, and specifically designed PCR primers that are complementary to the bisulfite modified DNA template. Typically, more than three CpG sites have to be included in the oligonucleotide sequences. Two sets of MSP PCR primers are designed, one set of the MSP primers has the sequence to perfectly hybridize to the complementary strand of the bisulfite-treated methylated DNA sequence with methyl-cytosines residing on the CpG sites. The other set of the MSP primers is only designed to perfectly hybridize to the complementary strand of the bisulfite-treated DNA sequence in the absence of methylated cytosine. Consequently, the MSP specific PCR products only results from the DNA template which contains methyl-cytosines.

There are three major difficulties with this approach. The design of MSP primers requires sufficient numbers of methylated cytosines to be present in the primer sequence to ensure the selection capability. It may not be sufficiently sensitive to distinguish partial methylated sequences from fully methylated one. In addition, this assay analyzes one gene at a time, and both sets of MSP primers have different annealing temperatures which may further slowdown its throughput. Finally, bisulfite treatment of DNA often nicks the DNA (i.e. destroys the backbone chain) as it is also converting unmethylated cytosines to uracil. Conditions which assure that all unmethylated cytosines are converted to uracil may also destroy the DNA. Conditions which assure that sufficient DNA remains intact may not assure that all unmethylated cytosines are converted to uracil. Thus, absence of a band may be the consequence of destroying too much of the starting DNA and, consequently, insufficient amplification, leading to a false negative result. Likewise, presence of a band may be the consequence of incomplete conversion of unmethylated cytosine to uracil, allowing for primer binding at an unmethylated site, and leading to a false positive result. Some of these problems may be overcome by combining the use of Bisulfite treatment, the polymerase chain reaction, and the ligase detection reaction (see U.S. Pat. No. 7,358,048 to Barany et al.)

A further improvement of this technique employs a blocking oligonucleotide that hybridizes to the sequence for bisulfite-converted unmethylated DNA, thus enriching for amplification of bisulfite-converted methylated DNA (deVos et al., *Clinical Chemistry* 55(7):1337-1346 (2009)). The disadvantage is that bisulfite treatment destroys from 50% to 90% of the original DNA integrity by nicking it. When starting with DNA from the serum (with average length of about 160 bases), this can be a significant problem. Further, converting C's to U's reduces the complexity of the sequence from 4 bases to 3 bases. Thus, non-specific amplifications can occur. This usually necessitates a nested-PCR approach; this runs the risk of carryover contamination and is generally not ideal for multiplexed amplifications.

The present invention is directed at overcoming this and other deficiencies in the art.

SUMMARY OF THE INVENTION

A first aspect of the present invention is directed to a method for identifying, in a sample, one or more target nucleic acid molecules differing from other nucleic acid molecules in the sample by one or more methylated residues. This method involves providing a sample containing one or more target nucleic acid molecules potentially containing one or more methylated residues within at least one methylation sensitive restriction enzyme recognition sequence. One or more oligonucleotide probe sets are provided, each probe set comprising (a) a first oligonucleotide probe having a target-specific portion, and (b) a second oligonucleotide probe having a target specific portion. The first and second oligonucleotide probes of a probe set are configured to hybridize adjacent to one another on the target nucleotide sequence with a junction between the first and second oligonucleotide probes, and, in a probe set, the target specific portion of the second oligonucleotide probe has an overlapping identical nucleotide at the junction with the first oligonucleotide probe. The method further involves contacting the sample and the one or more oligonucleotide probe sets under conditions effective for first and second oligonucleotide probes of a probe set to hybridize at adjacent positions in a base specific manner to their corresponding target nucleic acid molecule, if present in the sample, wherein upon hybridization the overlapping identical nucleotide of the second oligonucleotide probe forms a flap at the junction comprising the overlapping identical nucleotide. The overlapping identical nucleotide of the second oligonucleotide probe is cleaved with an enzyme having 5' nuclease activity, thereby liberating a 5' phosphate on the second oligonucleotide probe. The first and second oligonucleotide probes of the one or more oligonucleotide probe sets are ligated together at the junction to form a ligation product hybridized to its complementary target nucleic acid molecule, wherein the ligation product and its hybridized target nucleic acid molecule comprise at least one methylation sensitive restriction enzyme recognition sequence. The method further involves blending at least one methylation sensitive restriction enzyme with the hybridized ligation products to form a methylation sensitive restriction enzyme reaction mixture, and subjecting the methylation sensitive restriction enzyme reaction mixture to conditions suitable for cleavage of the ligation product and its hybridized target nucleic acid molecule if the target nucleic acid molecule does not contain one or more methylated residues within the at least one methylation sensitive restriction enzyme recognition sequence. The cleavage will not occur if the target nucleic acid molecule contains one or more methylated residues within the at least one methylation sensitive restriction enzyme recognition sequence. Uncleaved ligation products in the sample are detected and distinguished, and the presence of one or more target nucleic acid molecules differing from other nucleic acid molecules in the sample by one or more methylated residues is identified based on the detecting.

A second aspect of the present invention is directed to a method for identifying, in a sample, one or more target nucleic acid molecules differing from other nucleic acid molecules in the sample by one or more methylated residues. This method involves providing a sample containing one or more target nucleic acid molecules potentially containing one or more methylated residues within one or more methylation sensitive restriction enzyme recognition sequences, and providing one or more oligonucleotide probe sets, each probe set comprising (a) a first oligonucleotide probe having a target-specific portion, and (b) a second oligonucleotide probe having a target specific portion containing at least one methylation sensitive restriction enzyme recognition sequence. The first and second oligonucleotide probes of a probe set are configured to hybridize on the target nucleic acid molecule. The sample and the one or more oligonucleotide probe sets are contacted under conditions effective for first and second oligonucleotide probes of a probe set to hybridize in a base specific manner to their corresponding target nucleic acid molecule, if present in the sample, to form hybridization products. The method further involves blending at least one methylation sensitive restriction enzyme with the hybridization products, if present in the sample, to form a methylation sensitive restriction enzyme reaction mixture. The methylation sensitive restriction enzyme reaction mixture is subjected to conditions suitable for the methylation sensitive restriction enzyme to cleave the second oligonucleotide probe of a hybridization product at its methylation sensitive restriction enzyme recognition sequence if the target nucleic acid molecule of the hybridization product contains one or more methylated residues within the methylation sensitive restriction enzyme recognition sequence, said cleavage liberating a 5' phosphate on the second oligonucleotide probe. The first and second oligonucleotide probes of the one or more oligonucleotide probe sets are ligated together to form ligation products. The method further involves detecting and distinguishing the ligation products in the sample, and identifying the presence of one or more target nucleic acid molecules differing from other nucleic acid molecules in the sample by one or more methylated residues based on said detecting.

A third aspect of the present invention is directed to a method for identifying, in a sample, one or more target nucleic acid molecules differing from other nucleic acid molecules in the sample by one or more methylated residues. This method involves providing a sample containing one or more target nucleic acid molecules potentially containing one or more methylated residues within one or more methylation sensitive restriction enzyme recognition sequences. One or more oligonucleotide probe sets are provided, each probe set comprising at least a first oligonucleotide probe comprising a target-specific portion configured to hybridize on the target nucleic acid molecule and containing (i) at least one methylation sensitive restriction enzyme recognition sequence, (ii) a 3' blocking group, hairpin, or flap region, and (iii) a 5' primer-specific portion. The sample is contacted with the one or more oligonucleotide probe sets under conditions effective for the at least first oligonucleotide probe of a probe set to hybridize in a base specific manner to a corresponding target nucleic acid molecule, if present in the sample, to form hybridization products. The method further involves blending at least one methylation sensitive restriction enzyme with the hybridization products to form a methylation sensitive restriction enzyme reaction mixture, and subjecting the methylation sensitive restriction enzyme reaction mixture to conditions suitable to cleave the at least first oligonucleotide probe of a hybridization product where the target nucleic acid molecule of said hybridization product contains one or more methylated residues within a methylation sensitive restriction enzyme recognition sequence. The cleavage liberates a 3'-OH on the at least first oligonucleotide probe of the hybridization product. The method further involves extending the liberated 3'OH of the cleaved at least first oligonucleotide probe of the hybridization product using a polymerase to form a hybridized extension product. One or more primary oligonucleotide primer sets are provided, each primer set comprising (i) a first primary oligonucleotide primer comprising a nucleotide sequence that is the same as a region of the target nucleic acid molecule sequence, wherein said region is 5' of the one or more methylation sensitive restriction enzyme recognition sequences of the target nucleic acid molecule, and a secondary primer-specific portion, and, optionally, (ii) a second primary oligonucleotide primer comprising a nucleotide sequence that is the same as the 5' primer-specific portion of the at least first oligonucleotide probe in a probe set. The method further involves blending the hybridized extension products, the one or more primary oligonucleotide primer sets, and a polymerase to form a polymerase chain reaction mixture, and subjecting the polymerase chain reaction mixture to one or more polymerase chain reaction cycles comprising a denaturation treatment, a hybridization treatment, and an extension treatment thereby forming primary extension products. The primary extension products are detected and distinguished, thereby identifying the presence of one or more target nucleic acid molecules differing from other nucleic acid molecules in the sample by one or more methylated residues.

The above-described methods for detecting methylated residues in target nucleic acid molecule have multiple levels of discrimination allowing for the highest levels of sensitivity and specificity, even when trying to detect low-abundance methylated target nucleic acid molecules.

In accordance with the first aspect of the present invention, the levels of discrimination include (i) use of methylation sensitive restriction enzymes to cleave double-stranded target when not methylated, (ii) use of 5'-3' nuclease activity of polymerase or Fen nuclease on downstream second probe, (iii) use of 3' ligation fidelity of thermostable ligase on upstream first probe, (iv) reuse of methylation sensitive restriction enzymes to cleave double-stranded target when original genomic DNA was not methylated, (v) use of sequences on the 5' end of downstream probes, such that when they are not cleaved, form hairpins at lower temperature and extend on themselves to form products that do not amplify.

In accordance with one embodiment of second aspect of the present invention, the levels of discrimination for detection of hemi-methylated target nucleic acid molecules include (i) use of methylation sensitive restriction enzymes to cleave double-stranded target when not methylated, (ii) use of methylation sensitive BstUI restriction enzymes to nick double-stranded target on downstream second probe when original genomic DNA was hemi-methylated, (iii) use of 3' ligation fidelity of thermostable ligase on upstream first probe, (iv) reuse of methylation sensitive restriction enzymes to cleave double-stranded target when original genomic DNA was not methylated, and (v) use of sequences on the 5' end of downstream second probe, such that when they are not cleaved, form hairpins at lower temperature and extend on themselves to form products that do not amplify.

In accordance with another embodiment of the second aspect of the present invention, the levels of discrimination for detection of methylated target nucleic acid molecules include (i) use of methylation sensitive restriction enzymes to cleave double-stranded target when not methylated, (ii) use of methylation sensitive HinP1I restriction enzymes to nick double-stranded target on both upstream first and downstream second probes when original genomic DNA was methylated, (iii) use of 3' ligation fidelity of thermostable ligase on upstream first probe, (iv) reuse of methylation sensitive restriction enzymes to cleave double-stranded target when original genomic DNA was not methylated, (v) use of sequences on the 3' end of upstream first probe and the 5' end of downstream second probe, such that when they are not cleaved, form hairpins at lower temperature and extend on themselves to form products that do not amplify.

In accordance with the third aspect of the present invention, the levels of discrimination for detection of low-abundance methylation include (i) use of methylation sensitive restriction enzymes to cleave double-stranded target when not methylated, (ii) use of methylation sensitive restriction enzymes to nick double-stranded target on both upstream first and downstream second probe when original genomic DNA was methylated, (iii) use of 3' extension activity of polymerase, (iv) reuse of methylation sensitive HinP1I restriction enzymes to cleave double-stranded target when original genomic DNA was not methylated, (v) use of sequences on the 3' end of upstream first and downstream second probes, such that when they are not cleaved, form hairpins at lower temperature and extend on themselves to form products that do not amplify.

BRIEF DESCRIPTION OF THE DRAWINGS

FIGS. 3A-3P show the FEN-ligation-methylation sensitive restriction enzyme digestion reaction process of the present invention using a coupled probe design to detect methylation of target nucleic acid molecules at BstU1 methylation sites (i.e., C*GC*G sites). FIGS. 3A-3I show one variation of this process where the coupled probes are designed to form hairpins in the absence of ligation to prevent target independent amplification and false positive signal generation. FIGS. 3J-3P show an alternative variation of this process where unligated coupled probes are removed from the reaction process by exonuclease digestion to prevent target independent amplification and false positive signal generation. Restriction endonuclease is shown as a triangle; ligase is shown as a circle; and polymerase as a diamond.

FIGS. 6A-6N show the methylation sensitive restriction enzyme digestion-ligation reaction process of the present invention using a coupled probe design to detect hemi-methylation at BstU1 methylation sites in a target nucleic acid molecule. FIGS. 6A-6H show one variation of this process where coupled probes are designed to form hairpins in the absence of ligation to prevent target independent amplification and false positive signal generation. FIGS. 6I-6N show an alternative variation of this process where unligated coupled probes are removed from the reaction process by exonuclease digestion to prevent target independent amplification and false positive signal generation. Restriction endonuclease is shown as a triangle; ligase is shown as a circle; and polymerase as a diamond.

FIGS. 8A-8N show the methylation sensitive restriction enzyme digestion-ligation reaction process of the present invention using a coupled probe design to detect methylation at HinP1I methylation sites in a target nucleic acid molecule. FIGS. 8A-8H show one variation of this process where coupled probes are designed to form hairpins in the absence of ligation to prevent target independent amplification and false positive signal generation. FIGS. 8I-8N show an alternative variation of this process where unligated coupled probes are removed from the reaction process by exonuclease digestion to prevent target independent amplification and false positive signal generation. Restriction endonuclease is shown as a triangle; ligase is shown as a circle; and polymerase as a diamond.

FIGS. 9A-9F show one variation of this process where the first oligonucleotide probe contains a hairpin at its 3' end. In the absence of HinP1I digestion, the 3' hairpin will extend back on itself. FIGS. 9G-9L show an alternative variation of this process where the first oligonucleotide probe contains a blocking group at its 3' end. Restriction endonuclease is shown as a triangle; ligase is shown as a circle; and polymerase as a diamond.

FIGS. 10A-10F show one variation of this process where coupled probes are designed to form hairpins in the absence of ligation to prevent target independent amplification and false positive signal generation. FIGS. 10G-10J show an alternative variation of this process where unligated coupled probes are removed from the reaction process by exonuclease digestion to prevent target independent amplification and false positive signal generation. Restriction endonuclease is shown as a triangle; ligase is shown as a circle; and polymerase as a diamond.

FIGS. 14A-14D show a variation of the nuclease digestion-ligation reaction process of the present invention depicted in FIG. 13 to detect gene translocations in a target nucleic acid molecule where the precise junction position is unknown. In this embodiment, the upstream first and downstream second oligonucleotide probes are coupled together and utilized in conjunction with a middle probe. As described in reference to FIG. 13, the first and middle probes have ligation competent 3'OH ends that are overlapped by the immediately flanking 5'OH ends of the middle and second probes, respectively. In the absence of nuclease cleavage and ligation, unligated probes are subject to exonuclease digestion to prevent target independent amplification and false positive signal generation. Ligase is shown as a circle; polymerase as a diamond.

FIGS. 18A-18M show the methylation sensitive restriction enzyme digestion-extension reaction process of the present invention to detect methylation at adjacent HinP1I methylation sites in a target nucleic acid molecule. FIGS. 18A-18G show one variation of this process where the first and optional additional oligonucleotide probes contain a hairpin at their 3' ends. In the absence of HinP1I digestion, the 3' hairpins will extend back on themselves. FIGS. 18H-18M show an alternative variation of this process where the first and second oligonucleotide probes contain a blocking group at their 3' end. FIG. 18K also shows a variation of the process involving the use of a downstream primer containing a cleavable blocking group on its 3' end to enhance target-specific amplification. Restriction endonuclease is shown as a triangle; polymerase as a diamond; and enzyme capable of cleaving 3' blocking group on primer is shown as a star.

FIGS. 20A-20M show the methylation sensitive restriction enzyme digestion-extension reaction process of the present invention to detect methylation at adjacent BstU1 methylation sites in a target nucleic acid molecule. FIGS. 20A-20G show one variation of this process where the first and optional additional oligonucleotide probes contain a hairpin at their 3' ends. In the absence of BstU1 digestion, the 3' hairpins extend back on themselves. FIGS. 20H-20M show an alternative variation of this process where the first and second oligonucleotide probes contain a blocking group at their 3' end. FIG. 20K also shows a variation of the process involving the use of a downstream primer containing a cleavable blocking group on its 3' end to enhance target-specific amplification. Restriction endonuclease is shown as a triangle; polymerase as a diamond; and enzyme capable of cleaving 3' blocking group on primer is shown as a star.

In FIG. 22A the second oligonucleotide probe has a 3' tail $C_1$ that is complementary to the $C_1'$ 5' tail on the first oligonucleotide probe, and in FIG. 22B, the second oligonucleotide probe has a 3' tail $A_1$' that is complementary to the $A_1$ 5' tail on the first oligonucleotide probe. In both cases, the correct ligation products form a hairpin at the temperature used for exonuclease I treatment. Single-strand-specific 3' exonuclease cleaves single-stranded unligated oligonucleotides, but not ligated products that form hairpins. In FIG. 22C, the first and second oligonucleotide probes bear target-specific complementary tags, $C_1$ and $C_1$', and additionally, the second oligonucleotide probe has a universal tag $L_1$. After ligation, a hairpin forms upon hybridization of $C_1$ and $C_1$'. A universal biotinylated oligonucleotide ($L_1$') is ligated to the hairpinned product in the same reaction permitting streptavidin selection for biotin-bearing ligation products.

FIG. 23A is a schematic showing the restriction enzyme digestion-ligation-PCR process of the present invention. Ligation products or extension products formed during this process contain 3' and 5' primer specific portions (U1 and U2), a zipcode portion (Z1) and the target specific portions. FIG. 23B shows detection of the ligation product or an extension product thereof using the zipcode in a traditional Taqman® (Roche Molecular Systems, Pleasanton, Calif.) type assay where a capture oligonucleotide complementary to the zipcode portion serves as the Taqman® probe. FIG. 23C shows zipcode mediated capture of extension products on a universal array containing complementary capture oligonucleotides.

DETAILED DESCRIPTION OF THE INVENTION

Figures 1A, 1B, 1C, 1D:
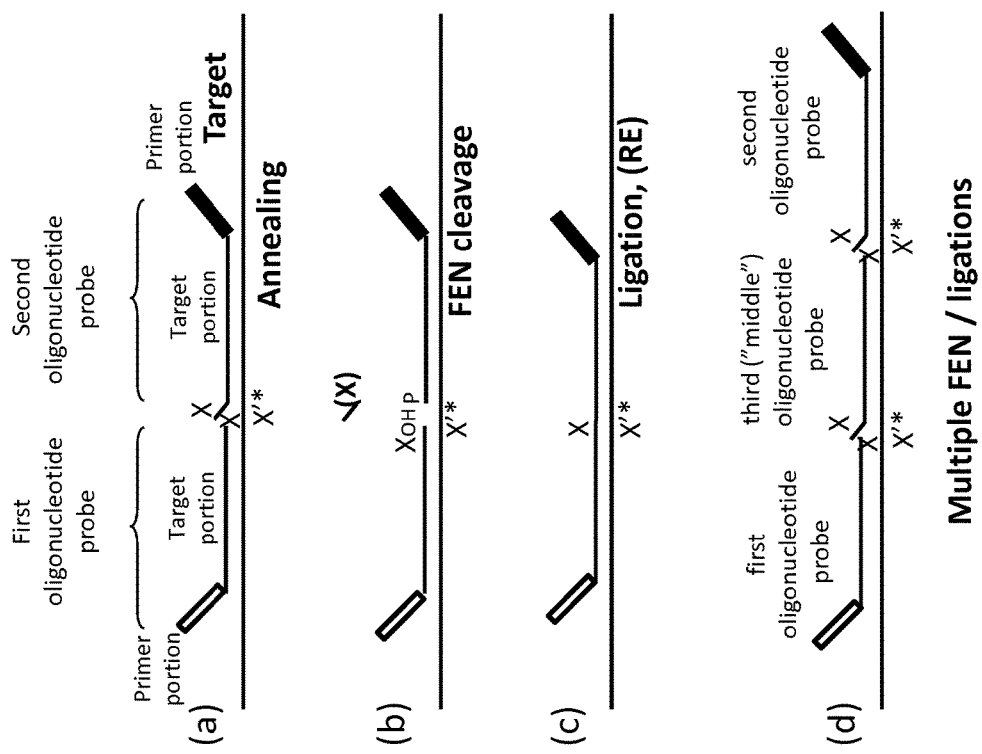
FIGS. 1A-1D depict the general process of identifying one or more methylated residues within a methylation sensitive restriction enzyme recognition sequence of a target nucleic acid molecule using the 5'-nuclease (FEN)-ligation-methylation sensitive restriction enzyme digestion process of the present invention.

A first aspect of the present invention is directed to a method for identifying, in a sample, one or more target nucleic acid molecules differing from other nucleic acid molecules in the sample by one or more methylated residues. This method involves providing a sample containing one or more target nucleic acid molecules potentially containing one or more methylated residues within at least one methylation sensitive restriction enzyme recognition sequence. One or more oligonucleotide probe sets are provided, each probe set comprising (a) a first oligonucleotide probe having a target-specific portion, and (b) a second oligonucleotide probe having a target specific portion. The first and second oligonucleotide probes of a probe set are configured to hybridize adjacent to one another on the target nucleotide sequence with a junction between the first and second oligonucleotide probes, and, in a probe set, the target specific portion of the second oligonucleotide probe has an overlapping identical nucleotide at the junction with the first oligonucleotide probe. The method further involves contacting the sample and the one or more oligonucleotide probe sets under conditions effective for first and second oligonucleotide probes of a probe set to hybridize at adjacent positions in a base specific manner to their corresponding target nucleic acid molecule, if present in the sample, wherein upon hybridization the overlapping identical nucleotide of the second oligonucleotide probe forms a flap at the junction comprising the overlapping identical nucleotide. The overlapping identical nucleotide of the second oligonucleotide probe is cleaved with an enzyme having 5' nuclease activity, thereby liberating a 5' phosphate on the second oligonucleotide probe. The first and second oligonucleotide probes of the one or more oligonucleotide probe sets are ligated together at the junction to form a ligation product hybridized to its complementary target nucleic acid molecule, wherein the ligation product and its hybridized target nucleic acid molecule comprise at least one methylation sensitive restriction enzyme recognition sequence. The method further involves blending at least one methylation sensitive restriction enzyme with the hybridized ligation products to form a methylation sensitive restriction enzyme reaction mixture, and subjecting the methylation sensitive restriction enzyme reaction mixture to conditions suitable for cleavage of the ligation product and its hybridized target nucleic acid molecule if the target nucleic acid molecule does not contain one or more methylated residues within the at least one methylation sensitive restriction enzyme recognition sequence. The cleavage will not occur if the target nucleic acid molecule contains one or more methylated residues within the at least one methylation sensitive restriction enzyme recognition sequence. Uncleaved ligation products in the sample are detected and distinguished, and the presence of one or more target nucleic acid molecules differing from other nucleic acid molecules in the sample by one or more methylated residues is identified based on the detecting.

FIGS. 1A-1D depict the general process of identifying one or more methylated residues within a methylation sensitive restriction enzyme recognition sequence of a target nucleic acid molecule using the coupled nuclease-ligase-methylation sensitive restriction enzyme digestion reaction process of the present invention. The reaction utilizes a plurality of probe sets, each probe set consisting of at least a first and a second oligonucleotide probe. Each oligonucleotide probe has a target-specific portion that is complementary to a region of a target nucleic acid molecule sequence (FIG. 1A). The first oligonucleotide probe bears a ligation competent 3' OH end while the second oligonucleotide probe bears a ligation incompetent 5' end (i.e., an oligonucleotide probe without a 5' phosphate). In accordance with this aspect of the present invention, the oligonucleotide probes of a probe set are designed such that the 3'-most base of the first oligonucleotide probe is overlapped by the immediately flanking 5'-most base of the second oligonucleotide probe that is complementary to the target nucleic acid molecule. The overlapping nucleotide is referred to as a "flap". As shown in FIG. 1B, when the overlapping flap nucleotide of the second oligonucleotide probe (depicted as "X") is complementary to the target nucleic acid molecule sequence ("X") and is the same sequence as the terminating 3' nucleotide of the first oligonucleotide probe ("X"), the phosphodiester bond immediately upstream of the flap nucleotide of the second oligonucleotide probe is discriminatingly cleaved by an enzyme having flap endonuclease (FEN) or 5' nuclease activity. That specific FEN activity produces a novel ligation competent 5' phosphate end on the second oligonucleotide probe that is precisely positioned alongside the adjacent 3' OH of the first oligonucleotide probe. Because first and second oligonucleotide probes hybridize adjacent to one another, a ligase seals the nick (FIG. 1C) forming a ligation product that is hybridized to its complementary target nucleic acid molecule. Hybridized ligation products are blended with at least one methylation sensitive restriction enzyme ("RE") to form a methylation sensitive restriction enzyme digestion reaction, where the methylation sensitive restriction enzyme cleaves the ligation product and its hybridized target nucleic acid molecule if the hybridized target nucleic acid molecule does not contain a methylated residue within the methylation sensitive restriction enzyme recognition sequence. However, this enzyme will not cleave the ligation product and its hybridized target nucleic acid molecule if the hybridized target nucleic acid molecule contains one or more methylated residues within the methylation sensitive restriction enzyme recognition sequence (depicted at X'* in FIG. 1). The uncleaved ligation products are detected in the sample to identify methylated residues of a target nucleic acid molecule present in the sample. In this depiction, the first oligonucleotide probe has a 5' primer-specific portion and the second oligonucleotide probe has a 3' primer-specific portion which aid in downstream detection of the ligation product. The oligonucleotide probes may also contain alternative portions related to detection as described herein.

FIG. 1D shows a double nuclease-ligation-restriction enzyme reaction with first, second, and third "middle" oligonucleotide probes. In this embodiment, the first and third oligonucleotide probes of a probe set are configured to hybridize adjacent to one another on the target nucleotide sequence with a junction between them and the third and second oligonucleotide probes of a probe set are configured to hybridize adjacent to one another on the target nucleotide sequence with a junction between them. The target specific portion of the third oligonucleotide probe has an overlapping identical nucleotide flap at the junction with the first oligonucleotide probe in a probe set that is removed by an enzyme having FEN activity when it is complementary to the target nucleotide sequence and is the same sequence as the terminating 3' nucleotide of the first oligonucleotide probe. Likewise, the target specific portion of the second oligonucleotide probe has an overlapping identical nucleotide flap at the junction with the third oligonucleotide probe in a probe set that is removed by an enzyme having FEN activity when it is complementary to the target nucleotide sequence and is the same sequence as the terminating 3' nucleotide of the third oligonucleotide probe. Cleavage of the overlapping flaps liberates a ligation competent 5' phosphate on the third oligonucleotide probe and on the second oligonucleotide probe that allows ligation between the first and third probes and between the second and third probes at their respective junctions to form a ligation product. The utilization of three probes in a probe set allows for detection of distant methylated residues in longer target regions.

In accordance with this aspect of the present invention, flap endonucleases or 5' nucleases that are suitable for cleaving the 5' flap of the second oligonucleotide probe prior to ligation include, without limitation, polymerases the bear 5' nuclease activity such as *E. coli* DNA polymerase and polymerases from Taq and *T. thermophilus*, as well as T4 RNase H and TaqExo.

The ligation reaction utilized in this and all aspects of the present invention is well known in the art. Ligases suitable for ligating oligonucleotide probes of a probe set together at a ligation junction include, without limitation, *Thermus aquaticus* ligase, *E. coli* ligase, T4 DNA ligase, T4 RNA ligase, Taq ligase, 9 N° ligase, and *Pyrococcus* ligase, or any other thermostable ligase known in the art. In accordance with the present invention, the nuclease-ligation process of the present invention can be carried out by employing an oligonucleotide ligation assay (OLA) reaction (see Landegren, et al., "A Ligase-Mediated Gene Detection Technique," Science 241:1077-80 (1988); Landegren, et al., "DNA Diagnostics—Molecular Techniques and Automation," Science 242:229-37 (1988); and U.S. Pat. No. 4,988,617 to Landegren, et al.), a ligation detection reaction (LDR) that utilizes one set of complementary oligonucleotide probes (see e.g., WO 90/17239 to Barany et al, which is hereby incorporated by reference in their entirety), or a ligation chain reaction (LCR) that utilizes two sets of complementary oligonucleotide probes (see e.g., WO 90/17239 to Barany et al, which is hereby incorporated by reference in their entirety).

The oligonucleotide probes of a probe sets can be in the form of ribonucleotides, deoxynucleotides, modified ribonucleotides, modified deoxyribonucleotides, peptide nucleotide analogues, modified peptide nucleotide analogues, modified phosphate-sugar-backbone oligonucleotides, nucleotide analogs, and mixtures thereof.

In accordance with this and all aspects of the present invention, a "methylation sensitive restriction enzyme" is an endonuclease that will not cleave its cognate recognition sequence in a nucleic acid molecule when it contains a methylated residue (i.e., it is sensitive to the presence of a methylated residue within its recognition sequence). A "methylation sensitive restriction enzyme recognition sequence" is the cognate recognition sequence for a methylation sensitive restriction enzyme. For the examples below, the methylated residue is a 5-methyl-C, within the sequence CpG (i.e. 5-methyl-CpG). A non-limiting list of methylation sensitive restriction endonuclease enzymes that are suitable for use in the methods of the present invention include, without limitation, AciI, HinP1I, Hpy99I, HpyCH4IV, BstUI, HpaII, HhaI, or any combination thereof.

Figures 2A, 2B, 2C, 2D, 2E, 2F, 2G, 2H, 2I:
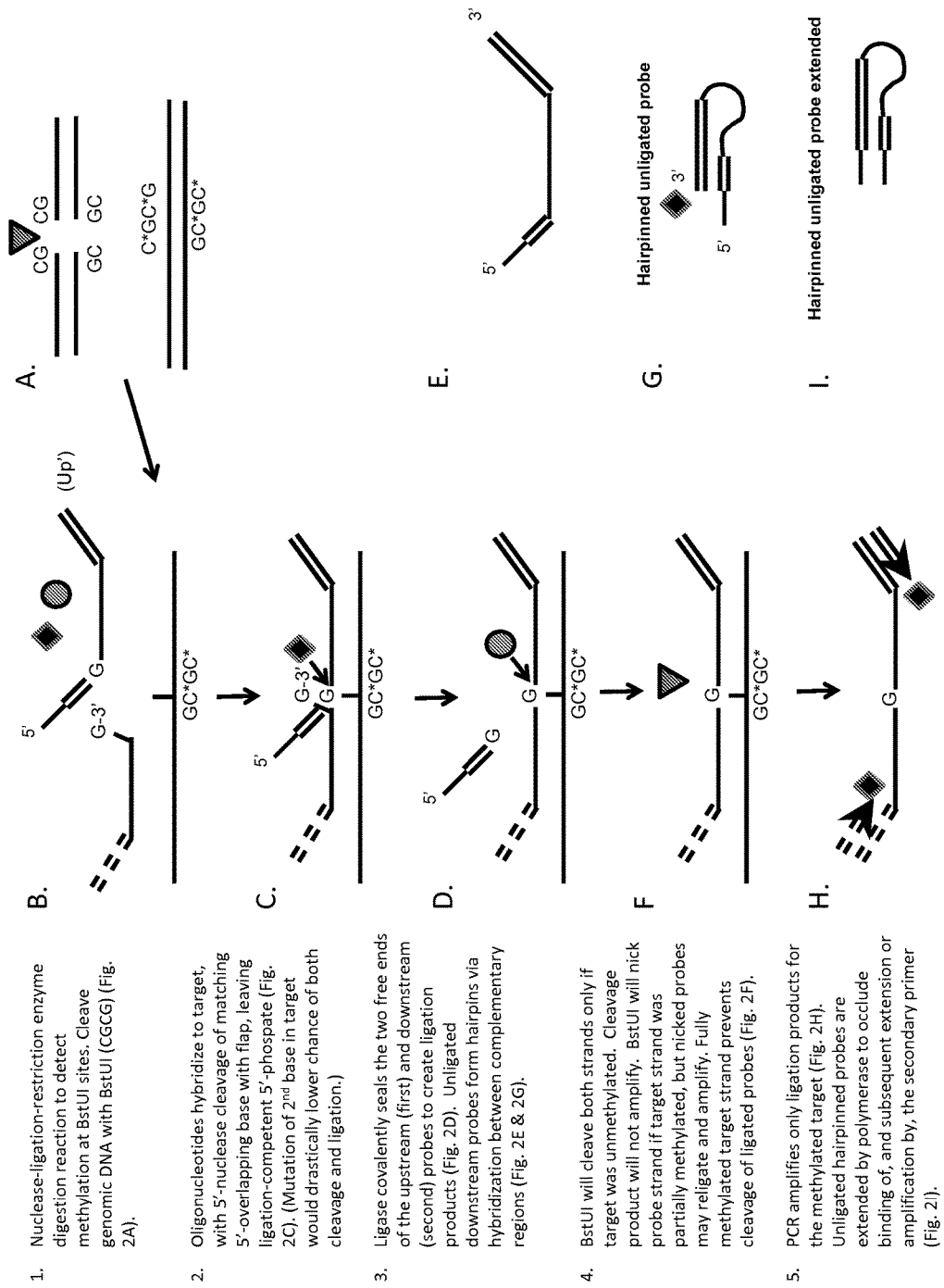
FIGS. 2A-2I show the FEN-ligation-methylation sensitive restriction enzyme digestion reaction process of the present invention to detect methylation of target nucleic acid molecules at BstU1 methylation sites (i.e., C*GC*G sites).

FIGS. 2A-2I depict an embodiment of this aspect of the present invention where methylation at one or more BstU1 recognition sequences within a target nucleic acid molecule is detected. As depicted in FIG. 2A, an optional initial step of this method involves a BstU1 digestion step to cleave total genomic DNA in the sample. Because BstU1 cleaves non-methylated DNA at its CGCG recognition site, target nucleic acid molecules containing unmethylated BstU1 sites will essentially be occluded from further analysis, thereby enriching the sample for target nucleic acid molecules containing methylated BstU1 sites. As shown in FIG. 2B, the first oligonucleotide probe (also referred to herein as the upstream probe) is designed with a guanine base ("G") on the 3' end, and the second oligonucleotide probe (also referred to herein as the downstream probe) is designed to contain a G near its 5' end. The first oligonucleotide probe depicted in FIG. 2B can further contain a cleavable 3' end blocking group that prevents polymerase extension. Suitable blocking groups include, without limitation a propanol group (3'SpC3), a dideoxy ribose base (3'ddC), or a phosphate (3' phosphate). The second oligonucleotide probe depicted in FIG. 2B further contains a flap region at its 5' end that is complementary to a region on the 3' end of the second oligonucleotide probe. This oligonucleotide probe design facilitates the separation of unligated oligonucleotide probes from ligation products following the ligation step as described in more detail herein and in WO2013/123220 to Barany and Spier, which is hereby incorporated by reference in its entirety. In this depiction, the first oligonucleotide probe has a 5' primer-specific portion and the second oligonucleotide probe has a 3' primer-specific portion which aid in downstream amplification and detection of the ligation product.

In the second step of this method, the first and second oligonucleotide probes hybridize to their complementary target nucleic acid sequence (FIG. 2C). FEN cleavage of the 5'-overlapping base and flap of the second oligonucleotide probe generates a ligation competent 5' phosphate. If the 3' end of the first oligonucleotide probe is modified to contain a cleavable blocking group, this modification can be removed using RNaseH when the probe is designed to contain an internal ribonucleotide base, using Tth Endo IV or E. coli Endo IV when the probe is designed to contain an internal abasic site (e.g., tetrahydrofuran), or using Tth Endo V or E. coli Endo V when the probe is designed to contain an internal U paired to a G on the template (cleavage will liberate the 2nd or 3rd phosphodiester bond 3' to the U-G mismatch). Cleavage of the 3' modified end of the first oligonucleotide probe liberates a 3'OH suitable for ligation.

A ligase covalently seals the 3' end of the first oligonucleotide probe to the newly generated ligation competent 5' end of the second oligonucleotide probe to generate a ligation product comprising a 5' primer specific portion, target specific portions, and a 3' primer specific portion. (Step 3, FIG. 2D). The ligation product hybridized to its target nucleic acid molecule is referred to herein as a double-stranded ligation product. BstU1 is added to the sample to cleave ligation products and hybridized target nucleic acid molecules when the target nucleic acid molecule is not methylated (Step 4, FIG. 2F). The cleaved products are not amplified or detected. BstU1 does not cleave ligation products hybridized to a fully methylated target nucleic acid molecule, i.e., GC*GC* (FIG. 2F). Therefore, the detection of uncleaved ligation products indicates the presence of a methylated BstU1 site within the target nucleic acid molecule. If the target nucleic acid molecule is partially methylated (i.e., GC*GC or GCGC*), BstU1 will cleave ligation product, which, in the presence of ligase, will religate and subsequently be detected. As shown in FIG. 2H (Step 5), the uncleaved ligation product is amplified in a polymerase chain reaction (PCR) using primers specific to the 5' and 3' primer specific portions of the ligation product to form extension products suitable for detection. Suitable methods for detecting the ligation product or extension products thereof are described in more detail herein.

As depicted in FIGS. 2E and 2G, unligated second oligonucleotide probes form a hairpin via hybridization between the complementary 5' and 3' regions of the probe. During PCR amplification of the ligated product sequences (Step 5), hairpinned unligated probes are extended at their 3' end by the polymerase to occlude binding of, and subsequent extension or amplification, by the secondary primer in the reaction (FIG. 2I).

Figures 3A, 3B, 3C, 3D, 3E, 3F, 3G, 3H, 3I:
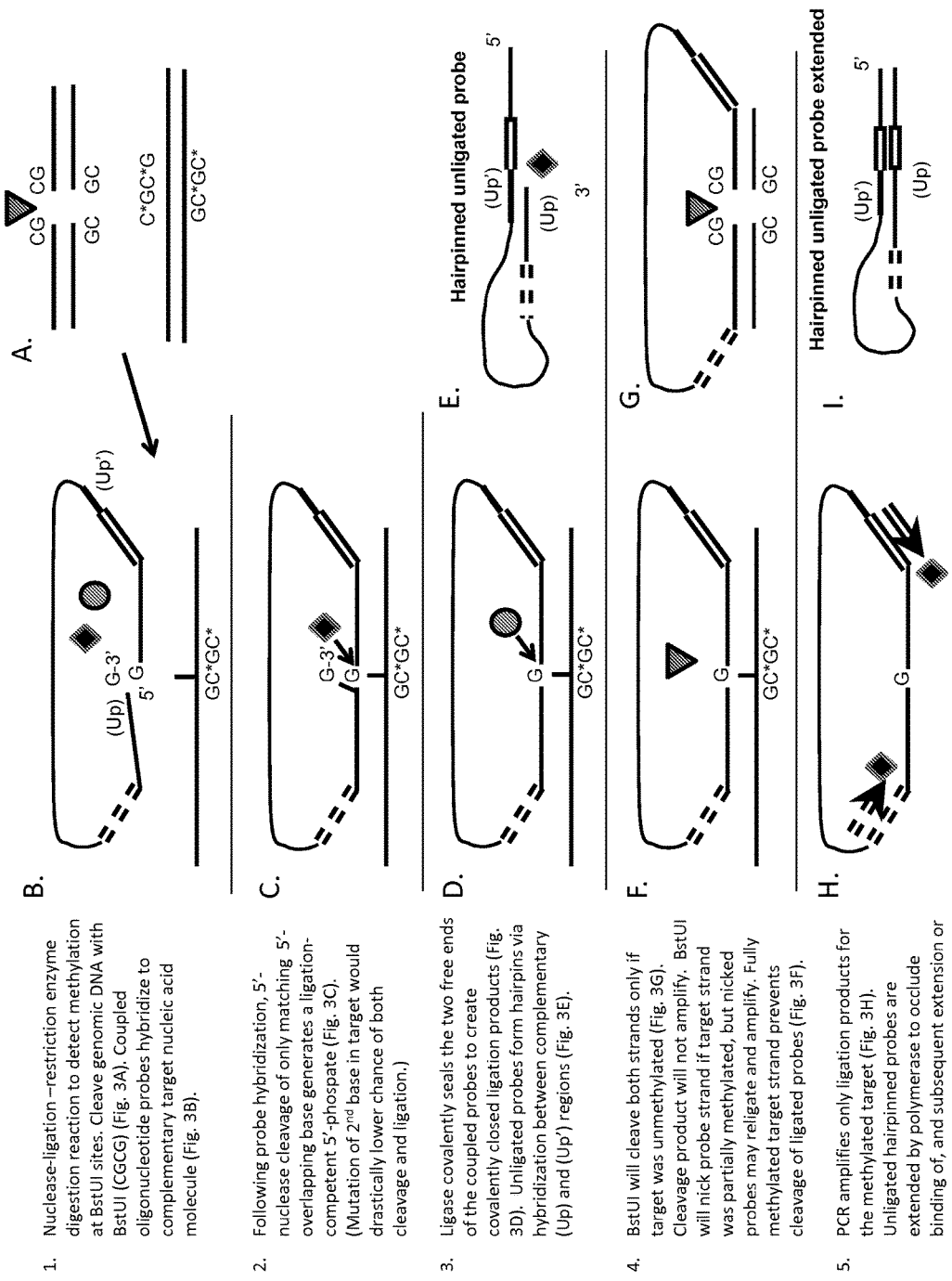
Figures 3J, 3K, 3L, 3M, 3N, 3O, 3P:
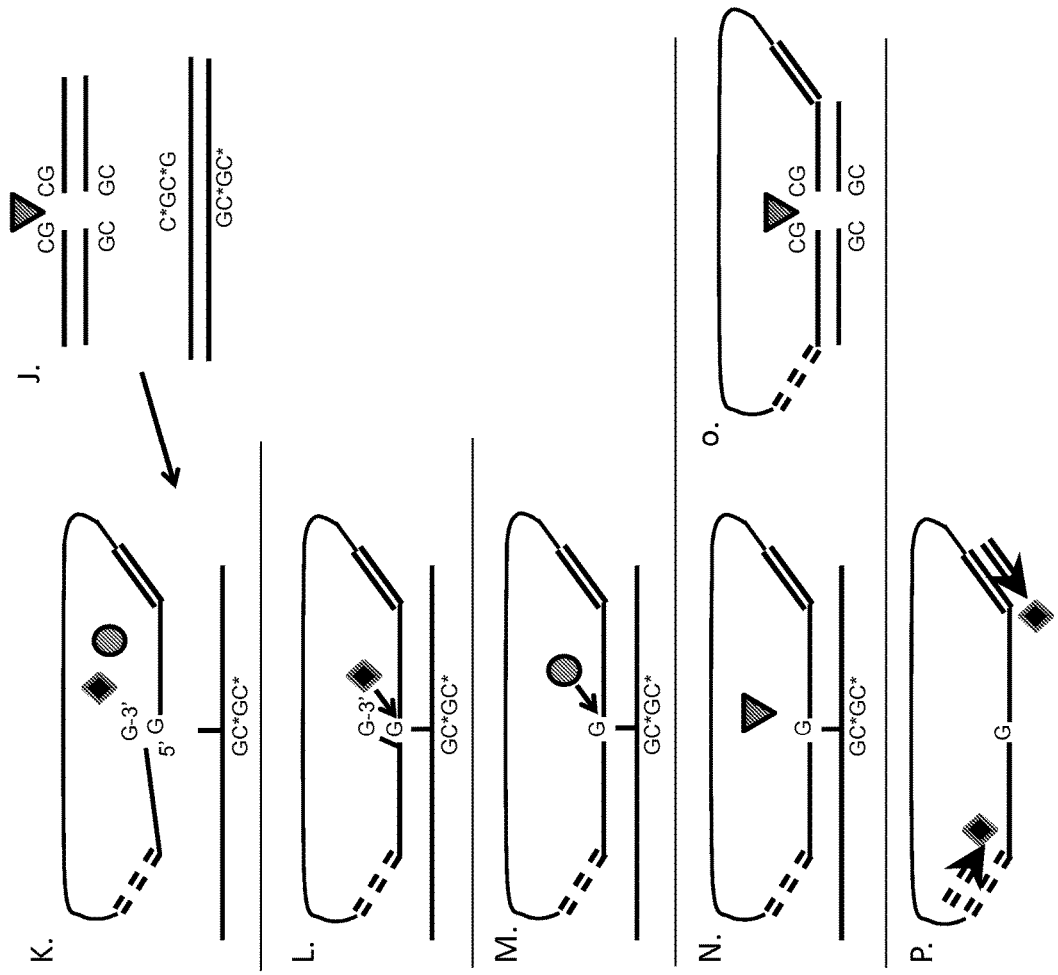

In an alternative embodiment of this aspect of the present invention, the oligonucleotide probes of a probe set are tethered together to form a coupled probe. FIGS. 3A-3I and 3J-3P show variations of the nuclease-ligation reaction process using coupled probes. In accordance with this embodiment, the 5' end of the first oligonucleotide probe is coupled to the 3' end of the second oligonucleotide probe (FIGS. 3B and 3K). The first oligonucleotide probe has a G at its 3' end and the second oligonucleotide probe has a G at or near its 5' end. The first oligonucleotide probe can further contain a cleavable 3' end blocking group that prevents polymerase extension (e.g., 3'SpC3, 3'ddC, or 3' phosphate). Following hybridization of the target-specific portions of the coupled probe to its target nucleic acid molecule, the 5' flap nucleotide is cleaved using nuclease (Step 2, FIGS. 3C and 3L), and the 3' end blocking group of the first oligonucleotide probe if present, is cleaved using RNaseH (at an internal ribonucleotide base), Tth Endo IV or E. coli Endo IV (at an internal abasic site), or Tth Endo V or E. coli Endo V (at an internal U paired to a G on the template). Cleavage of the 5' flap nucleotide of the second oligonucleotide probe and the 3' end blocking group of the first oligonucleotide probe liberates a 5' phosphate and 3'OH, respectively, that are suitable for ligation.

The coupled probe is ligated to form a circular ligation product (Step 3, FIGS. 3D and 3M). BstU1 cleaves both the circular ligation product and the hybridized target nucleic acid sequence when the target nucleic acid sequence is not methylated. Cleaved products are not detected (Step 4, FIGS. 3G and 3O). BstU1 does not cleave the circular ligation product when the target nucleic acid sequence is fully methylated (Step 4, FIGS. 3F and 3N). If the target nucleic acid molecule is partially methylated, BstU1 cleaves the circular ligation product (but not the target nucleic acid molecule), which, in the presence of ligase, will religate. Detection of the circular ligation product indicates the presence of a methylated BstU1 site within the target nucleic acid molecule. As shown in FIGS. 3H and 3P (Step 5), the uncleaved circular ligation product is PCR amplified to form detectable extension products. Suitable methods for detecting the extension products are described in more detail herein.

To reduce target independent false positive signal arising from unligated probes during the reaction process of FIGS. 3A-3I, the coupled oligonucleotide probes can be designed such that unligated probes form hairpins at lower temperature and extend on themselves to form products that do not amplify and are not detected (FIGS. 3E and 3I). To facilitate hairpin formation, the coupled oligonucleotide probe comprises a segment that is complementary to a portion of the 3' end of the probe itself as shown in FIG. 3E. In the absence of ligation, the 3' end portion of the coupled probe hybridizes to the complementary segment to form a hairpinned coupled oligonucleotide probe. Extending the 3' end portion of the coupled hairpinned oligonucleotide probe during the first round of subsequent PCR forms an extended coupled hairpinned oligonucleotide probe that occludes binding of a PCR primer to its complementary sequence (FIG. 3I). An alternative means to reduce false positive signal generation from unligated probes is to incorporate an exonuclease digestion step following ligation as depicted in the process of FIGS. 3J-3P. In this variation, the coupled probes do not need to contain complementary regions required to facilitate hairpin formation.

Another aspect of the present invention is directed to a method for identifying, in a sample, one or more target nucleic acid molecules differing from other nucleic acid molecules in the sample by one or more methylated residues. This method involves providing a sample containing one or more target nucleic acid molecules potentially containing one or more methylated residues within one or more methylation sensitive restriction enzyme recognition sequences, and providing one or more oligonucleotide probe sets, each probe set comprising (a) a first oligonucleotide probe having a target-specific portion, and (b) a second oligonucleotide probe having a target specific portion containing at least one methylation sensitive restriction enzyme recognition sequence. The first and second oligonucleotide probes of a probe set are configured to hybridize on the target nucleic acid molecule. The sample and the one or more oligonucleotide probe sets are contacted under conditions effective for first and second oligonucleotide probes of a probe set to hybridize in a base specific manner to their corresponding target nucleic acid molecule, if present in the sample, to form hybridization products. The method further involves blending at least one methylation sensitive restriction enzyme with the hybridization products, if present in the sample, to form a methylation sensitive restriction enzyme reaction mixture. The methylation sensitive restriction enzyme reaction mixture is subjected to conditions suitable for the methylation sensitive restriction enzyme to cleave the second oligonucleotide probe of a hybridization product at its methylation sensitive restriction enzyme recognition sequence if the target nucleic acid molecule of the hybridization product contains one or more methylated residues within the methylation sensitive restriction enzyme recognition sequence, said cleavage liberating a 5' phosphate on the second oligonucleotide probe. The first and second oligonucleotide probes of the one or more oligonucleotide probe sets are ligated together to form ligation products. The method further involves detecting and distinguishing the ligation products in the sample, and identifying the presence of one or more target nucleic acid molecules differing from other nucleic acid molecules in the sample by one or more methylated residues based on said detecting.

Figures 4A, 4B, 4C, 4D:
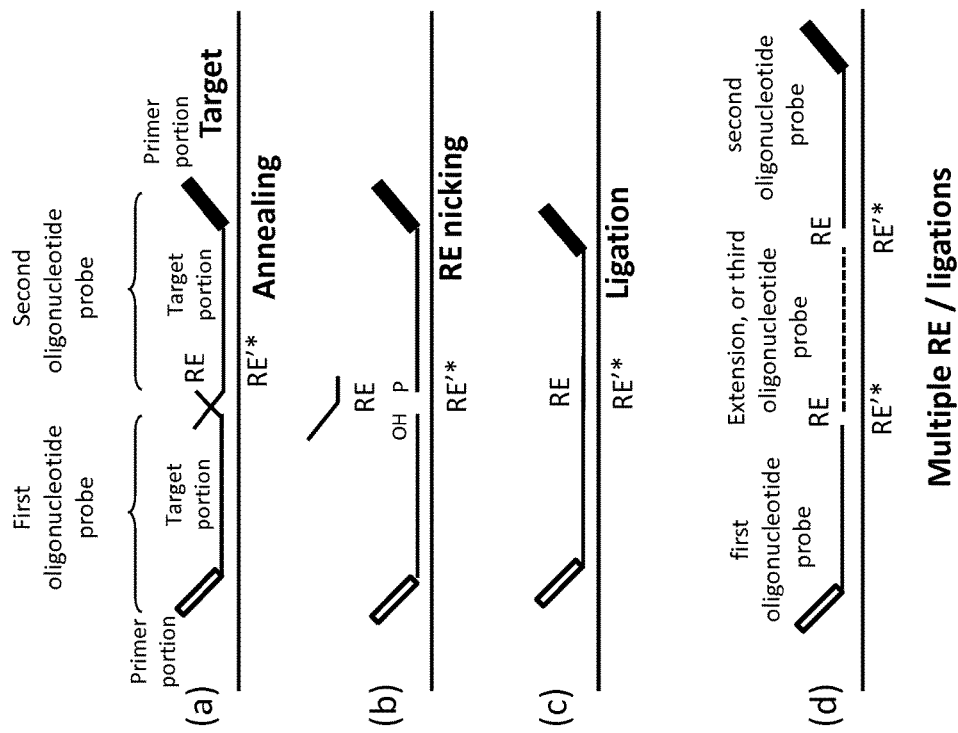
FIGS. 4A-4D show the general process of identifying one or more methylated residues within a methylation sensitive restriction enzyme recognition sequence of a target nucleic acid molecule using the methylation sensitive restriction enzyme digestion-ligation process of the present invention.

FIGS. 4A-4D depict the general process of identifying one or more methylated residues within a methylation sensitive restriction enzyme recognition sequence of a target nucleic acid molecule using the coupled methylation sensitive restriction enzyme digestion-ligation reaction process of the present invention. As shown in FIG. 4A, this method involves at least a first and second oligonucleotide probe. The second oligonucleotide probe has a target-specific portion containing a 5' unmethylated methylation sensitive restriction enzyme recognition sequence (depicted as "RE") that is overlapped by the 3' OH end of the first oligonucleotide probe, also having a target-specific portion. As shown in FIG. 4B, when the second oligonucleotide probe hybridizes to a target nucleic acid molecule containing one or more methylated residues within a methylation sensitive restriction enzyme recognition sequence (depicted as "RE'*"), methylation sensitive restriction enzyme cleavage of the hybridized second oligonucleotide probe generates a ligation competent 5'-phosphate. A ligase seals the two free ends of the first and second oligonucleotide probes (FIG. 4C) forming a ligated product sequence. In this depiction, the first oligonucleotide probe has a 5' primer-specific portion and the second oligonucleotide probe has a 3' primer-specific portion which aid in the amplification and detection of the ligation product. Detection of the ligated product sequence identifies the presence of a methylated target nucleic acid molecule in the sample. FIG. 4D shows a double restriction enzyme-ligation reaction with first, second, and third (middle) oligonucleotide probes.

Figures 5A, 5B, 5C, 5D, 5E, 5F, 5G, 5H:
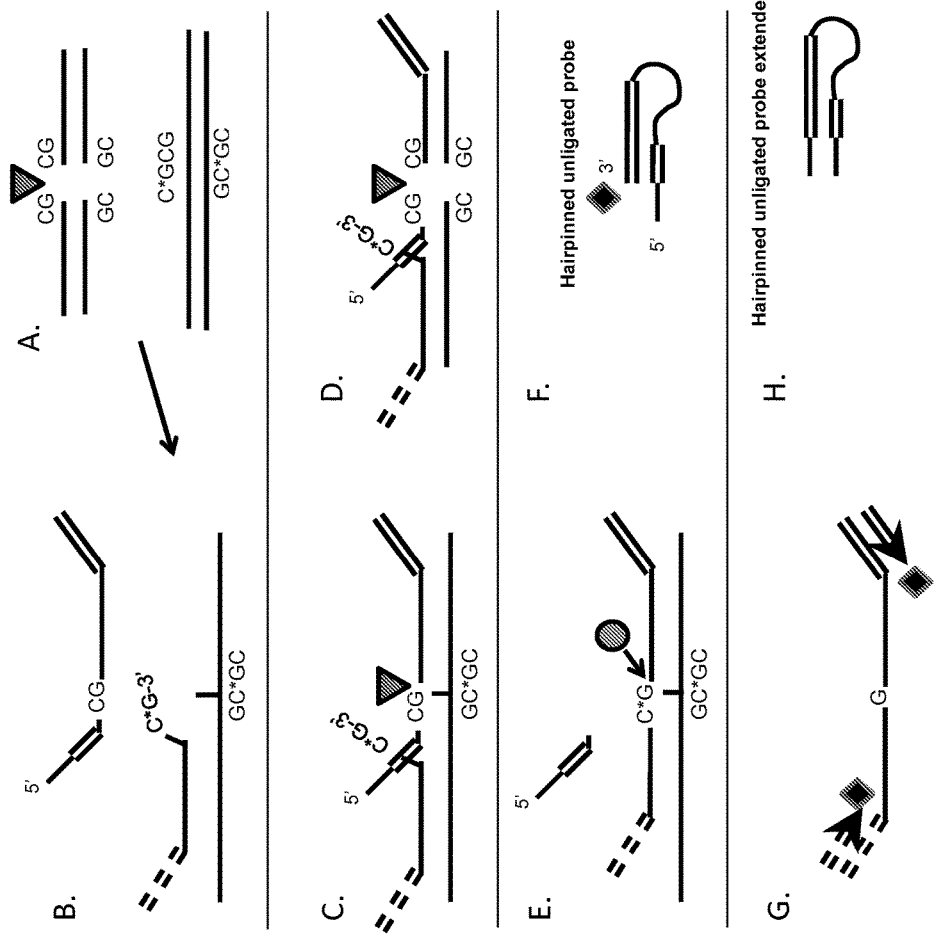
FIGS. 5A-5H show the methylation sensitive restriction enzyme digestion-ligation reaction process of the present invention to detect hemi-methylation at BstU1 methylation sites (e.g., C*GCG sites) in a target nucleic acid molecule. In this embodiment, unligated second oligonucleotide probes are capable of forming hairpins to prevent target independent amplification and false positive signal generation. Restriction endonuclease is shown as a triangle; ligase is shown as a circle; and polymerase as a diamond.
Figures 6I, 6J, 6K, 6L, 6M, 6N:
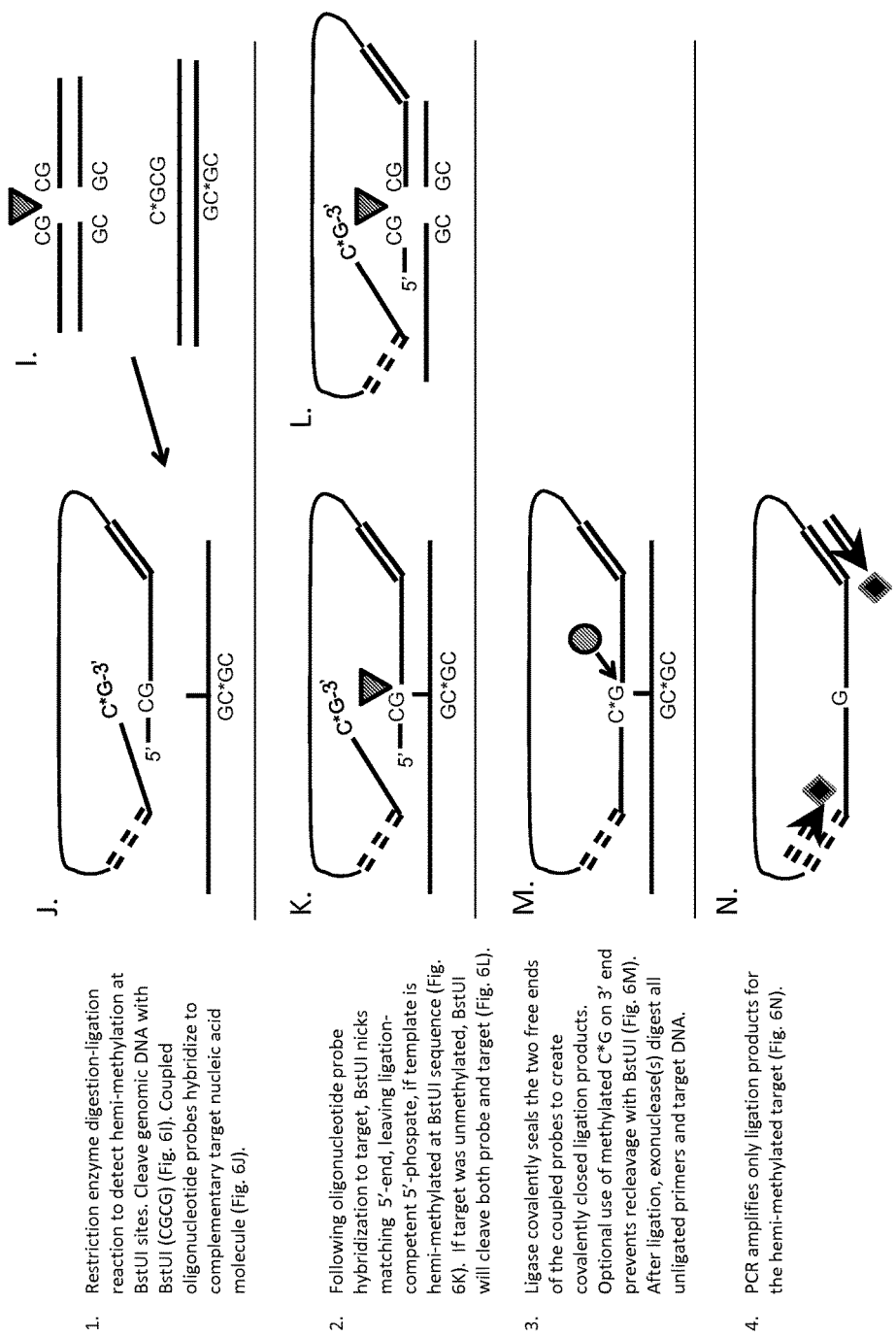

FIGS. 5 and 6 depict embodiments of this aspect of the present invention where methylation at one or more BstU1 recognition sequences within a target nucleic acid molecule is detected. FIGS. 5A-5H depict the method using untethered first and second oligonucleotide probes, while FIGS. 6A-6H and 6I-6N depict variations of the method using tethered or coupled first and second oligonucleotide probes. An optional first step of this method involves a BstU1 digestion step to cleave total genomic DNA in the sample (Step 1, FIGS. 5A, 6A, and 6I). As noted above, this step essentially occludes non-methylated BstU1 sites from further analysis. As shown in FIGS. 5B, 6B, and 6J the 3' end of the first oligonucleotide probe contains cytosine-guanine (CG) nucleotides which are complementary to a portion of the BstU1 site in the target nucleic acid molecule. The first oligonucleotide probe can further contain a cleavable 3' end blocking group that prevents polymerase extension (e.g., 3'SpC3, 3'ddC, or 3' phosphate). The second oligonucleotide probe, designed to contain the entire BstU1 recognition sequence, also has CG nucleotides at or near its 5' end. The second oligonucleotide probe depicted in FIG. 5B further contains a flap region at its 5' end that is complementary to a downstream 3' region to facilitate hairpin formation in the absence of ligation as described above. The oligonucleotide probes of FIGS. 5B, 6B, and 6J further comprise 5' and 3' primer-specific portions which aid in downstream amplification and detection of the ligation product.

In accordance with this embodiment of the present invention, the first and second oligonucleotide probes hybridize to their complementary target nucleic acid sequence (Step 2, FIGS. 5C, 6C, and 6K). BstU1 cleavage of the 5'-overlapping nucleotide bases and flap of the second oligonucleotide probe generates a ligation competent 5' phosphate when the target nucleic acid molecule is hemi-methylated (Step 2, FIGS. 5C, 6C, and 6K). If the target nucleic acid molecule is unmethylated, BstU1 cleaves both the second oligonucleotide probe and the hybridized target nucleic acid molecule, excluding it from further analysis (FIGS. 5D, 6D, and 6L). Likewise, if the target nucleic acid molecule is fully methylated at the BstU1 site, BstU1 cleavage will not occur, preventing downstream probe ligation and detection. If the 3' end of the first oligonucleotide probe is modified to contain a cleavable blocking group, this modification is removed as described supra. Cleavage of the 3' modified end of the first oligonucleotide probe liberates a 3'OH suitable for ligation.

Following BstU1 cleavage of the 5' end of the second oligonucleotide probe, the 3' end of the first oligonucleotide probe hybridizes to the target nucleic acid molecule thereby generating a ligation junction between the first and second oligonucleotide probes that is sealed by a ligase (Step 3, FIGS. 5E, 6E, and 6M). As depicted in FIGS. 5E, 6E, and 6M, designing the first oligonucleotide probe to contain a methylated cytosine (C*) at its 3' end prevents re-cleavage by BstU1 upon hybridization of the 3' end of the first oligonucleotide probe to the target nucleic acid molecule. The linear ligation product of FIG. 5G and circular ligation products of FIGS. 6G and 6N are suitable for PCR amplification (Step 4) to generate extension products that are suitable for detection, thereby identifying the presence of hemi-methylated BstU1 sites in target nucleic acid molecules of a sample.

To reduce target independent false positive signal arising from unligated probes during the reaction process the oligonucleotide probes can be designed such that unligated probes form hairpins at lower temperature and extend on themselves to form products that do not amplify and are not detected (FIGS. 5F and 5H and FIGS. 6F and 6H). As depicted in FIGS. 5F and 6F, unligated probes form a hairpin via hybridization between complementary 5' and 3' regions. During PCR amplification of the ligated product sequences (Step 4), hairpinned unligated probes are extended at their 3' end by the polymerase to occlude binding of, and subsequent extension or amplification, by the secondary primer in the PCR reaction (FIGS. 5H and 6H). An alternative means to reduce false positive signal generation from unligated coupled probes is to incorporate an exonuclease digestion step following ligation as depicted in the process of FIGS. 6I-6N. In this variation, the coupled probes do not need to contain complementary regions required to facilitate hairpin formation.

Figures 7A, 7B, 7C, 7D, 7E, 7F, 7G, 7H:
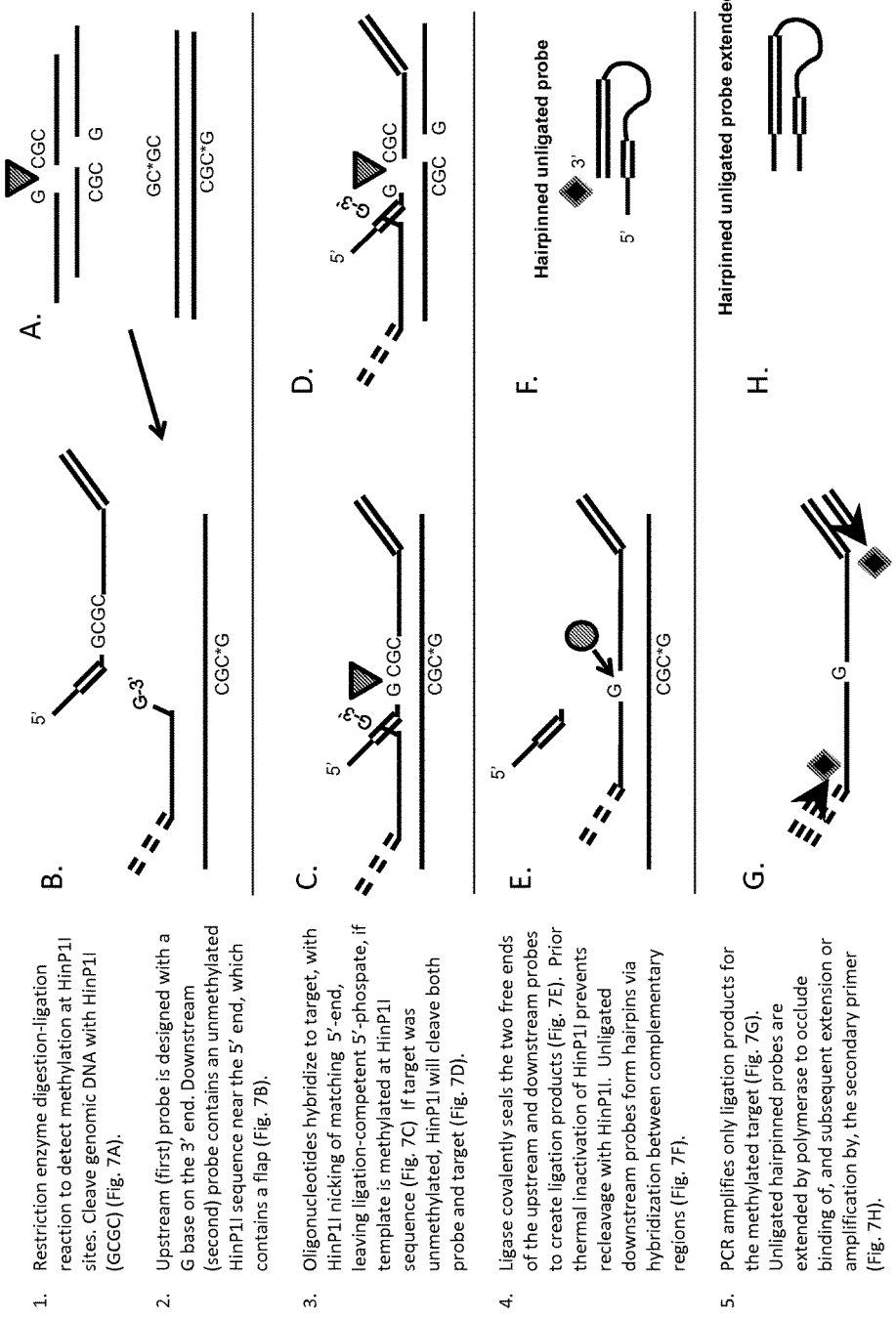
FIGS. 7A-7H show the methylation sensitive restriction enzyme digestion-ligation reaction process of the present invention to detect methylation at HinP1I methylation sites (e.g., G*CGC sites) in a target nucleic acid molecule. In this embodiment, unligated second oligonucleotide probes are capable of forming hairpins to prevent target independent amplification and false positive signal generation. Restriction endonuclease is shown as a triangle; ligase is shown as a circle; and polymerase as a diamond.
Figures 8A, 8B, 8C, 8D, 8E, 8F, 8G, 8H:
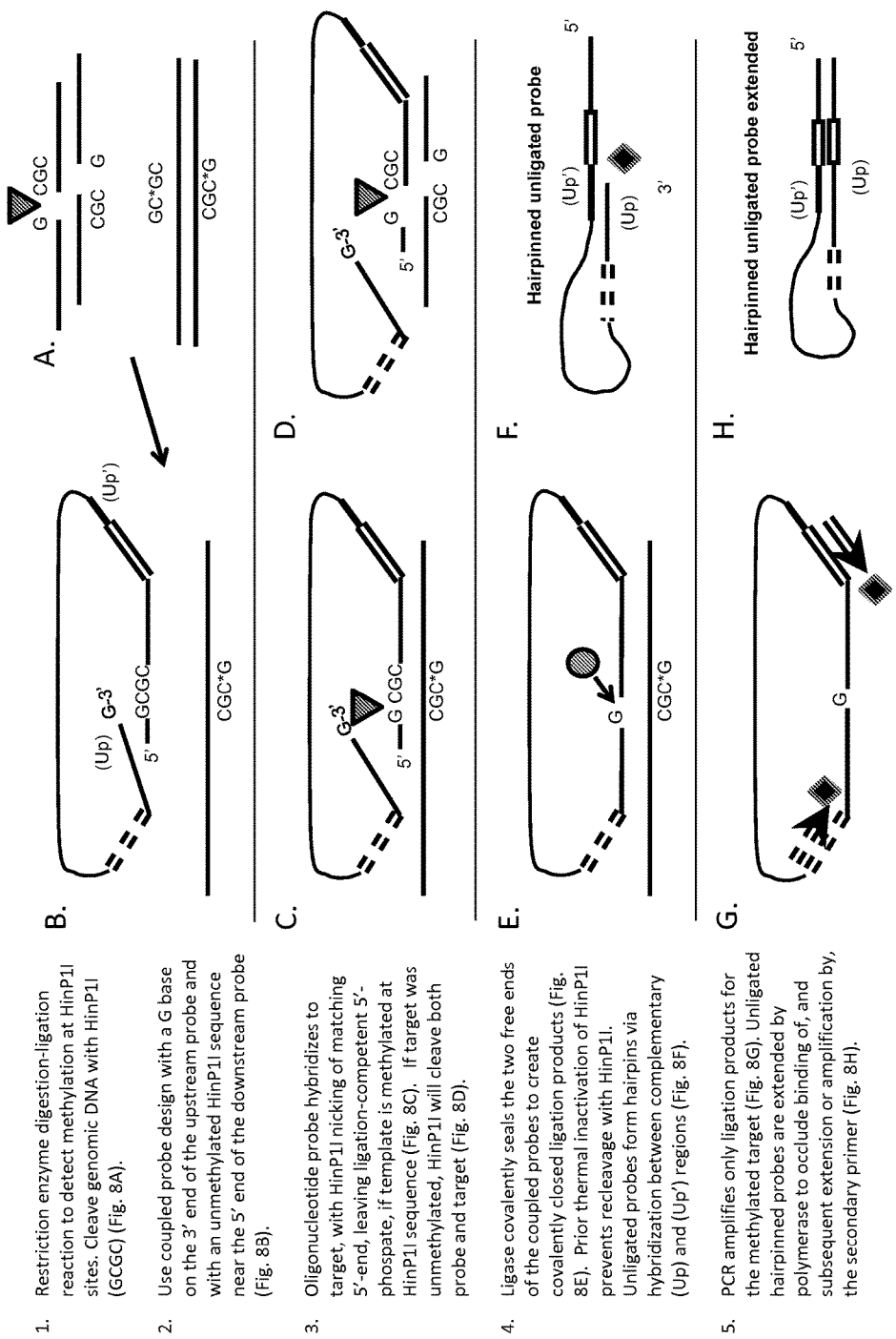

FIGS. 7 and 8 depict embodiments of this aspect of the present invention where methylation at one or more HinP1I recognition sequences (i.e., GCGC) within a target nucleic acid molecule is detected. FIGS. 7A-7H depict the method using untethered first and second oligonucleotide probes, while FIGS. 8A-8H and 8I-8N depict the method using coupled first and second oligonucleotide probes. An optional first step of this method involves a HinP1I digestion step to cleave total genomic DNA in the sample (Step 1, FIGS. 7A, 8A, and 8I). Since HinP1I cleaves DNA at its unmethylated GCGC recognition sequence, this step essentially occludes non-methylated HinP1I sites from further analysis.

As shown in FIGS. 7B, 8B, and 8J, the 3' end of the first oligonucleotide probe contains a G nucleotide which is complementary to a portion of the HinP1I site in the target nucleic acid molecule. The first oligonucleotide probe can further contain a cleavable 3' end blocking group that prevents polymerase extension (e.g., 3'SpC3, a 3'ddC, or 3' phosphate). The second oligonucleotide probe, designed to contain the entire HinP1I recognition sequence, also has G nucleotide at or near its 5' end. The second oligonucleotide probe depicted in FIG. 7B further contains a flap region at its 5' end that is complementary to a downstream 3' region of the probe to facilitate hairpin formation in the absence of ligation as described above. The oligonucleotide probes of FIGS. 7B, 8B, and 8J further comprise 5' and 3' primer-specific portions which aid in downstream amplification and detection of the ligation product.

In accordance with this embodiment of the present invention, the first and second oligonucleotide probes hybridize to their complementary target nucleic acid sequence (FIGS. 7C, 8C, and 8K). HinP1I cleavage of the 5'-overlapping nucleotide base and flap of the second oligonucleotide probe generates a ligation competent 5' phosphate when the hybridized target nucleic acid molecule is methylated (Step 2, FIGS. 7C, 8C, and 8K). If the target nucleic acid molecule is unmethylated, HinP1I cleaves both the second oligonucleotide probe and the hybridized target nucleic acid molecule, excluding it from further analysis (FIGS. 7D, 8D, and 8L). If the 3' end of the first oligonucleotide probe is modified to contain a cleavable blocking group, this modification is removed using a restriction endonuclease to nick an unmethylated oligonucleotide strand hybridized to a methylated target strand, or any other suitable cleaving enzyme as described supra. Cleavage of the 3' modified end of the first oligonucleotide probe liberates a 3' OH suitable for ligation.

Following HinP1I cleavage of the 5' end of the second oligonucleotide probe, the 3' end of the first oligonucleotide probe hybridizes to the target nucleic acid molecule thereby generating a ligation junction between the first and second oligonucleotide probes that is sealed by a ligase (Step 4, FIGS. 7E, 8E, and 8M). HinP1I can be thermally inactivated to prevent re-cleavage following hybridization of the 3' end of the first oligonucleotide probe to the target nucleic acid molecule and ligation to the second oligonucleotide probe. The linear ligation product of FIG. 7G and circular ligation products of FIGS. 8G and 8N are suitable for PCR amplification (Step 5) to generate extension products that are suitable for detection, thereby identifying the presence of methylated HinP1I sites in target nucleic acid molecules of a sample.

As depicted in FIGS. 7F and 8F, oligonucleotide probes can be designed to form a hairpin via hybridization between complementary 5' and 3' regions in the absence of ligation. During PCR amplification of the ligated product sequences (Step 5), hairpinned unligated probes are extended at their 3' end by the polymerase to occlude subsequent extension or amplification by the secondary primer in the PCR reaction (FIGS. 7H and 8H). An alternative means to reduce false positive signal generation from unligated coupled probes is to incorporate an exonuclease digestion step following ligation as depicted in the process of FIGS. 8I-8N. In this variation, coupled probes do not need to contain complementary regions required to facilitate hairpin formation.

Figures 9A, 9B, 9C, 9D, 9E, 9F:
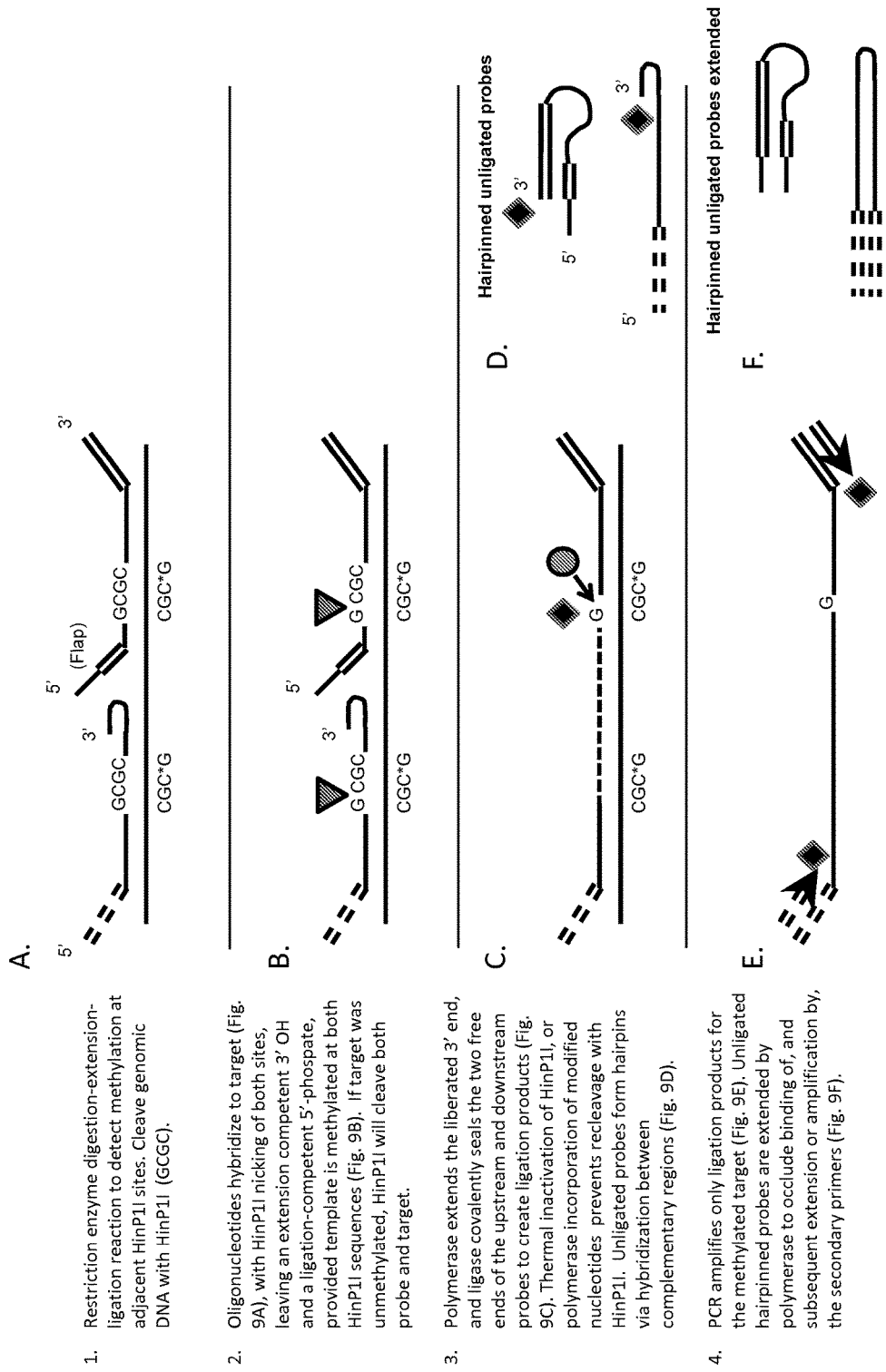
FIGS. 9A-9L show the methylation sensitive restriction enzyme digestion-extension-ligation reaction process of the present invention to detect methylation at adjacent HinP1I methylation sites in a target nucleic acid molecule.
Figures 9G, 9H, 9I, 9J, 9K, 9L:
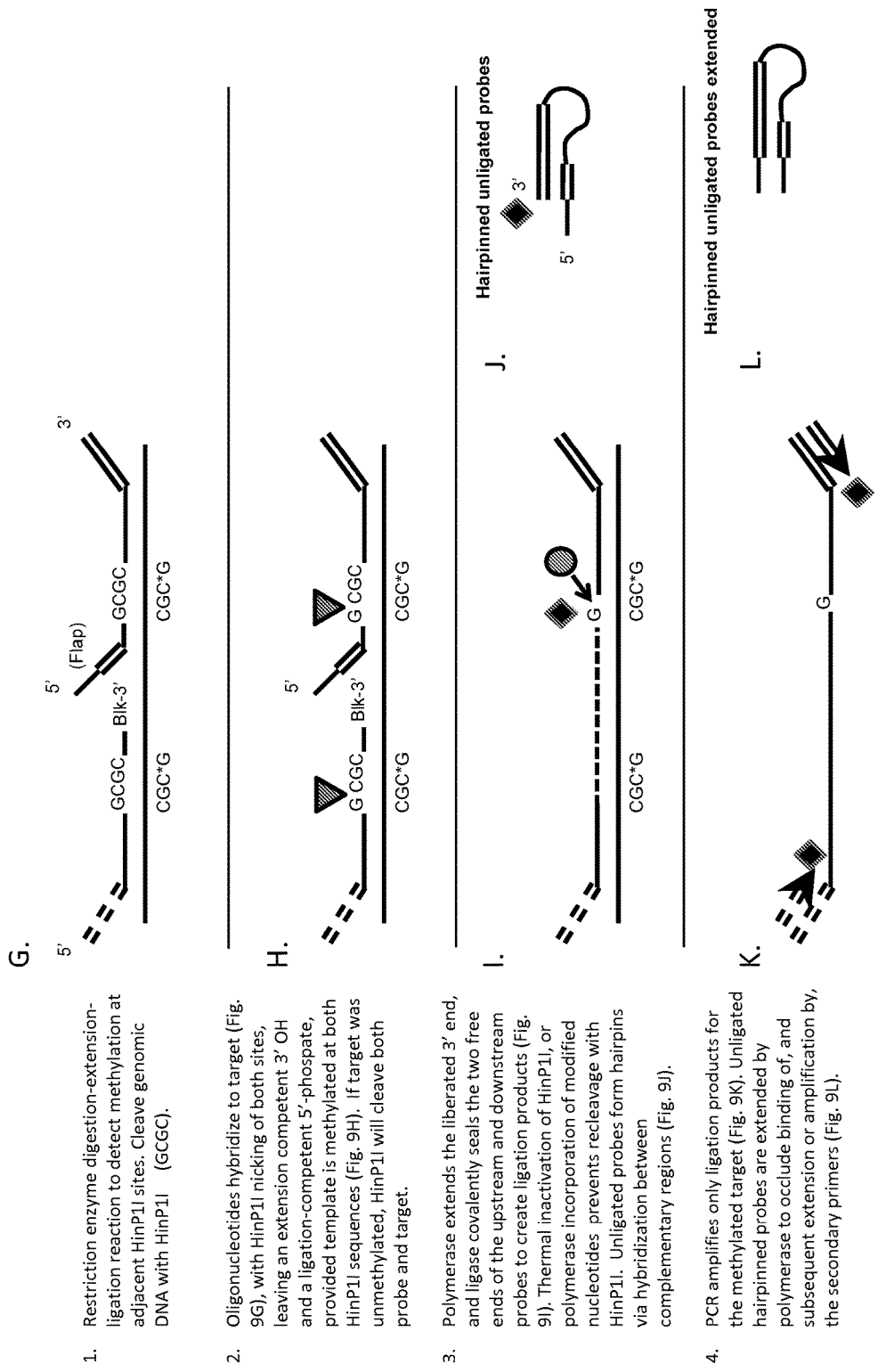
Figures 10A, 10B, 10C, 10D, 10E, 10F:
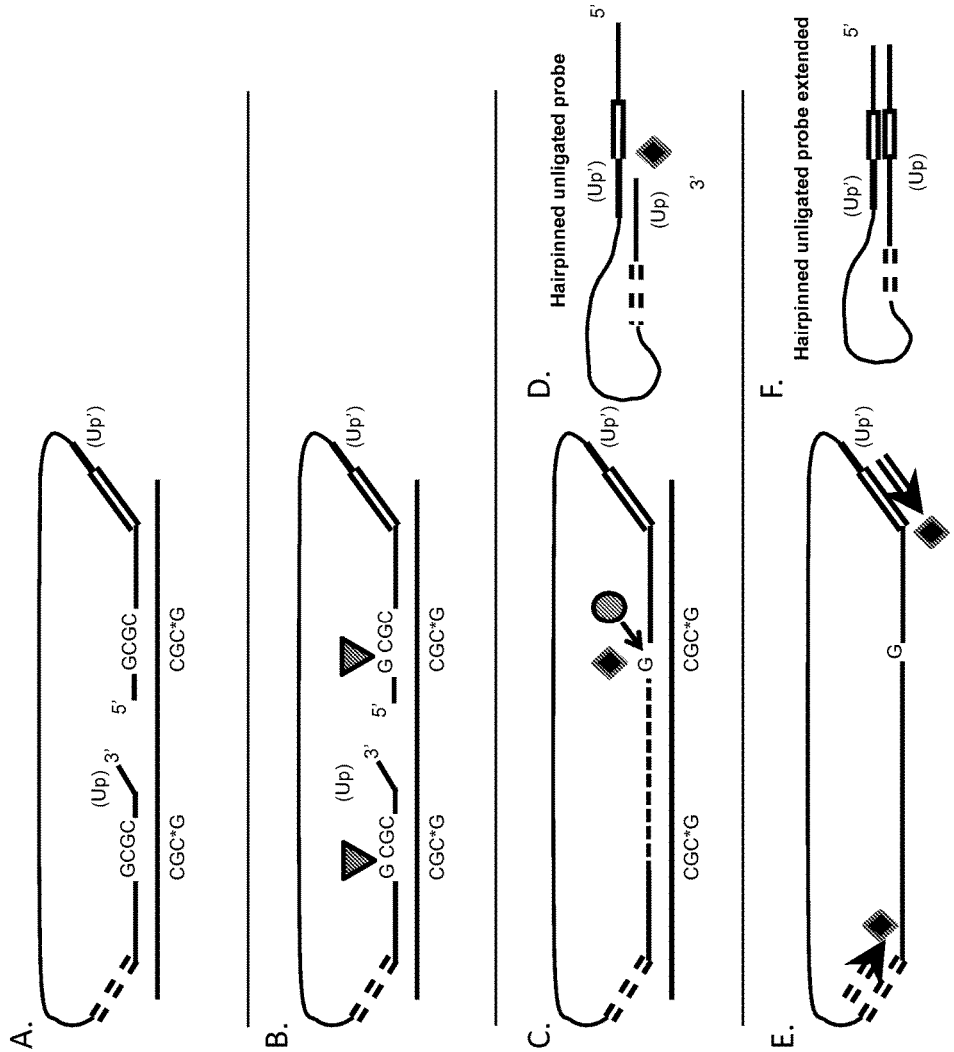
FIGS. 10A-10J show the methylation sensitive restriction enzyme digestion-extension-ligation reaction process of the present invention using a coupled probe design to detect methylation at adjacent HinP1I methylation sites in a target nucleic acid molecule.
Figures 10G, 10H, 10I, 10J:
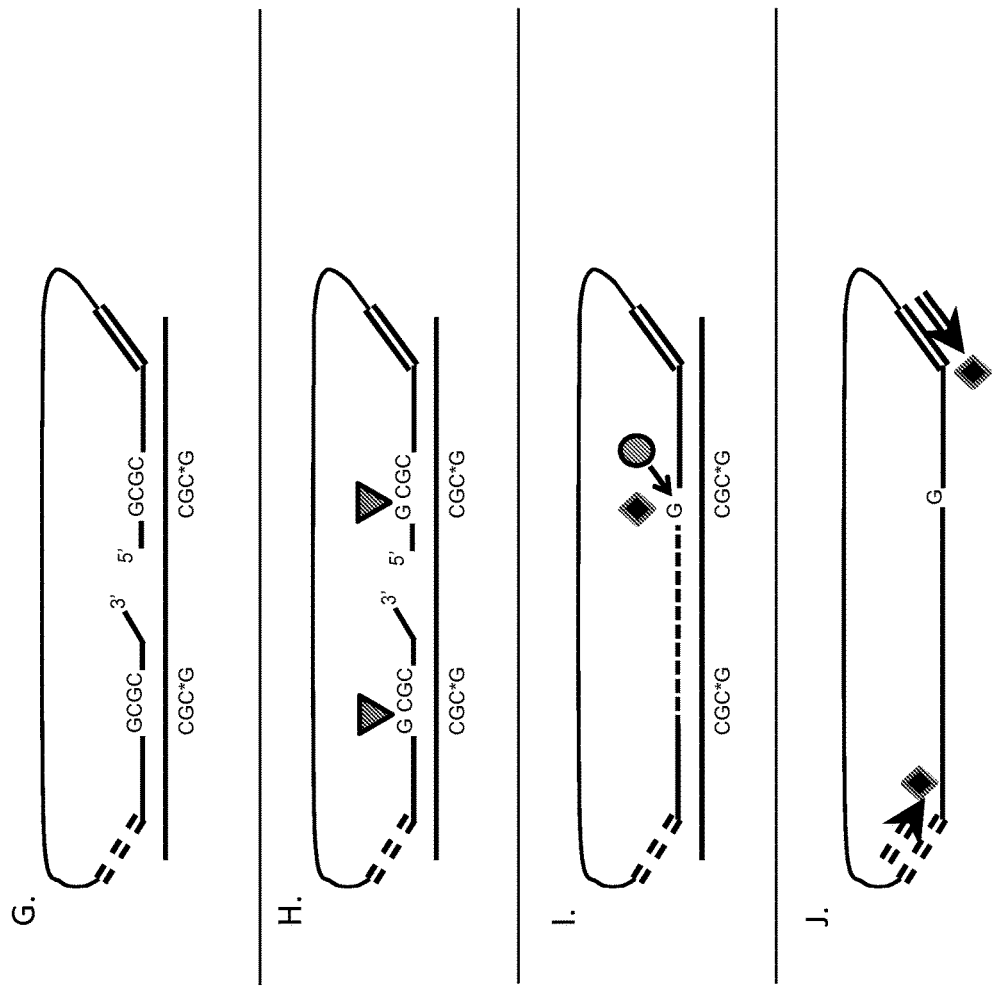

FIGS. 9 and 10 depict an embodiment of this aspect of the present invention that is suitable for detecting methylation at adjacent HinP1I sites within a target nucleic acid molecule. FIGS. 9A-9L depict methods using uncoupled first and second oligonucleotide probes, while FIGS. 10A-10J depict methods using coupled first and second oligonucleotide probes. Although not depicted, an initial HinP1I digestion of the DNA sample can be performed to enrich the sample for methylated HinP1I sites. As shown in FIGS. 9A and 9G, the first oligonucleotide probe of a probe set is designed to contain an unmethylated HinP1I recognition sequence near its 3' end. The 3' end of the first oligonucleotide probe is blocked from polymerase mediated extension via a hairpin (FIG. 9A), a cleavable blocking group (FIG. 9G) (e.g., 3'SpC3, 3'ddC, or 3' phosphate), or other suitable means, and the 5' end of the probe contains a primer specific portion. The second oligonucleotide probe of a probe set contains a HinP1I recognition sequence near its 5' end, an optional 5' flap, and a 3' primer specific portion. When using a coupled probe approach as shown in FIGS. 10A-10J, the first oligonucleotide probe contains an unmethylated HinP1I recognition sequence near its 3' end. The 3' end of the probe in this example contains a nucleotide mismatch to the target nucleotide sequence to prevent polymerase extension (FIGS. 10A and 10G). Alternatively, the 3' end of the first probe can contain a cleavable blocking group as described supra. The first oligonucleotide probe of the coupled probe also contains a 5' primer-specific portion. The second oligonucleotide probe of the coupled probe contains an unmethylated HinP1I recognition sequence near its 5' end and a 3' primer-specific portion (FIGS. 10A and 10G). The coupled probe in the process depicted in FIGS. 10A-10F also contains 3' and 5' regions of complementarity (FIG. 10A "Up"/"Up'") to facilitate hairpin formation of the probe in the absence of ligation.

Following hybridization of the oligonucleotide probes to a complementary methylated target nucleic acid molecule in the processes of FIGS. 9 and 10, HinP1I cleaves the first oligonucleotide probe to generate an extension competent 3'OH and cleaves the second oligonucleotide probe to generate a ligation competent 5'phosphate (Step 2, FIGS. 9B, 9H, 10B, and 10H). A polymerase extends the liberated 3' end of the first oligonucleotide probe to generate a ligation junction between the first and second oligonucleotide probes, and a ligase covalently seals the two free ends of the probes creating a ligation product (Step 3, FIGS. 9C, 9I, 10C, and 10I). HinP1I recleavage of the ligation product can be prevented by incorporating a thermal inactivation step or by polymerase incorporation of modified nucleotides. Only ligation products of methylated target nucleic acid molecules are PCR amplified and detected (Step 4, FIGS. 9E, 9K, 10E, and 10J). Target nucleic acid molecules containing unmethylated residues at either HinP1I site corresponding to the first or second oligonucleotide probes are cleaved by HinP1I along with the hybridized probes, thereby preventing subsequent extension, ligation, and detection.

As depicted in FIGS. 9D and 10D, unligated second oligonucleotide probes and unligated coupled probes form a hairpin via hybridization between complementary 5' and 3' regions. During PCR amplification of the ligated product sequences (Step 4), hairpinned unligated probes are extended at their 3' end by the polymerase to occlude binding of, and subsequent extension or amplification, by the oligonucleotide primers in the PCR reaction (FIGS. 9F and 10F). In the process of FIGS. 10G-10J, the coupled oligonucleotide probe does not form a hairpin in the absence of ligation. In this embodiment, an exonuclease digestion following ligation removes unligated probes from the reaction process.

Figures 11A, 11B, 11C, 11D, 11E, 11F:
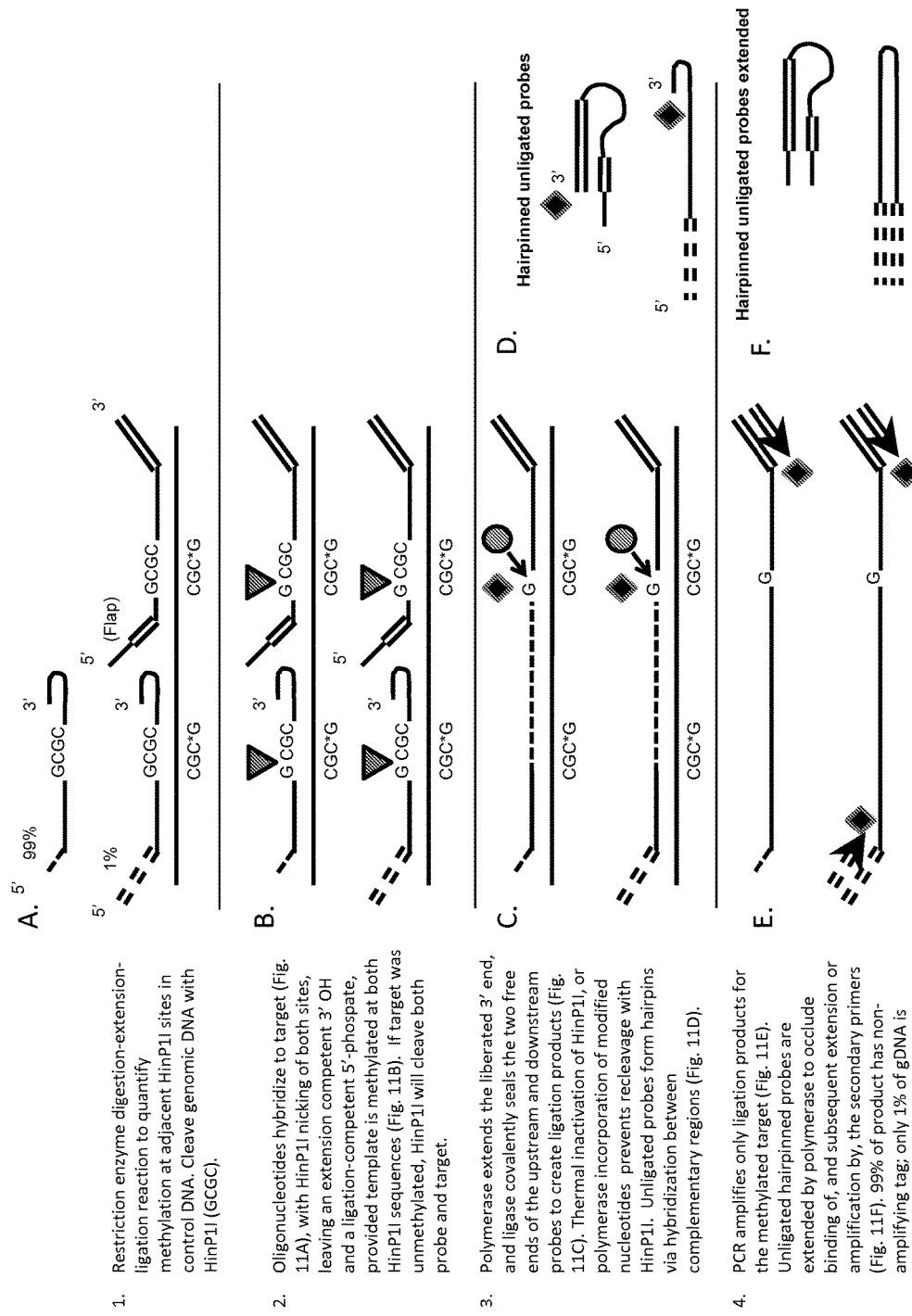
FIGS. 11A-11F depict how a known region of DNA can be used as a positive control in the same reaction mixtures shown in FIG. 9, to provide a control signal equivalent to the presence of 1% of methylated DNA.

FIGS. 11A-11F demonstrate how a known region of a nucleic acid molecule can be used as a positive control in the same reaction mixture shown in FIG. 9, to provide a control signal equivalent to the presence of 1% of methylated DNA. Two first oligonucleotide probes, each containing an unmethylated HinP1I site and a 3' hairpin region or blocking group are provided, where one of the first oligonucleotide probes contains a 5' primer-specific portion or other amplifying tag and the other first oligonucleotide probe does not contain the 5' primer-specific portion or contains a non-amplifying tag (FIG. 11A). The two first oligonucleotide probes are provided in a mixture in a known ratio, e.g. 1:99, respectively. The second oligonucleotide probe contains a HinP1I site and a 5' flap as described above with reference to FIG. 9. Oligonucleotide probes are hybridized to the control DNA, HinP1I cleavage is carried out to generate extension competent 3' OH ends on the first oligonucleotide probes and a ligation competent 5' end on the second oligonucleotide probe (Step 2, FIG. 11B). Polymerase extends the liberated 3' ends of the first oligonucleotide probes to create a ligation junction with the second oligonucleotide probe, and a ligase covalently seals the free ends of the probes (Step 3, FIG. 11C). PCR amplifies only the ligation products. Since 99% of the ligation products contain a non-amplifying tag, only the 1% of ligation products containing the 5' primer-specific portion will be amplified and detected (Step 4, FIG. 11D). The signal generated from the control reaction is equivalent to the signal that would be generated from a methylated target nucleic acid molecule present in 1% of the DNA sample. Unligated probes form hairpins that are polymerase extended during PCR amplification of the ligation products (FIGS. 11D and 11F).

FIGS. 12A-12D depict the nuclease-ligation reaction process of the present invention to detect methylation at distant HinP1I sites on the same target nucleic acid molecule. In accordance with this embodiment, coupled first and second probes are used in conjunction with a third or middle probe. The 3' end of the first oligonucleotide probe of the coupled probe contains a G nucleotide which is complementary to a portion of a first HinP1I site in the target nucleic acid molecule. The 3' end of the first probe may also contain a cleavable blocking group as described supra. The 5' end of the middle probe is designed to contain the entire HinP1I recognition sequence that is complementary to the first HinP1I site in the target nucleic acid molecule. The G nucleotide residue of the recognition sequence which is at or near the 5' end of the middle probe overlaps with the 3' G nucleotide residue of the first oligonucleotide probe. The 3' end of the middle probe is designed to contain a G nucleotide which is complementary to a portion of a second HinP1I site in the target nucleic acid molecule that is distant from the first HinP1I site. The 3' end of the middle probe may also contain a cleavable blocking group as described supra. The second oligonucleotide probe of the coupled probe is designed to contain the entire HinP1I recognition sequence that is complementary to the second HinP1I site in the target nucleic acid molecule. The G nucleotide residue of the recognition sequence which is at or near the 5'end of the second probe overlaps with the 3' G nucleotide residue of the middle oligonucleotide probe. The first and second oligonucleotide probes of the coupled probe also contain 5' and 3' primer-specific portions.

Figures 12A, 12B, 12C, 12D:
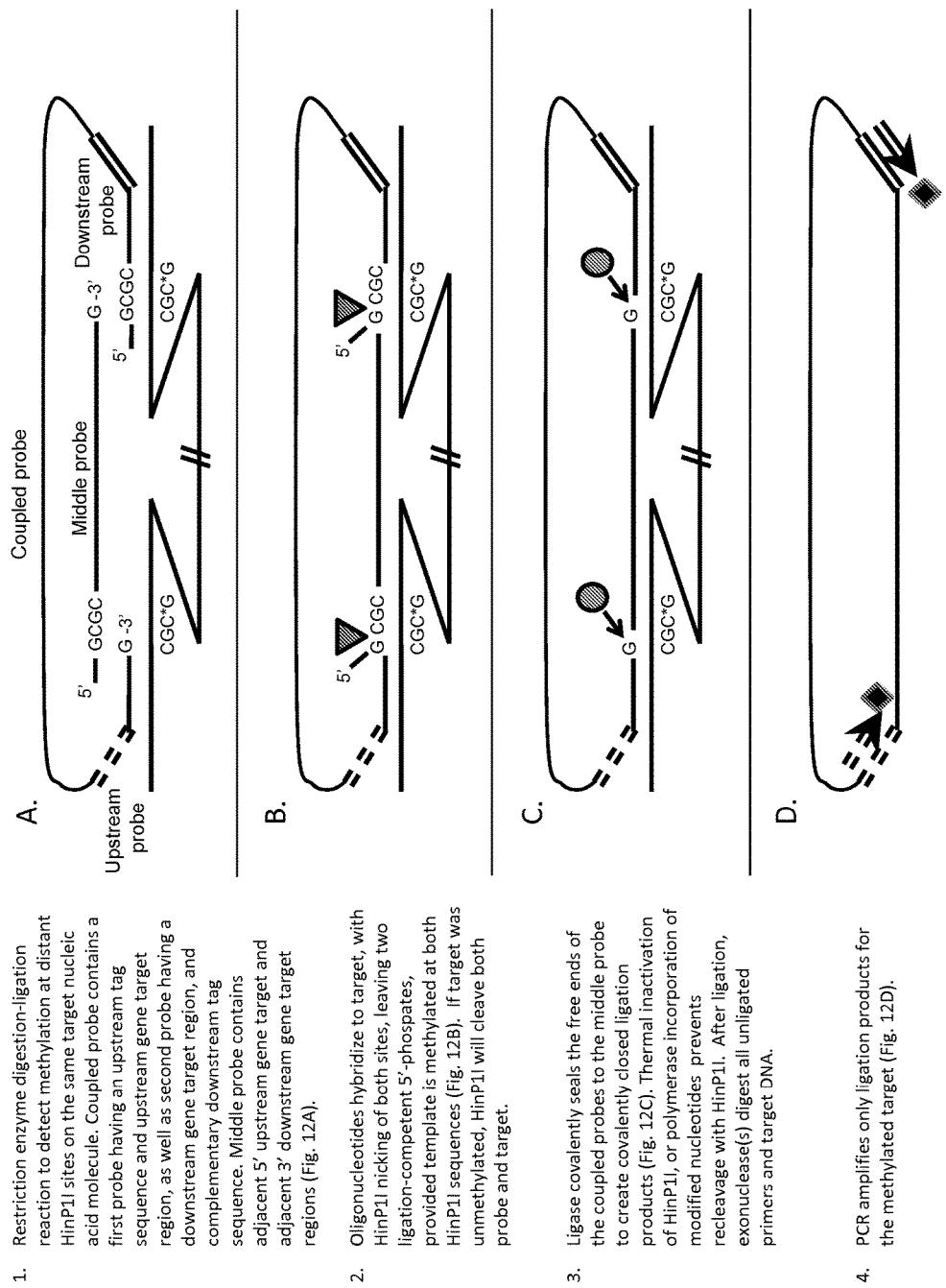
FIGS. 12A-12D show the methylation sensitive restriction enzyme digestion-ligation reaction process of the present invention to detect methylation at distant HinP1I methylation sites in a target nucleic acid molecule. Restriction endonuclease is shown as a triangle; ligase is shown as a circle; polymerase as a diamond; undefined distance between HinP1I sites in target nucleic acid molecule indicated by "//".

In accordance with this embodiment of the present invention, the first, middle, and second oligonucleotide probes hybridize to their complementary target nucleic acid sequence (FIG. 12B). When the hybridized target nucleic acid molecule is methylated, HinP1I cleaves the 5'-overlapping nucleotide base of the middle and second oligonucleotide probes, respectively, to generate ligation competent 5' ends on each probe (Step 2, FIG. 12B). If the target nucleic acid molecule is unmethylated, HinP1I cleaves both the middle and second oligonucleotide probe as well as the hybridized target nucleic acid molecule, thereby excluding it from further analysis. If the 3' end of the first and/or middle probe contains a cleavable blocking modification, this modification is removed using a suitable cleaving enzyme as described supra. Cleavage of the 3' blocking group of the first oligonucleotide probe liberates a 3'OH suitable for ligation.

Following HinP1I cleavage of the 5' end of the middle oligonucleotide probe, the 3' end of the first oligonucleotide probe hybridizes to the target nucleic acid molecule thereby generating a ligation junction between the first and middle oligonucleotide probes that is sealed by a ligase (Step 3, FIG. 12C). Likewise, following HinP1I cleavage of the 5' end of the second oligonucleotide probe, the 3' end of the middle oligonucleotide probe hybridizes to the target nucleic acid molecule thereby generating a ligation junction between the middle and second oligonucleotide probes that is sealed by a ligase (Step 3, FIG. 12C). HinP1I can be thermally inactivated to prevent re-cleavage following hybridization and ligation of the probes. The circular ligation product of FIG. 12D is suitable for PCR amplification (Step 4) to generate extension products that are suitable for detection, thereby identifying the presence of distant methylated HinP1I sites in the same target nucleic acid molecule.

Figures 13A, 13B, 13C, 13D:
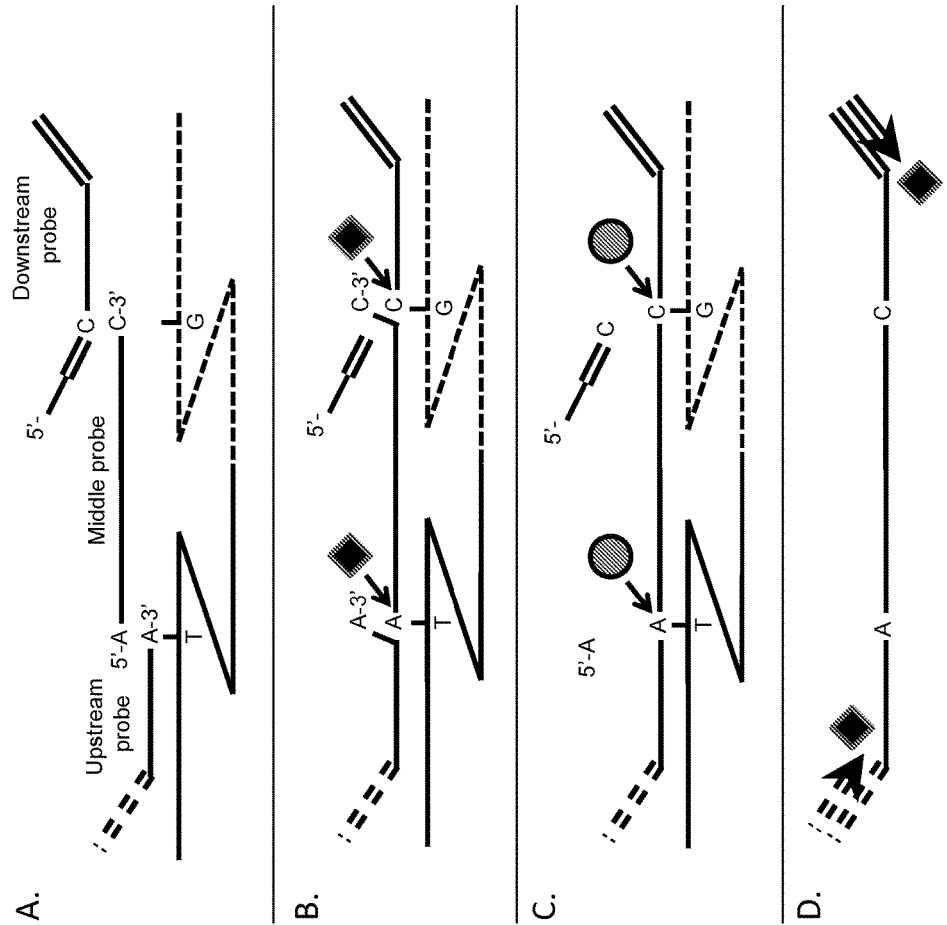
FIGS. 13A-13D show the nuclease digestion-ligation reaction process of the present invention to detect gene translocations in a target nucleic acid molecule where the precise translocation junction position is unknown. In this embodiment, three oligonucleotide probes are utilized, i.e., an upstream or first oligonucleotide probe, a middle oligonucleotide probe, and a downstream or second oligonucleotide probe. The first probe has an upstream target-specific portion with a ligation competent 3' OH that is overlapped by the immediately flanking 5' OH end of the middle oligonucleotide probe. The middle probe contains an upstream target-specific portion that is adjacent to the upstream target specific portion of the first probe. The middle probe also has a downstream target-specific portion with a ligation competent 3'OH that is overlapped by the immediately flanking 5'OH end of the second oligonucleotide probe. The second oligonucleotide probe contains a downstream target-specific portion that is adjacent to the downstream target-specific portion of the middle probe. In the absence of nuclease cleavage and ligation, unligated downstream probes form a hairpin and extend back on themselves to prevent target independent amplification and false positive signal generation. Ligase is shown as a circle; polymerase as a diamond.

FIGS. 13 and 14 depict the utilization of the nuclease-ligation reaction process of the present invention to detect gene translocation events in a target nucleic acid molecule where the precise junction position is unknown. This method can involve the use of three linear probes as depicted in FIGS. 13A-13D or first and second coupled probes in conjunction with a third (middle) probe as depicted in FIGS. 14A-14D. In either variation, the first probe (labeled as the "upstream probe" in FIGS. 13 and 14) contains a 5' primer-specific portion and an upstream gene target-specific portion at its 3' end. The 3' end of the first probe may be a ligation competent end or contain a cleavable blocking group (e.g., 3'SpC3, 3'ddC, or 3' phosphate). Cleavage of the 3' blocking group of the first oligonucleotide probe, e.g., using RNaseH (at an internal ribonucleotide base) or Tth Endo IV or *E. coli* Endo IV (at an internal abasic site), liberates a ligation competent 3' end.

The ligation competent 3' end of the first probe is overlapped by the flanking 5' end of the middle probe that also contains an upstream gene target-specific portion, when the first and middle oligonucleotide probes hybridize at adjacent positions on the upstream gene target nucleotide sequence (FIGS. 13A and 14A). The middle probe also contains a downstream gene target-specific portion at its 3' end. The ligation competent 3' end of the middle probe is overlapped by the flanking 5' end of the second oligonucleotide probe that also contains a downstream gene target specific portion, when the middle and second oligonucleotide probes hybridize at adjacent positions on the downstream gene target nucleotide sequence (FIGS. 13A and 14A). The second probe (labeled as the "downstream" probe in FIGS. 13 and 14), also contains a 5' primer-specific portion. In some embodiments, the first or middle probes may be polymerase extended at their 3' end so that the 3' most base of the first or middle probe is immediately overlapped by the 5' end residue of the middle or second probe, respectively.

The 5' nuclease activity of polymerase cleaves the overlapping flap nucleotide on the 5' end of the middle probe when it is the same nucleotide as the terminating 3' nucleotide on the first probe, and cleaves the overlapping flap nucleotide on the 5' end of the second probe when it is the same nucleotide as the terminating 3' nucleotide on the middle probe (Step 2, FIGS. 13B and 14B). Nuclease cleavage of the middle and second probes generates ligation competent 5'ends on each probe. Since the first and middle probes hybridize adjacent to one another, a ligase seals the ligation junction (Step 3, FIGS. 13C and 14C). Likewise, a ligase seals the junction between the adjacently hybridized middle and second probes (Step 3, FIGS. 13C and 14C).

The linear ligation product of FIG. 13D and circular ligation product of FIG. 14D are suitable for PCR amplification (Step 4) to generate extension products that are suitable for detection, thereby identifying the presence of a gene translocation within a target nucleic acid molecule of a sample.

To reduce target independent false positive signal arising from unligated probes during the nuclease-ligation reaction process the downstream probe in FIG. 13 and coupled probe in FIG. 14 can be designed such that, in the absence of ligation, they form hairpins at lower temperature and extend on themselves to form products that do not amplify and are not detected. Alternatively, when forming circular ligation products, an exonuclease digestion step following ligation will remove unligated probes and target from the reaction process.

Figures 15A, 15B, 15C, 15D:
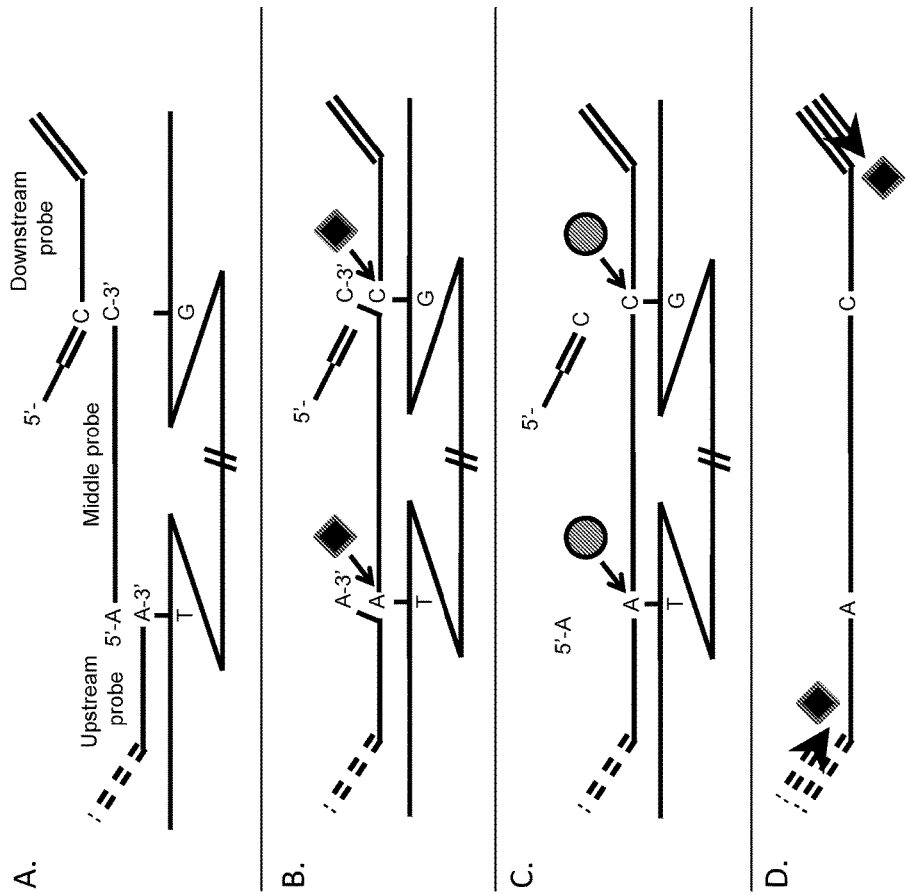
FIGS. 15A-15D show the nuclease digestion-ligation reaction process of the present invention to detect distant single nucleotide polymorphisms (SNPs) or alternative splicing events in a target nucleic acid molecule. In this embodiment, three oligonucleotide probes are utilized, i.e., an upstream or first oligonucleotide probe, a middle oligonucleotide probe, and a downstream or second oligonucleotide probe. The first probe has an upstream target-specific portion with a ligation competent 3' OH that is overlapped by the immediately flanking 5' OH end of the middle oligonucleotide probe. The middle probe contains an upstream target-specific portion that is adjacent to the upstream target specific portion of the first probe. The middle probe also has a downstream target-specific portion with a ligation competent 3'OH that is overlapped by the immediately flanking 5'OH end of the second oligonucleotide probe. The second oligonucleotide probe contains a downstream target-specific portion that is adjacent to the downstream target-specific portion of the middle probe. In the absence of nuclease cleavage and ligation, unligated downstream probes form a hairpin and extend back on themselves to prevent target independent amplification and a false positive signal generation. Ligase is shown as a circle; polymerase as a diamond; undefined distance between distant SNPs in target nucleic acid molecule indicated by "//".
Figures 16A, 16B, 16C, 16D:
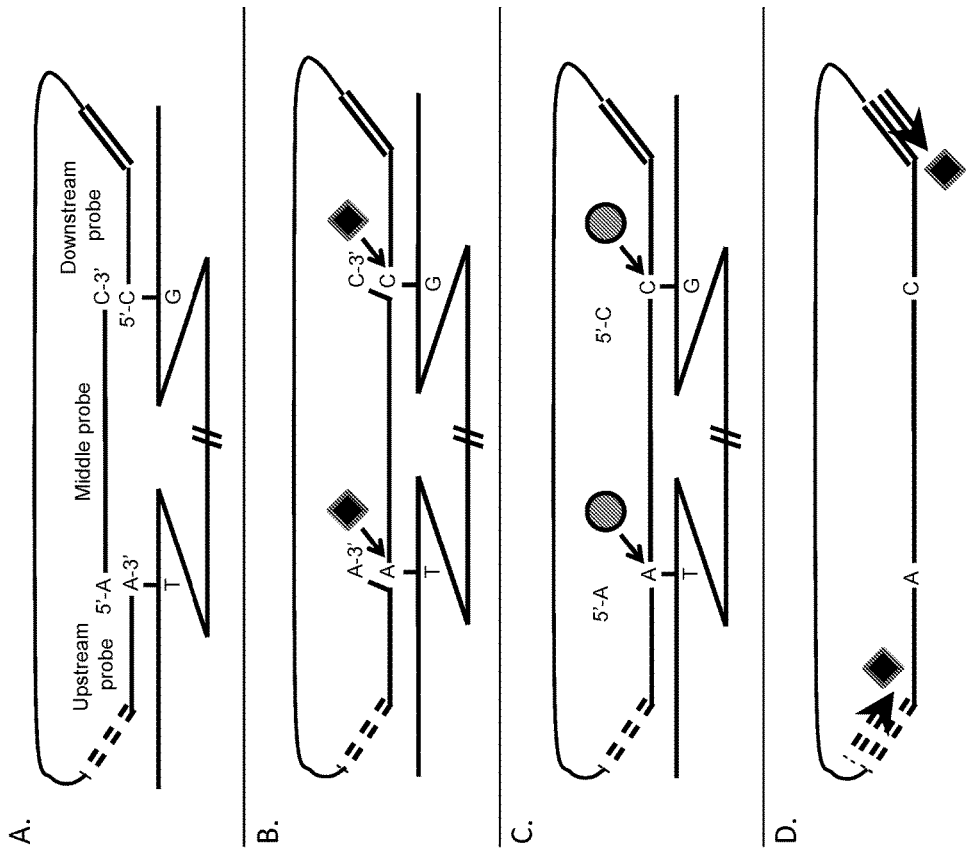
FIGS. 16A-16D show a variation of the nuclease digestion-ligation reaction process of the present invention depicted in FIG. 15 to detect distant single nucleotide polymorphisms (SNPs) or alternative splicing events in a target nucleic acid molecule. In this embodiment, the upstream first and downstream second oligonucleotide probes are coupled and utilized in conjunction with a middle probe. As described in reference to FIG. 15, the first and middle probes have ligation competent 3'OH ends that are overlapped by the immediately flanking 5'OH ends of the middle and second probes, respectively. In the absence of restriction enzyme digestion and/or ligation, unligated probes are subject to exonuclease digestion to prevent target independent amplification and a false positive signal generation Ligase is shown as a circle; polymerase as a diamond; undefined distance between distant SNPs in target nucleic acid molecule indicated by "//"

FIGS. 15 and 16 depict the utilization of the nuclease-ligation reaction process of the present invention to detect distant SNPs or alternative splicing events in a target nucleic acid molecule, e.g., DNA or mRNA target nucleic acid molecules. This method can involve the use of three linear probes as depicted in FIGS. 15A-15D or first and second coupled probes used in conjunction with a third/middle probe as depicted in FIGS. 16A-16D. In either variation, the first probe ("upstream probe") contains a 5' primer-specific portion and an upstream gene target-specific portion at its 3' end. The 3' end of the first probe may be a ligation competent end or contain a cleavable blocking group (e.g., 3'SpC3, 3'ddC, or 3' phosphate). Cleavage of the 3' blocking group of the first oligonucleotide probe, e.g., using RNaseH (at an internal ribonucleotide base) or Tth Endo IV or *E. coli* Endo IV (at an internal abasic site), liberates a ligation competent 3' end.

The ligation competent 3' end of the first probe is overlapped by the immediate flanking 5' end of the middle probe that also contains an upstream gene target-specific portion, when the first and middle oligonucleotide probes hybridize at adjacent positions on the upstream gene target nucleotide sequence (FIGS. 15A and 16A). The middle probe also contains a downstream gene target-specific portion at its 3' end. The ligation competent 3' end of the middle probe is overlapped by the immediate flanking 5' end of the second oligonucleotide probe that also contains a downstream gene target specific portion, when the middle and second oligonucleotide probes hybridize at adjacent positions on the downstream gene target nucleotide sequence (FIGS. 15A and 16A). The second probe ("downstream probe") also contains a 5' primer-specific portion. In some embodiments, the first or middle probes may be polymerase extended at their 3' end so that the 3' most base of the first or middle probe is immediately overlapped by the 5' end residue of the middle or second probe, respectively.

The 5' nuclease activity of polymerase cleaves the overlapping flap nucleotide on the 5' end of the middle probe when it is the same nucleotide as the terminating 3' nucleotide on the first probe, and cleaves the overlapping flap nucleotide on the 5' end of the second probe when it is the same nucleotide as the terminating 3' nucleotide on the middle probe (Step 2, FIGS. 15B and 16B). Nuclease cleavage of the middle and second probes generates ligation competent 5'ends on each probe. Since the first and middle probes hybridize adjacent to one another, a ligase seals the ligation junction (Step 3, FIGS. 15C and 16C). Likewise, a ligase seals the junction between the adjacently hybridized middle and second probes (Step 3, FIGS. 15C and 16C).

The linear ligation product of FIG. 15D and circular ligation product of FIG. 15D are suitable for PCR amplification (Step 4) to generate extension products that are suitable for detection, thereby identifying the presence of a distant SNPs or an alternative splicing event within a target nucleic acid molecules of a sample.

To reduce target independent false positive signal arising from unligated probes during the nuclease-ligation reaction process the downstream probe in FIG. 15 and coupled probe in FIG. 16 can be designed such that, in the absence of ligation, they form hairpins at lower temperature and extend on themselves to form products that do not amplify and are not detected as described supra. Alternatively, when forming circular ligation products, an exonuclease digestion step following ligation can be used to remove unligated probes and target from the reaction process.

Figures 17A, 17B, 17C, 17D, 17E:
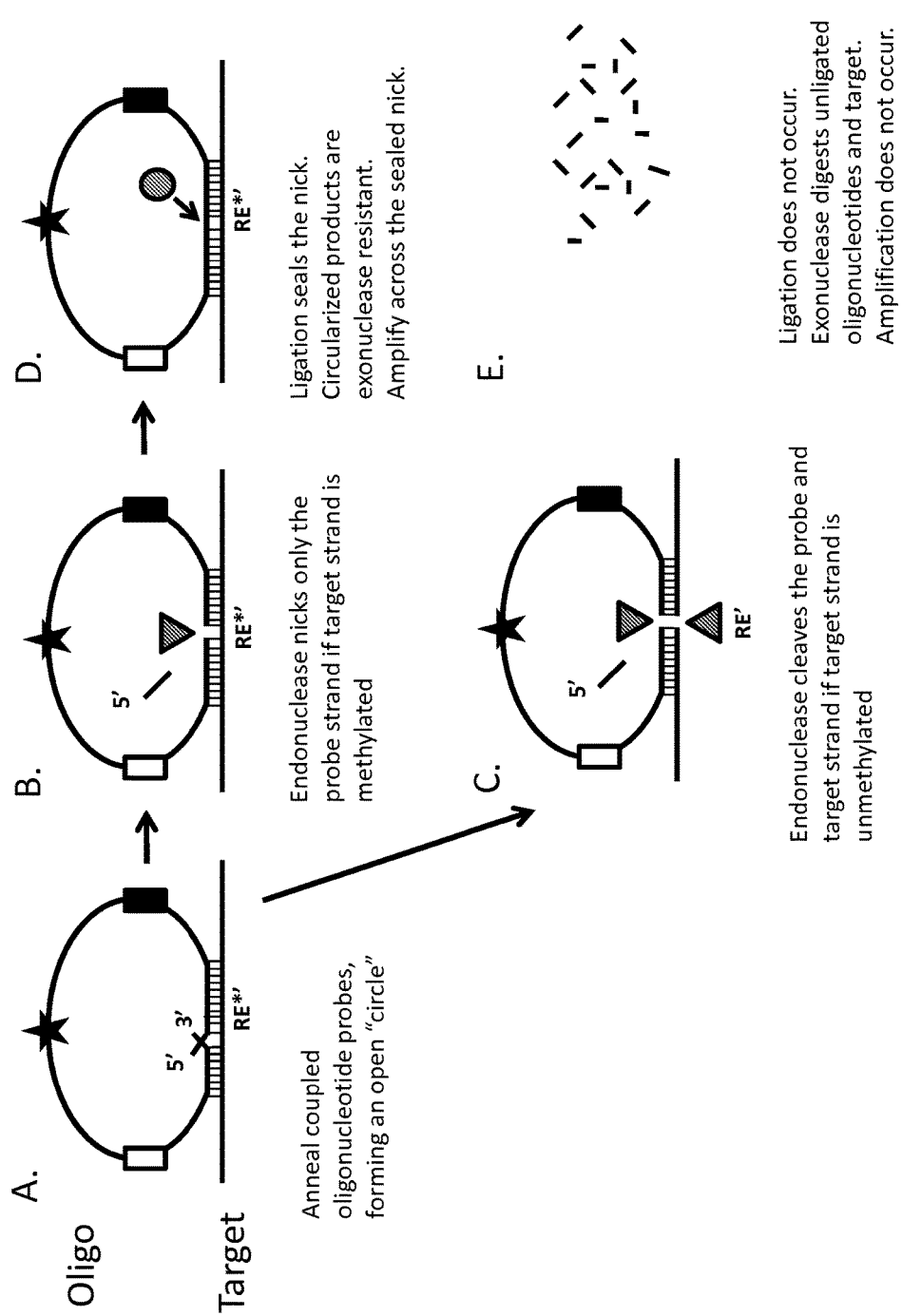
FIGS. 17A-17E show the restriction enzyme digestion-ligation process of the present invention using a coupled oligonucleotide probe design (i.e., a circularizable probe).

As depicted in FIGS. 3, 6, 8, 10, 12, and 16 the oligonucleotide probes of a probe set suitable for carrying out the nuclease-ligation or restriction enzyme digestion-ligation reaction processes may be tethered together to form a coupled probe or circular probe. In accordance with this embodiment, the 5' end of the first oligonucleotide probe (also referred to herein as upstream probe) is coupled to the 3' end of the second oligonucleotide probe (also referred to herein as downstream probe). Following hybridization of the target-specific portions of the coupled probe to its target nucleic acid molecule, and nuclease or restriction enzyme cleavage, the coupled probe is ligated to form a circular ligated product sequence. FIGS. 17A-17E show the restriction enzyme digestion-ligation process of the present invention using a coupled oligonucleotide probe design (i.e., a circularizable probe). A coupled oligonucleotide probe bearing an unmethylated methylation sensitive recognition sequence anneals to a complementary target nucleic acid molecule (FIG. 17A). The methylation sensitive restriction enzyme cleaves the recognition sequence of only the oligonucleotide probe if the hybridized target nucleic acid molecule is methylated (FIG. 17B), but will cleave both the probe and hybridized target nucleic acid molecule if the target nucleic acid is unmethylated (FIG. 17C). Following cleavage of the oligonucleotide probe when the target nucleic acid molecule is methylated, ligation seals 3' end of circular probe to the 5' end of the circular probe forming an exonuclease resistant product (FIG. 17D). Non-ligated uncircularized oligonucleotide probes can be digested using, e.g., exonucleases I and III (FIG. 17E). Optionally, the oligonucleotide probes can be internally cleaved at a scission domain (Star symbol), e.g., a dU tract targeted by UNG+heat=labile abasic phosphodiester stretch. Open and shaded rectangles of the circular probe represent universal PCR primer sites for PCR amplification of ligation product.

The coupled probes of the present invention can be designed to include all of the features described herein for the non-coupled probes, e.g., upstream/downstream primer regions, zip-code portions, UniTaq detection portions and primer portions, tag portions, etc.

The coupled probes may also contain design features that facilitate linearization of a circularized ligation product prior to PCR amplification or facilitate the formation of linearized extension products. Theses features are designed to prevent extension product destruction by a polymerase containing 5'→3' exonuclease during PCR amplification of a circularized ligation product. One such design feature is the inclusion of a spacer sequence or chemical link in the coupled probe that blocks polymerase extension through that region, i.e., a polymerase blocker, thereby preventing replication of the whole circularized ligated product and allowing the formation of linearized extension products. In another embodiment, the coupled probe is designed to contain a sequence that is subject to cleavage after ligation as described in reference to FIG. 17, e.g., a uracil base that is subject to cleavage by a uracil DNA glycosylase, and, optionally AP endonuclease, to linearize a circularized ligation product prior to amplification. Prior to cleavage of the circularized ligation product, unligated coupled probes (as well as input template DNA) are removed by exonuclease digestion. The above noted problem of extension product destruction may also be solved by using, when possible, a polymerase lacking the 5'→3' exonuclease activity during the initial universal primer amplification step, or by using secondary oligonucleotide primers complementary to the circular ligation product that contain modifications on the 5' end to render them refractory to the 5'→3' exonuclease activity of polymerase. Such 5' modifications include use of thiophosphate in the backbone linkage and/or use of 2'-O-methyl nucleotide analogues.

As already described supra, the coupled oligonucleotide probes may also contain complementary segments to facilitate hairpin formation of unligated probes prior to amplification of ligation products. To facilitate hairpin formation, the coupled oligonucleotide probe comprises a segment that is complementary to a portion of the 3' end of the probe. In the absence of ligation, the 3' end portion of the coupled probe hybridizes to the complementary segment to form a hairpinned coupled oligonucleotide probe. Extending the 3'end portion of the coupled hairpinned oligonucleotide probe during the first round of subsequent PCR forms an extended coupled hairpinned oligonucleotide probe that occludes binding of the second oligonucleotide primer to its complementary sequence. The advantage of this approach is that it removes unligated coupled probes from downstream amplification and detection processes without requiring any additional digestion (e.g., exonuclease digestion) steps.

Another aspect of the present invention is directed to a method for identifying, in a sample, one or more target nucleic acid molecules differing from other nucleic acid molecules in the sample by one or more methylated residues. This method involves providing a sample containing one or more target nucleic acid molecules potentially containing one or more methylated residues within one or more methylation sensitive restriction enzyme recognition sequences. One or more oligonucleotide probe sets are provided, each probe set comprising at least a first oligonucleotide probe comprising a target-specific portion configured to hybridize on the target nucleic acid molecule and containing (i) at least one methylation sensitive restriction enzyme recognition sequence, (ii) a 3' blocking group, hairpin, or flap region, and (iii) a 5' primer-specific portion. The sample is contacted with the one or more oligonucleotide probe sets under conditions effective for the at least first oligonucleotide probe of a probe set to hybridize in a base specific manner to a corresponding target nucleic acid molecule, if present in the sample, to form hybridization products. The method further involves blending at least one methylation sensitive restriction enzyme with the hybridization products to form a methylation sensitive restriction enzyme reaction mixture, and subjecting the methylation sensitive restriction enzyme reaction mixture to conditions suitable to cleave the at least first oligonucleotide probe of a hybridization product where the target nucleic acid molecule of said hybridization product contains one or more methylated residues within a methylation sensitive restriction enzyme recognition sequence. The cleavage liberates a 3'-OH on the at least first oligonucleotide probe of the hybridization product. The method further involves extending the liberated 3'OH of the cleaved at least first oligonucleotide probe of the hybridization product using a polymerase to form a hybridized extension product. One or more primary oligonucleotide primer sets are provided, each primer set comprising (i) a first primary oligonucleotide primer comprising a nucleotide sequence that is the same as a region of the target nucleic acid molecule sequence, wherein said region is 5' of the one or more methylation sensitive restriction enzyme recognition sequences of the target nucleic acid molecule, and a secondary primer-specific portion, and optionally, (ii) a second primary oligonucleotide primer comprising a nucleotide sequence that is the same as the 5' primer-specific portion of the at least first oligonucleotide probe in a probe set. The method further involves blending the hybridized extension products, the one or more primary oligonucleotide primer sets, and a polymerase to form a polymerase chain reaction mixture, and subjecting the polymerase chain reaction mixture to one or more polymerase chain reaction cycles comprising a denaturation treatment, a hybridization treatment, and an extension treatment thereby forming primary extension products. The primary extension products are detected and distinguished, thereby identifying the presence of one or more target nucleic acid molecules differing from other nucleic acid molecules in the sample by one or more methylated residues.

Figures 18A, 18B, 18C, 18D, 18E, 18F, 18G:
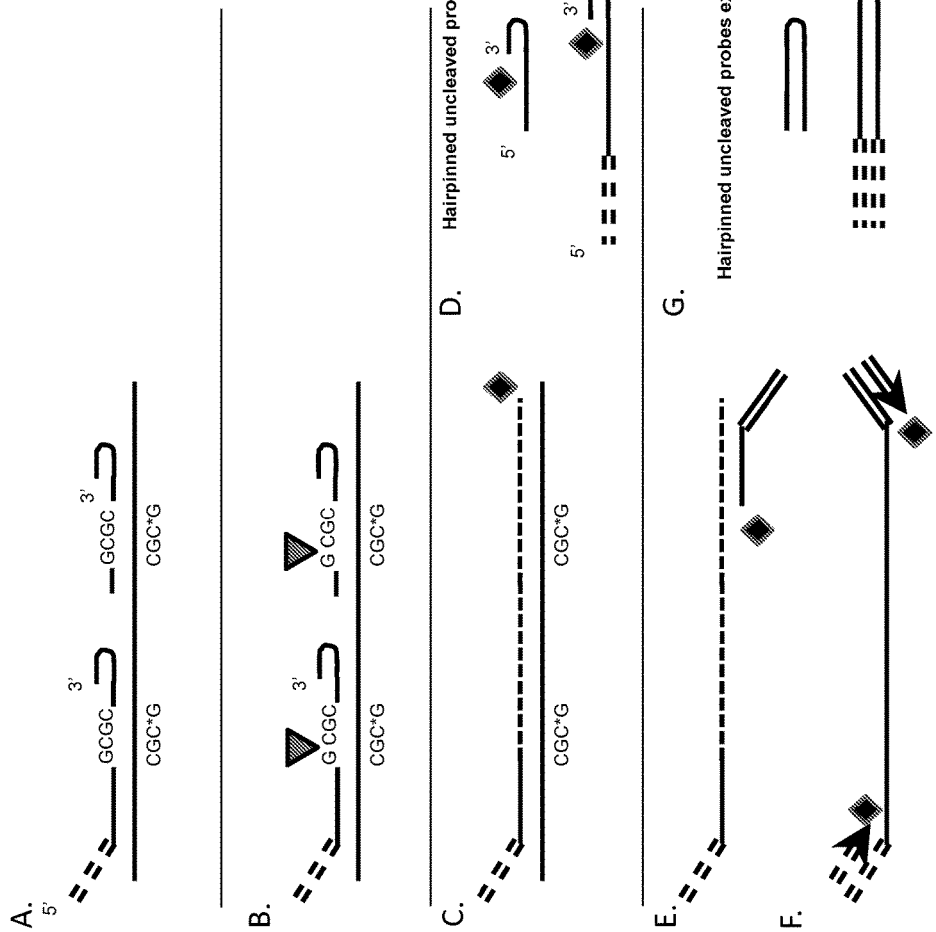

FIGS. 18A-18G and 18H-18M depict embodiments of this aspect of the present invention that are suitable for detecting methylation at adjacent HinP1I sites within a target nucleic acid molecule. Although not depicted, an initial HinP1I digestion of the DNA sample can be performed to enrich the sample for methylated HinP1I sites. As shown in FIGS. 18A and 18H, each probe set has at least a first oligonucleotide probe containing an unmethylated HinP1I methylation sensitive restriction enzyme recognition sequence, a 3' end that cannot be extended by polymerase, and a 5' primer-specific portion. Additional oligonucleotide probes, each containing an unmethylated HinP1I recognition sequence and a 3' end that cannot be extended by polymerase, can be employed to detect HinP1I methylation at adjacent downstream sites in the target nucleic acid molecule. The 3' end of the first oligonucleotide probe and any additional probes can have a 3' hairpin as shown in FIG. 18A, a blocking group as shown in FIG. 18H, a 3' flap region, or other feature suitable for preventing polymerase extension of the probe. Following hybridization of the oligonucleotide probe or probes to a complementary target nucleic acid molecule, HinP1I cleaves each oligonucleotide probe hybridized to a methylated target nucleic acid to generate an extension competent 3'OH (Step 3, FIGS. 18B and 18I). A polymerase extends the liberated 3' end of the first oligonucleotide probe to create a hybridized extension product (Step 4, FIGS. 18C and 18J). HinP1I cleavage of the resulting hybridized extension product can be prevented by incorporating a thermal inactivation step or by polymerase incorporation of modified nucleotides. Target nucleic acid molecules containing unmethylated residues at a HinP1I site that are hybridized to a first or additional oligonucleotide probe are cleaved by HinP1I (along with the hybridized probes), thereby preventing subsequent extension, amplification, and detection.

In Step 5 (FIGS. 18E and 18K), an oligonucleotide primer comprising a target-specific portion that is 5' of the methylation sensitive restriction enzyme recognition sequences and a 3' primer specific portion is added alone or together with another primer that is the same as the 5' primer specific portion of the first oligonucleotide probe to generate primary extension products having both 5' and 3' primer specific portions. As depicted in FIG. 18K, the target-specific oligonucleotide primer may contain a cleavable blocking group. For example the primer may contain a blocking group with a single ribonucleotide residue at the 3' end to prevent polymerase extension of the primer. Primer hybridization to only a complementary target-specific region forms a substrate for RNase H2, which cleaves the primer 5' to the ribonucleotide base thereby removing the blocking group and generating a 3'-OH on the primer that is capable of polymerase extension (FIGS. 18K and 18L) (see Dobosy et al., "RNase H-dependent PCR (rhPCR): Improved Specificity and Single Nucleotide Polymorphism Detection Using Blocked Cleavable Primers," *BMC Biotechnology* 11:80 (2011), which is hereby incorporated by reference in its entirety).

Primary extension products of methylated target nucleic acid molecules may be further amplified upon addition of oligonucleotide primers specific for the 5' and 3' primer portions of the primary extension products (FIGS. 18F and 18M).

As depicted in FIGS. 18D and 18G, uncleaved hairpinned oligonucleotide probes are extended by the polymerase during PCR amplification of the extension products, to occlude binding of, and subsequent extension or amplification, by the oligonucleotide primers in the PCR reaction.

Figures 19A, 19B, 19C, 19D, 19E, 19F, 19G:
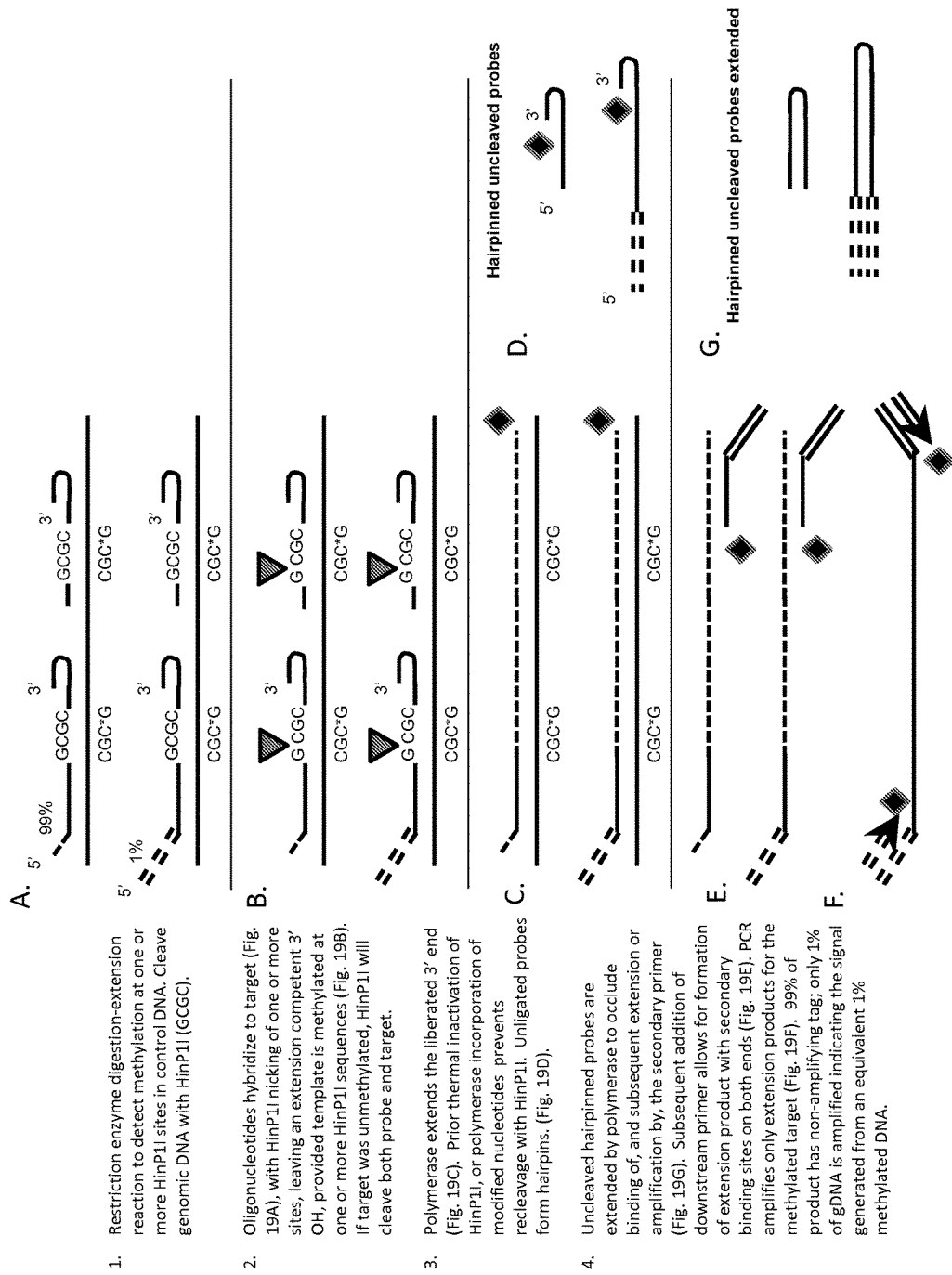
FIGS. 19A-19G depict how a known region of DNA can be used as a positive control in the same reaction mixtures shown in FIG. 18, to provide a control signal equivalent to the presence of 1% methylated DNA.

FIGS. 19A-19G demonstrate how a known region of a nucleic acid molecule can be used as a positive control in the same restriction enzyme digestion-extension reaction mixture shown in FIG. 18, to provide a control signal equivalent to the presence of 1% of methylated DNA. Two first oligonucleotide probes, each containing an unmethylated HinP1I site and a 3' hairpinned region or 3' blocking group are provided, where one of the first oligonucleotide probes contains a 5' primer-specific portion or other amplifying tag and the other first oligonucleotide probe does not contain the 5' primer-specific portion or contains a non-amplifying tag (FIG. 19A). The two first oligonucleotide probes are provided in a mixture in a known ratio, e.g. 1:99, respectively. Oligonucleotide probes are hybridized to the control DNA, HinP1I cleavage is carried out to generate extension competent 3' OH ends on the first oligonucleotide probes (Step 2, FIG. 19B). Polymerase extends the liberated 3' ends of the first oligonucleotide probes to create a hybridized extension product (Step 3, FIG. 19C). In Step 4, a downstream oligonucleotide primer comprising a target-specific portion and a 3' primer specific portion is added alone or together with an upstream primer that is the same as the 5' primer specific portion to generate primary extension products having both 5' and 3' primer specific portions (FIG. 19E). Since 99% of the hybridized extension products do not contain a 5' primer specific portion, only the 1% of hybridized extension products containing the 5' primer-specific portion will serve as template for the generation of primary extension products (Step 4, FIG. 19E). Primary extension products of methylated target nucleic acid molecules may be further amplified upon addition of oligonucleotide primers specific for the 5' and 3' primer portions of the primary extension products (Step 4, FIG. 19F). The signal generated from the control reaction is equivalent to the signal that would be generated from a methylated target nucleic acid molecule present in 1% of the DNA sample. Hairpinned uncleaved probes are polymerase extended during PCR amplification and occluded from further analysis (FIGS. 19D and 19G).

FIGS. 20A-20G and 20H-20M depict embodiments of this aspect of the present invention that are suitable for detecting methylation at adjacent BstU1 sites within a target nucleic acid molecule. Although not depicted, an initial BstU1 digestion of the DNA sample can be performed to enrich the sample for methylated BstU1 sites. As shown in FIGS. 20A and 20H, each probe set has at least a first oligonucleotide probe containing an unmethylated BstU1 methylation sensitive restriction enzyme recognition sequence, a non-extendable 3' end, and a 5' primer-specific portion. Additional oligonucleotide probes, each containing an unmethylated BstU1 recognition sequence and non-extendable 3' end, can be employed to detect BstU1 methylation at adjacent downstream sites in the target nucleic acid molecule. The non-extendable 3' end of the first and additional oligonucleotide probes of a probe set can have a 3' hairpin as shown in FIG. 20A, a blocking group as shown in FIG. 20H, a 3' flap region or any other feature suitable for preventing polymerase extension of the probe.

Following hybridization of the oligonucleotide probe or probes to a complementary target nucleic acid molecule, BstU1 cleaves each oligonucleotide probe that is hybridized to a methylated target nucleic acid to generate an extension competent 3'OH (Step 2, FIGS. 20B and 20I). A polymerase extends the liberated 3' end of the first oligonucleotide probe to create a hybridized extension product (Step 3, FIGS. 20C and 20J). Subsequent BstU1 cleavage of the resulting hybridized extension product can be prevented by polymerase incorporation of modified nucleotides. Target nucleic acid molecules containing unmethylated residues at a BstU1 site that is hybridized to a first or additional oligonucleotide probe are cleaved by BstU1 (along with the hybridized probe), thereby preventing subsequent extension, amplification, and detection.

In the next step, an oligonucleotide primer comprising a target-specific portion and a 3' primer specific portion is added alone or together with a primer that is the same as the 5' primer specific portion of the first oligonucleotide probe to generate primary extension products having both 5' and 3' primer specific portions (Step 4, FIG. 20E and Step 5, FIG. 20K). As described above and shown in FIG. 20K, the target-specific primer may contain a cleavable blocking group at its 3'end, e.g., a ribonucleotide residue cleavage site near the blocked 3'end of the primer. Upon primer hybridization to its complementary target-specific sequence, the blocking group is selectively cleaved, e.g., using RNase H to cleave at the ribonucleotide residue, to allow extension to occur (FIG. 20L). Primary extension products of methylated target nucleic acid molecules may be further amplified upon addition of oligonucleotide primers specific for the 5' and 3' primer portions of the primary extension products (FIGS. 20F and 20M).

As depicted in FIGS. 20D and 20G, uncleaved hairpinned oligonucleotide probes are extended by the polymerase during PCR amplification of the extension products, to occlude binding of, and subsequent extension or amplification, by the oligonucleotide primers in the PCR reaction.

The ligation products or primary extension products formed in accordance with the various methods of the present invention can be detected using a variety of detection methods known in the art. For example, the ligation or primary extension products can be detected by sequencing the products using methods well known in the art. Alternatively, the ligation or extension products can be separated by size and detected. To facilitate detection via sequencing or size separation, the oligonucleotide probes of a probe set may further comprise one or more detectable labels, primer-portions, or other detection portions. A number of suitable detection portions and methods of detections are illustrated in the accompanying figures and described in more detail below.

In one embodiment of the present invention, detection of the ligation products or primary extension products involves PCR amplification to generate primary extension products and secondary extension products, respectively. In accordance with this embodiment, the oligonucleotide probes of a probe set utilized in the FEN-ligation-restriction enzyme digestion process or restriction enzyme digestion-ligation process of the present invention comprise a first oligonucleotide probe having a 5' primer-specific portion and a second oligonucleotide probe having a 3' primer-specific portion as shown, for example, in FIGS. 1-11. The resulting linear or circularized ligation products comprise the 5' primer-specific portion, the target-specific portions, and the 3' primer-specific portion. Likewise, the primary extension products formed in the restriction enzyme digestion-extension process of the present invention also comprise a 5' primer-specific portion, a target-specific portion, and a 3' primer-specific portion as shown in FIGS. 18-20.

The primer-specific portions of the ligation products and primary extension products formed in accordance with the methods of the present invention can be universal primer sequences allowing for subsequent universal amplification of all of the ligation or primary extension products formed under a single set of conditions. This is particularly useful when detecting low abundance target nucleotide molecules. Accordingly, following product formation, a universal PCR amplification is performed to proportionally amplify all ligation products or primary extension products in the sample. Following universal PCR, the extension products of the original ligation products or secondary extension products are detected and quantified. Alternatively, the primer-specific portions can be specific for the target nucleotide sequence. In yet another embodiment, the primer-specific portions of the ligation products or primary extension products may comprise universal primer-specific portions in combination with one or more target-specific primer-specific portions.

To facilitate PCR amplification of the ligation products or primary extension products generated using the methods of the present invention, one or a plurality of oligonucleotide primer sets are provided. Each primer set has a first oligonucleotide primer containing the same sequence as the 5' primer-specific portion of the ligation product or primary extension product, and a second oligonucleotide primer complementary to the 3' primer-specific portion of the ligation product or primary extension product. The ligation products or primary extension products are blended with the one or a plurality of oligonucleotide primer sets and the polymerase to form a polymerase chain reaction mixture. The polymerase chain reaction mixture is subjected to one or more polymerase chain reaction cycles which include a denaturation treatment, a hybridization treatment, and an extension treatment. During the denaturation treatment, hybridized nucleic acid sequences are separated. The hybridization treatment causes primers to hybridize to their complementary primer-specific portions of the product sequence. During the extension treatment, hybridized primers are extended to form extension products complementary to the sequences to which the primers are hybridized.

In almost all cases, it is desirable to occlude unligated or uncleaved oligonucleotide probes from the sample containing ligation products or primary extension products prior to PCR amplification to prevent unligated or uncleaved probe extension and/or amplification that may generate false positive signals. Several means for achieving this objective are described below.

Figure 21:
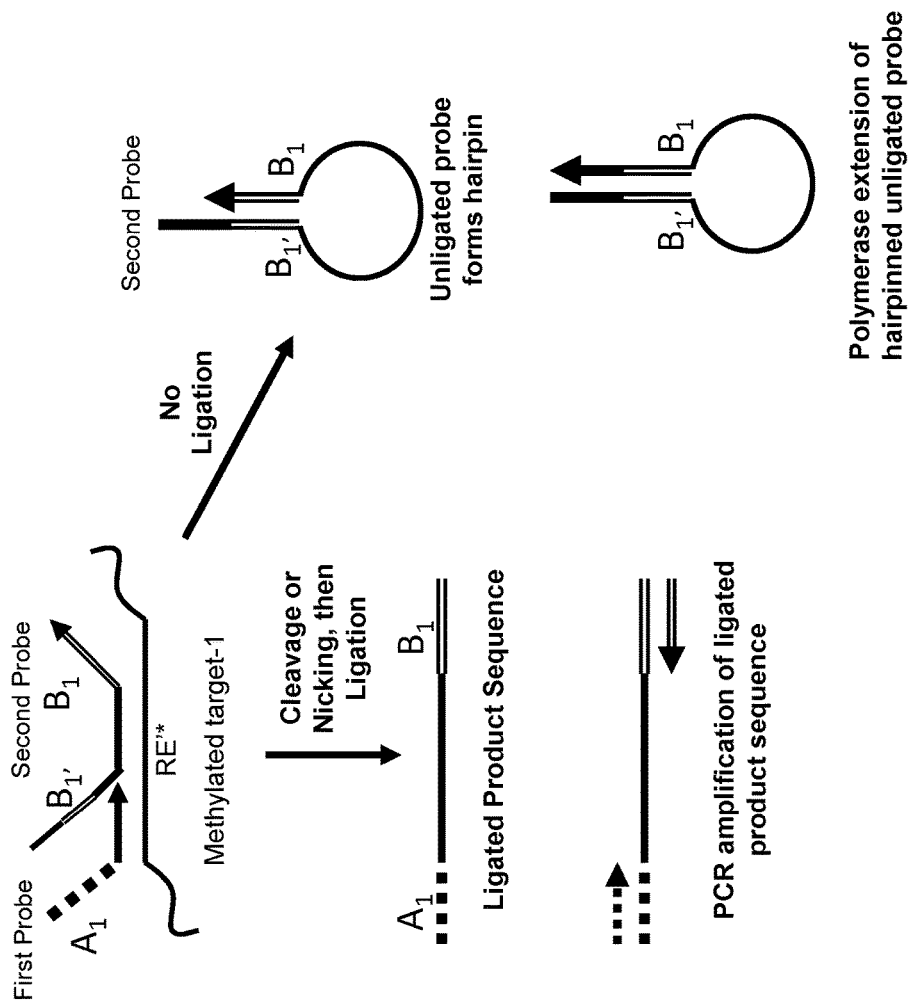
FIG. 21 is a schematic showing an oligonucleotide probe design that facilitates separation of unligated oligonucleotide probes from ligation products to occlude extension or amplification of the unligated oligonucleotide probe in the amplification phase following ligation. In this design, the second oligonucleotide probe had complementary tags $B_1$ and $B_1'$. During the restriction enzyme digestion-ligation process, second oligonucleotide probes do not form significant hairpins because the annealing temperature of the probe to target nucleic acid molecule is set too high to permit a stable intramolecular stem formation between $B_1$ and $B_1'$. Following ligation, the temperature is decreased permitting unligated second oligonucleotide probes to undergo an intramolecular annealing between $B_1$ and $B_1'$. The 3' end of unligated hairpinned second oligonucleotide ($B_1$) is extended forming a highly thermodynamically stable stem. The panhandle oligonucleotide is no longer able to participate in PCR primer extension.

In one approach, unligated oligonucleotide probes are occluded from subsequent extension and amplification by designing probes that are capable of forming stable hairpin structures in the absence of ligation. This embodiment is depicted in FIG. 21, and also shown in the processes of FIGS. 2-3 and 5-11. In accordance with this embodiment and in reference to FIG. 21, the second oligonucleotide probe further comprises a nucleotide flap that is 5' to the overlapping identical nucleotide at the junction, wherein at least a portion of the nucleotide flap ($B_1'$ in FIG. 21) is complementary to at least a portion of the 3' primer-specific portion of the second oligonucleotide probe ($B_1$ in FIG. 21). In the absence of ligation, complementary regions of the nucleotide flap ($B_1'$) and the 3' primer-specific portion ($B_1$) of unligated second oligonucleotide probes hybridize to each other to form hairpinned second oligonucleotide probes (FIG. 21, right-hand side). The 3' primer-specific portion ($B_1$) of the hairpinned second oligonucleotide probe is extended during the first PCR cycle to form an extended hairpinned second oligonucleotide probe that occludes binding of the second oligonucleotide primer to its complementary sequence. As shown in the left-hand side of FIG. 21, ligation products that are formed are subsequently amplified using PCR without interference from the unligated probes.

This same approach can also be utilized to occlude uncleaved oligonucleotide probes utilized in the restriction enzyme digestion-extension reaction process of the present invention. Accordingly, the first oligonucleotide probe is designed to further comprise a 3' nucleotide flap that is 3' to the target specific portion. At least a portion of the 3' nucleotide flap is complementary to at least a portion of the 5' primer specific portion of the first oligonucleotide probe. In the absence of probe cleavage by a methylation sensitive restriction enzyme, complementary regions of 3' nucleotide flap and the 5' primer specific portion hybridize to each other to form hairpinned first oligonucleotide probes.

In another approach, uncleaved and unligated oligonucleotide probes may be occluded from subsequent extension and amplification by designing probes that have a non-extendable 3' end. Suitable probe designs include a 3' sequence that is capable of forming a stable hairpin structures as shown in FIGS. 18A-18G and FIGS. 20A-20G. Alternatively, the oligonucleotide probe may be designed to contain a 3' blocking group that block polymerase mediated extension, e.g., a phosphorothioate group (Nikiforow, et al., "The Use of Phosphorothioate Primers and Exonuclease Hydrolysis for the Preparation of Single-stranded PCR Products and their Detection by Solid-phase Hybridization," *PCR Methods and Applications*, 3:p. 285-291 (1994), which is hereby incorporated by reference), as shown in FIGS. 18H-18M and FIGS. 20H-20M.

Figures 22A, 22B:
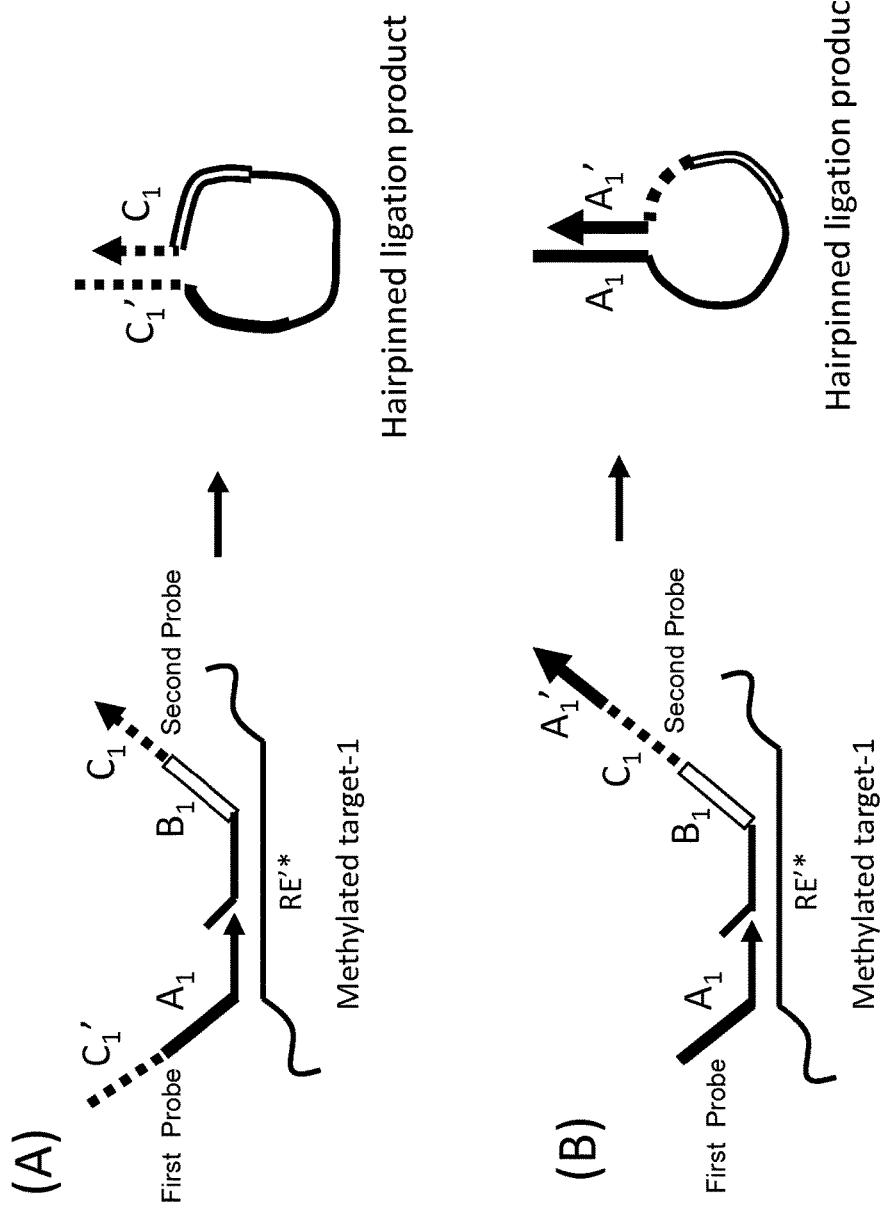
FIGS. 22A-22C are schematics showing various oligonucleotide probe designs that facilitate separation of ligation products from unligated oligonucleotide probes.

Another approach for removing unligated probe sequences from a sample following the ligation process involves an exonuclease digestion step prior to amplification (L-H Guo and R. Wu, *Methods in Enzymology* 100:60-96 (1985), which is hereby incorporated by reference). To incorporate exonuclease digestion, the ligation products need to be protected from digestion. In one approach, the first and second oligonucleotide probes of a probe set comprise complementary first and second tag portions, respectively. The first and second tag portions of an oligonucleotide probe set can, but do not have to, differ in sequence from the tag portions of other oligonucleotide probe sets. FIG. 22A shows an example where the first oligonucleotide probe contains the tag portion C1' and the second oligonucleotide probe contains the tag portion C1, where C1' and C1 are complementary to each other. After ligation of the first and second oligonucleotide probes of a probe set, the first and second tag portions, i.e., C1' and C1, hybridize to form a hairpinned ligated product sequence that is resistant to exonuclease digestion ($A_1$ and $B_1$ in this schematic represent primer-specific portions for downstream polymerase chain reaction). Subsequent exonuclease digestion removes unligated probes. In addition, non-specifically ligated molecules, which bear mismatched tags, remain wholly or partially single-stranded and are also digested. Following exonuclease digestion, the hairpinned ligation products are denatured and PCR amplification is performed using oligonucleotide primer sets having a first primer that is complementary to the 3' primer specific portion of the ligation product (i.e., $B_1$) and a second primer that has the same nucleotide sequence as the 5' primer specific portion of the ligation product (i.e., $A_1$).

FIG. 22B shows an alternative oligonucleotide probe design where the second oligonucleotide probe contains a region ($A_1'$) that is complementary to the 5' primer specific portion of the first oligonucleotide probe ($A_1$). After ligation of the first and second oligonucleotide probes of this probe set, $A_1$ and $A_1'$ hybridize to form a hairpinned ligation product. Again, unligated oligonucleotide probes and non-specifically ligated molecules, which bear mismatched tags, remain wholly or partially single-stranded, and are subsequently digested using a single-strand specific exonuclease enzyme, e.g. ExoI. As noted above for FIG. 22A, following exonuclease digestion, the hairpinned ligation products are denatured and oligonucleotides primers and a polymerase are added to amplify the denatured ligation products in the absence of any unligated probes.

In an alternative embodiment, the oligonucleotide probes of a probe set may comprise blocking moieties at their ends not involved in ligation. Suitable blocking moieties include a detectable label or a phosphorothioate group (Nikiforow, et al., "The Use of Phosphorothioate Primers and Exonuclease Hydrolysis for the Preparation of Single-stranded PCR Products and their Detection by Solid-phase Hybridization," *PCR Methods and Applications*, 3:p. 285-291 (1994), which is hereby incorporated by reference). After the ligation process, unligated probes are selectively destroyed by incubation of the reaction mixture with the exonuclease, while ligated probes are protected due to the elimination of free 3' ends which are required for initiation of the exonuclease reaction.

Figure 22C:
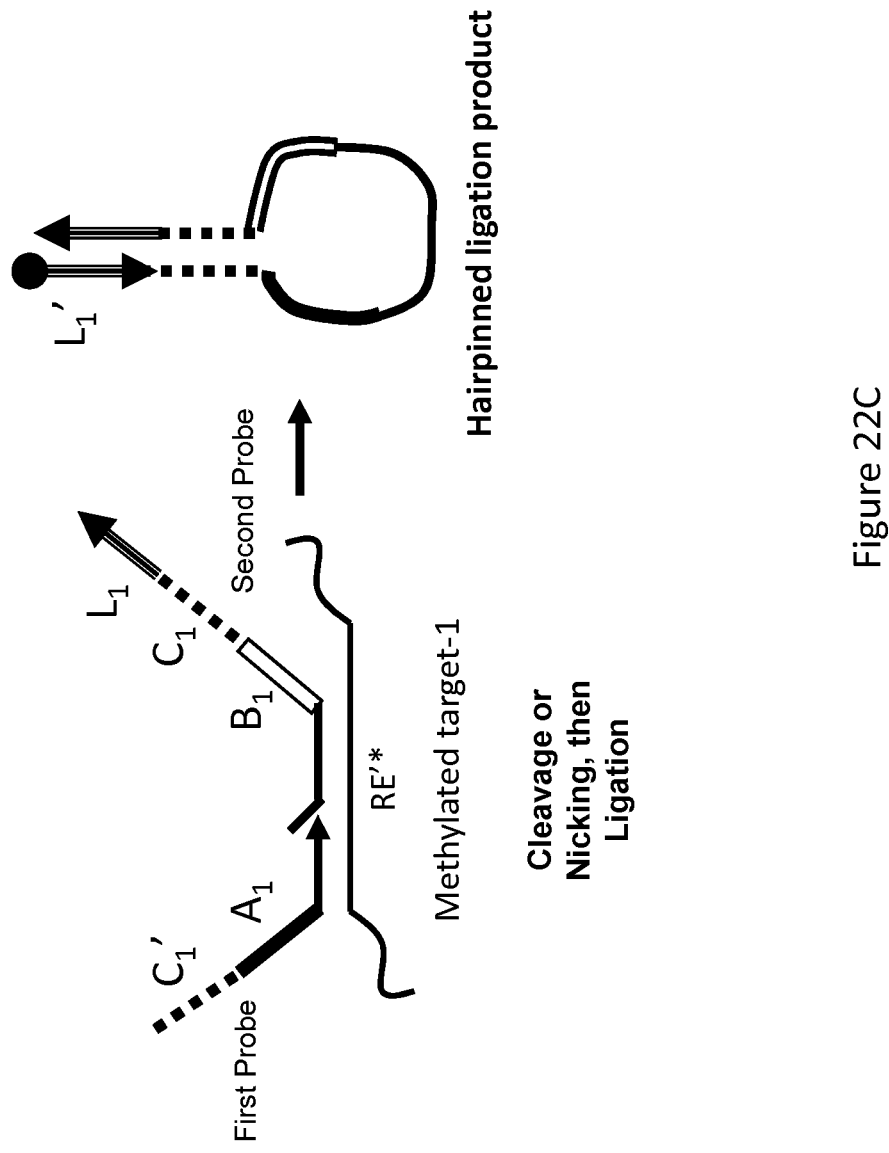

FIG. 22C shows another approach for separating ligation products from unligated oligonucleotide probes that relies on selection of ligation products. In this embodiment, the first and second oligonucleotide probes bear allele specific complementary tags, $C_1$ and $C_1'$, and additionally, the second oligonucleotide probe has a universal tag $L_1$. After ligation, a hairpin forms upon hybridization of $C_1$ and $C_1'$, this hairpin having a protruding L1 at its end. A universal biotinylated (●) oligonucleotide ($L_1'$) is ligated to the hairpinned product in the same reaction permitting separation of biotin-bearing ligation products from unligated oligonucleotide probes by streptavidin selection. The oligonucleotide probes can also be made sufficiently long, e.g., by including so called spacers between tags (C1/C1') and the primer-specific portions of the oligonucleotides (A1/B1) so that ligation of the biotinylated oligonucleotide occurs while portions of the oligonucleotide probes are annealed to the target. Alternatively, one can increase the temperature to melt the ligated product off the target, and then lower the temperature to enable hairpin formation of the product and ligation of the biotinylated oligonucleotide to the hairpinned product. In either event, the separated ligation products are subsequently amplified in the presence of a polymerase and oligonucleotide primers as described above.

The key feature for the oligonucleotide probe designs shown in FIGS. 22A-22C to work is that the intramolecular hairpins are thermodynamically much more stable than bimolecular interactions between oligonucleotide probes. Temperature and buffers are selected so that a very small percentage of unligated oligonucleotide probes with complementary tags and will be annealed to each other, but close to 100% of ligated molecules will form a hairpin structure.

In another embodiment of the present invention, unligated or uncleaved oligonucleotide probes can be removed using gel filtration (e.g., Sephadex) or a similar method to separate longer, higher molecular weight ligated products from shorter unligated oligonucleotide probes.

In another embodiment of the present invention, the ligation products or primary extension products are detected using next generation sequencing methods. In accordance with this embodiment, oligonucleotide probes of a probe set further comprise the appropriate sequencing tags or adaptors required for the ILLUMINA® MISEQ® or HISEQ® (San Diego, Calif.) next generation sequencing platform, the LIFE TECHNOLOGIES™ ION TORRENT™ (Life Technologies, Carlsbad, Calif.) next generation sequencing platform, the ROCHE™ 454 next generation sequencing platform, or other next generation sequencing platform (i.e., pyrosequencing, fluorescence-based sequencing-by-synthesis, fluorescence-based sequencing-by-ligation, ion-based sequencing-by-synthesis, and ion-based sequencing-by-ligation), which are all well known in the art. There is no need to have different tags for different chromosomes, as sequences themselves can be unambiguously mapped to one of the chromosomes in the human genome.

Several means of detecting PCR amplified ligation products or primary extension products can be employed as described below.

In a first approach, one of the primers in an oligonucleotide primer set used for PCR amplification of the ligation products or primary extension products further comprise a detectable label to create labeled extension products that can be detected and identified. This method of detection is suitable when the primer-specific portions of the ligation product or primary extension products are target specific. U.S. Pat. Nos. 6,027,889, 6,797,470, 7,312,039, 7,320,865, 7,332,285, 7,166,434, 7,429,453, 8,283,121 all to Barany, which are hereby incorporated by reference in their entirety, describe methods of detecting nucleic acid sequence difference using a coupled ligation detection and polymerase chain reactions. A wide variety detectable labels are known in the art. Fluorescent dyes are particularly suitable for detecting and quantitating PCR products. Suitable fluorescent dyes include, without limitation, FAM™ fluorescent dye, TET™ fluorescent dye, JOE™ fluorescent dye, VIC® fluorescent dye, HEX™ fluorescent dye, CY3™ fluorescent dye, TAMRA™ fluorescent dye, TexasRed® fluorescent dye, CY5™ fluorescent dye, and ROX™ fluorescent dye.

In another embodiment of the present invention, detection of the PCR amplified ligation products or primary extension products is facilitated by a zip-code portion. In accordance with this embodiment, the first and/or the second oligonucleotide probe of a probe set further comprises a zip-code portion. As used herein, a zip-code is a short nucleotide sequence, e.g., between 16 to 24 nucleotides in length, that has no sequence identity to the target nucleotide sequence, and preferably, little or no sequence identify to any genomic nucleotide sequence. In a collection of zip-codes, each zip-code differs in sequence from the sequence of other zip-codes in the collection by at least 25%, yet all zip-codes of a collection are designed to have similar melting temperatures to facilitate hybridization to complementary capture oligonucleotides under uniform hybridization conditions with little or no non-specific hybridization to non-capture oligonucleotide sequences. In one embodiment of the present invention, the zip-code portion is used to identify and distinguish different ligation products or primary extension products in a sample, therefore the zip-code portion for each different product has a different nucleotide sequence. In an alternative embodiment, where the goal is to simply detect the presence or absence of one or more methylated or unmethylated residues in a particular genomic region, but the identity of the particular methylated or unmethylated residues within that region are not critical, the same zip-code portion may be used to detect different products. In either embodiment, incorporation of zip-codes into the oligonucleotide probes of a probe set allows for highly multiplexed detection of various target sequences simultaneously.

Methods of designing collections of zip-code sequences and their complementary capture oligonucleotides sequences are described in detail in U.S. Pat. Nos. 6,852, 487, 7,455,965, and 6,506,594 all to Barany et al., which are hereby incorporated by reference in their entirety.

Figures 23A, 23B, 23C:
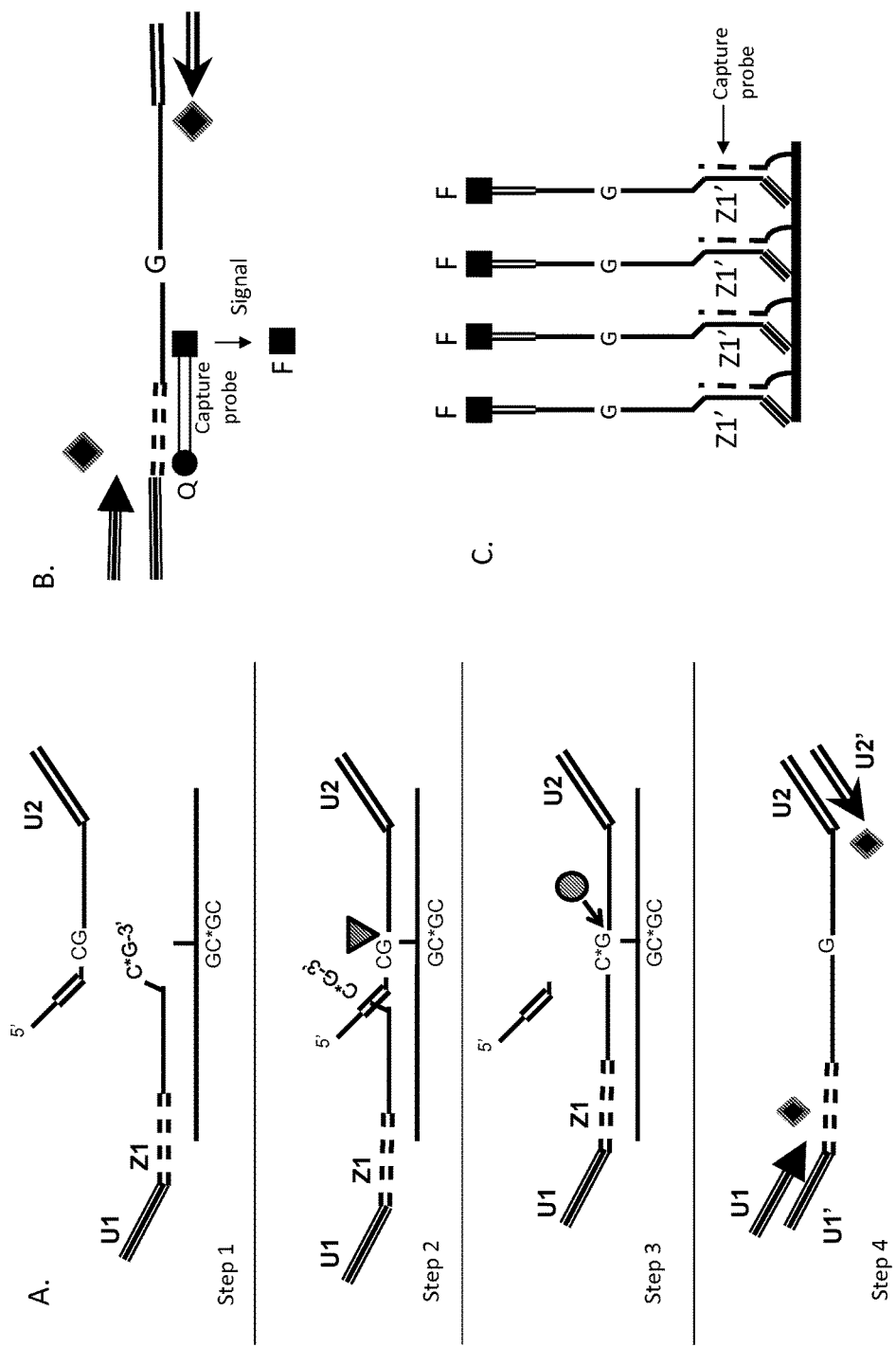
FIGS. 23A-23C show an example of the restriction enzyme digestion-ligation-PCR process of the present invention where detection of the resulting products is facilitated by a zipcode sequence.

Detection using the zipcode can be carried out using traditional Taqman™ detection as shown in FIG. 23B (see U.S. Pat. No. 6,270,967 to Whitcombe et al., and U.S. Pat. No. 7,601,821 to Anderson et al., which are hereby incorporated by reference in their entirety). For detection using Taqman assays, the first or second oligonucleotide probe contains a zip-code sequence. FIG. 23A illustrates the incorporation of a zip-code sequence into the restriction enzyme digestion-ligation reaction process of the present invention. As shown in FIG. 23A, the ligation product generated in this process (Step 3) contains the 5' primer specific portion (U1), the zip-code portion (Z1), target specific portions and the 3' primer specific portion (U2). Although not depicted, it is understood that the zip-code sequence can also be incorporated into the ligation products formed using the FEN-ligation-restriction enzyme digestion and restriction enzyme digestion-extension-ligation processes of the present invention, and the primary extension products formed using the restriction enzyme digestion-extension process of the present invention.

An optional first universal amplification reaction using universal PCR primers can be carried out to proportionately increase the ligation product in the sample (the universal PCR step is shown as Step 4 in FIG. 23A). This is particularly suitable when detecting low abundance target nucleic acid sequences. After about 8-20 cycles of universal amplification, the sample is diluted 10- to 100-fold and unique primers are added that overlap with some or all of the unique zipcode sequence for each product. The Taqman probe would be for either the junction sequence of both zipcode and target DNA (as shown in FIG. 23B), or just the target DNA. The second primer can be universal (U2) or, for added specificity, it can be designed to include some genome-specific bases (without overlap to the Taqman probe). Signal is generated by 5' nuclease activity of polymerase when it extends the second primer. Primer extension cleaves the detectable label from the capture oligonucleotide releasing the detectable label from the quencher molecule, enabling detection.

Alternatively, for detection using universal (zipcode) arrays as shown in FIG. 23C, the second oligonucleotide primer (U2') contains a reporter label, i.e. a fluorescent group, while the first oligonucleotide primer (U1) contains a 5' phosphate, and amplification would continue for a total of about 30 to 40 cycles. Lambda exonuclease digestion of the second strand renders the fluorescently labeled product single-stranded and suitable for hybridization to a universal (zipcode) array containing capture oligonucleotide probes that are complementary to the zipcode portions of the fluorescently labeled product as shown in FIG. 23C.

In addition, the above constructs can include unique sequence (ranging from 0 to 10 bases) internal to the Universal primers (i.e., Unique Ai, Unique Bi), represented as follows.

Univ.Primer U1-Unique Ai-Zipcode Zi-Target DNA-Unique Bi-Univ.Primer U2'

For detection using Zipcode Taqman assays, after the 8-20 cycles of universal amplification, the sample would be diluted 10- to 100-fold and unique primers would be added that overlap with the Unique Ai and the Unique Bi sequence for each product. The Taqman probe would be to the zipcode sequence.

Since each junction sequence between the zipcode identifier and target sequence is unique, the products of the initial universal amplification may also be identified and quantified using next-generation sequencing.

Another detection approach utilizing zipcodes involves having the zipcode portion split into two parts, which may be brought in proximity to each other using a short region of complementary sequence on both sides of the split parts. To generate a ligation product that can be detected using this approach, the first oligonucleotide probe would comprise a first portion of the zip-code and a first tag portion that is 3' to the first zip-code portion, and the second oligonucleotide probe would comprises a second portion of the zip-code and a second tag portion that is 5' to the second zip-code portion. To generate a primary extension product from the methylation sensitive restriction enzyme digestion-extension process of the present invention that can be detected using this approach, the first oligonucleotide probe would comprise a first portion of the zip-code and a first tag portion that is 3' to the first zip-code portion, and the second oligonucleotide primer of the primary oligonucleotide primer set would comprises a second portion of the zip-code and a second tag portion that is 5' to the second zip-code portion. The first and second tag portions of an oligonucleotide probe or probe/primer set are complementary to each other, and preferably between about 5 to 8 bases. This allows for transient hairpin formation of the resulting product at the short region when the two sections are on the same single strand of DNA, which is stabilized by hybridizing both halves of the zipcode sequence to a full length complementary zipcode sequence on an array, or alternatively as part of a Taqman assay.

Figure 24:
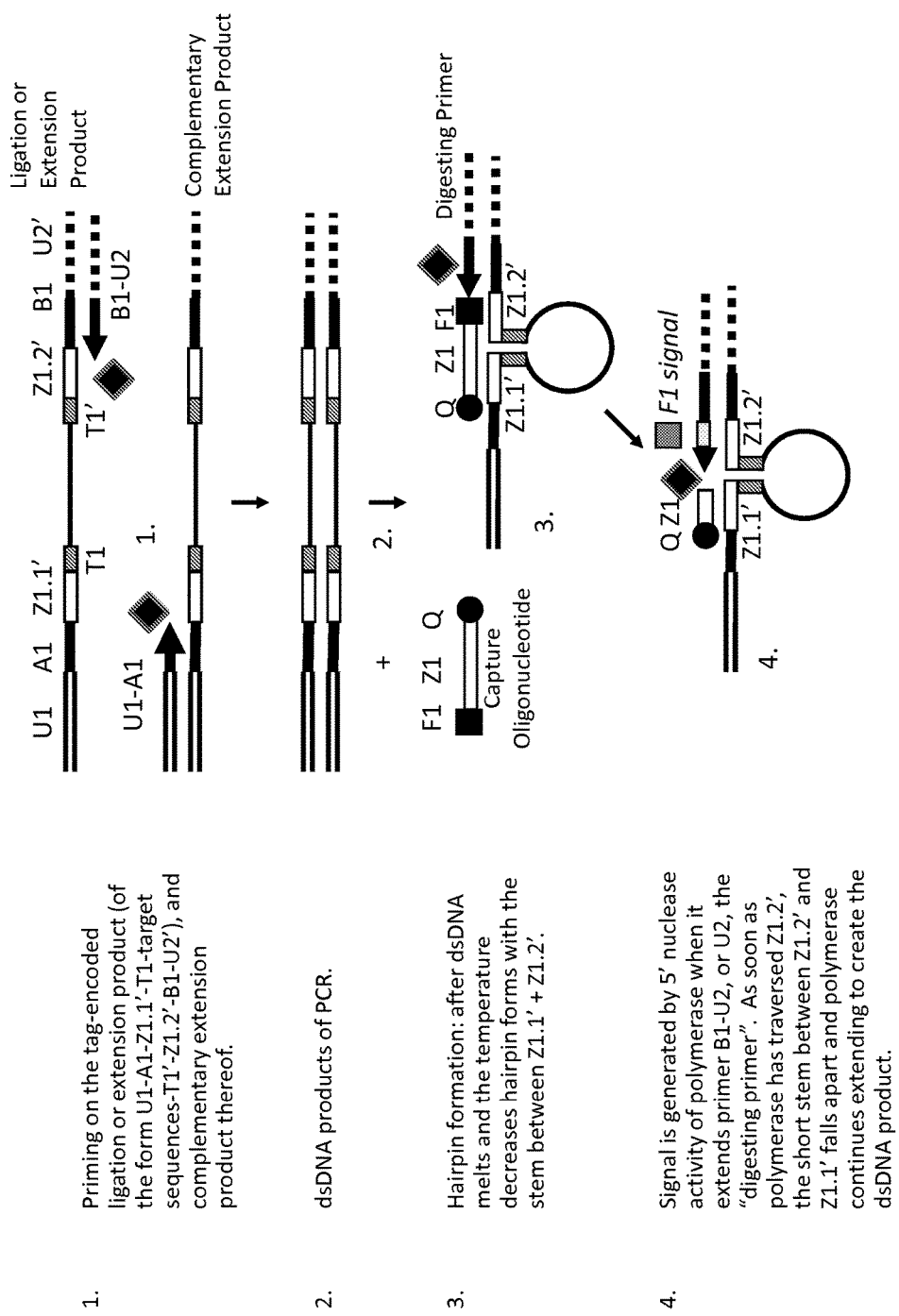
FIG. 24 shows an example of universal split zip-code hairpin detection of ligation or extension products formed using the methods of the present invention.

FIG. 24 shows an example of universal Taqman split zipcode hairpin detection. In this figure, and in accordance with the methods described above, a ligation product (FEN-ligation-methylation sensitive restriction enzyme digestion or methylation sensitive restriction enzyme digestion-ligation process) or a primary extension product (methylation sensitive restriction enzyme digestion-extension process) have already been formed. Ligation products are formed using oligonucleotide probe sets that comprise a first oligonucleotide probe having (i) a first 5' universal primer-specific portion (U1), (ii) a first short (1-10 bases) unique identifying sequence (A1), (iii) a first portion of a zip-code portion (Z1.1'), (iv) a first tag portion (T1) that is 3' to the first zip-code portion, and (v) a target-specific portion. The second oligonucleotide probe of the probe set has (i) a 3' universal primer-specific portion (U2'), (ii) a second short unique identifying sequence (B1), (iii) a second portion of a zip-code portion (Z1.2'), (iv) a second tag portion (T1') that is 5' to the second zip-code portion, and (v) a target-specific portion. Likewise, primary extension products are formed using a first oligonucleotide probe as described above and a second oligonucleotide primer of the primary oligonucleotide primer set that further comprises (ii) a second short unique identifying sequence (B1), (iii) a second portion of a zip-code portion (Z1.2'), (iv) a second tag portion (T1') that is 5' to the second zip-code portion. The resulting ligation products (or extension products of the ligations products) or primary extension products as shown in Step 1 of FIG. 24, contain the (i) first primer-specific portion, U1-A1, where U1 is a universal primer specific portion and A1 is a unique, product-specific primer portion, (ii) the first zip-code portion (Z1.1'), (iii) the first tag portion (T1), the digestion product portion, the second tag portion (T1'), the second portion of the zip-code (Z1.2'), and the second primer specific portion, B1-U2, where B1 is a unique, product-specific primer portion and U2 is a universal primer portion.

As shown in Step 1 of FIG. 24, the A1 and B1 unique sequences serve to facilitate a target-specific PCR amplification of the ligation product sequence when the PCR primers that are utilized span the universal primer portion and the A1 and B1 portions, respectively. This target-specific PCR amplification can optionally be preceded by a universal PCR amplification reaction using primers that hybridize to the 5' and 3' universal primer-specific portions. A first universal amplification reaction is particularly suitable when detecting low abundance target nucleic acid sequences in a sample.

Following the target-specific PCR amplification of the ligation products (extension products thereof) or primary extension products (FIG. 24, Step 1), the double stranded DNA products are denatured (FIG. 24, Step 2). As the temperature decreases, the first and second tag portions (T1 and T1') transiently hybridize together, bringing the first portion of the zipcode sequence (Z1.1' from the first oligonucleotide probe) in proximity to the second zipcode sequence (Z1.2' from the second oligonucleotide probe). The transient hybridization is stabilized by the simultaneous hybridization of a labeled capture oligonucleotide (Z1) that is complementary to the adjacently positioned zipcode sequences (FIG. 24, Step 3). In one embodiment, the capture oligonucleotide has a quencher molecule (Q) and a detectable label (F) that are separated from each other, where the detectable label is quenched when in close proximity to the quencher molecule. Signal is generated by 5' nuclease activity of a polymerase as it extends a primer (i.e., the "digesting primer") that is bound to the universal primer-specific portion (U2), the unique B1 portion, or a combination thereof, and cleaves the hybridized capture oligonucleotide. Primer extension cleaves the detectable label from the capture oligonucleotide releasing the detectable label from the quencher molecule, enabling detection (FIG. 24, Step 4). As soon as polymerase has traversed Z1.2', the short stem between Z1.2' and Z1.1' falls apart and polymerase continues extending to create the dsDNA product. A wide variety detectable labels, i.e., fluorescent dyes are known in the art and commercially available, e.g., FAM™ fluorescent dye, TET™ fluorescent dye, JOE™ fluorescent dye, VIC® fluorescent dye, HEX™ fluorescent dye, CY3™ fluorescent dye, TAMRA™ fluorescent dye, TexasRed® fluorescent dye, CY5™ fluorescent dye, and ROX™ fluorescent dye. Similarly, quencher molecules, e.g., MGB-NFQ, BHQ®-[0123] quencher, ZEN® quencher from INTEGRATED DNA TECHNOLOGIES®, are also well known to those skilled in the art.

Figure 25:
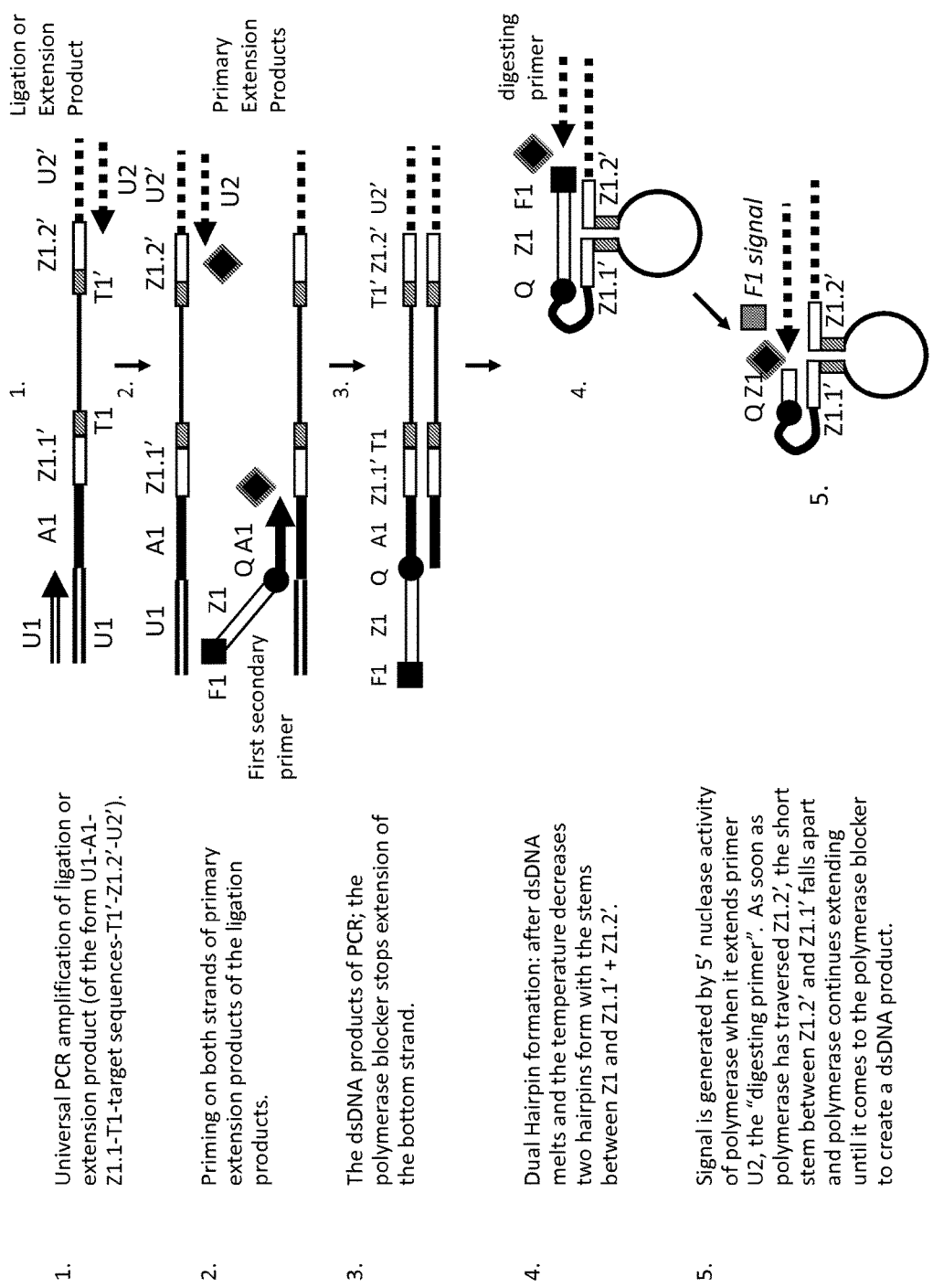
FIG. 25 shows an example of universal split zip-code hairpin detection of ligation or extension products formed using the methods of the present invention.

FIG. 25 shows another example of universal split zipcode hairpin detection. In this figure, and in accordance with the methods described above, a ligation product (FEN-ligation-methylation sensitive restriction enzyme digestion or methylation sensitive restriction enzyme digestion-ligation process) or a primary extension product (methylation sensitive restriction enzyme digestion-extension process) have already been formed. Ligation products are formed using oligonucleotide probe sets (not shown) that comprise a first oligonucleotide probe having (i) a first 5' universal primer-specific portion (U1), (ii) a second primer-specific portion (A1) that is a ligation product-specific primer portion, (iii) a first portion of a zip-code portion (Z1.1'), (iv) a first tag portion (T1) that is 3' to the first zip-code portion, and (v) a target-specific portion. The second oligonucleotide probe of the probe set has (i) a 3' universal primer-specific portion (U2'), (ii) a second portion of a zip-code portion (Z1.2'), (iii) a second tag portion (T1') that is 5' to the second zip-code portion, and (iv) a target-specific portion. The primary extension products from a methylation sensitive restriction enzyme-extension process are formed using a first oligonucleotide probe having a first primer-specific portion (U1 and A1), a first portion of the zip-code (Z1.1') and a first tag portion (T1) that is 3' to the first zip-code portion. The second oligonucleotide primer of the primary oligonucleotide primer set comprises a second portion of the zip-code (Z1.2'), a second tag portion (T1') that is 5' to the second zip-code portion, and the second primer-specific portion (U2). The resulting ligation product or primary extension product as shown in step 1 of FIG. 25, contain the (i) first primer-specific portion, U1-A1, where U1 is a universal primer specific portion and A1 is a unique, product-specific primer portion (i.e., a third-primer portion), (ii) the first zip-code portion (Z1.1'), (iii) the first tag portion (T1), the digestion product portion, the second tag portion (T1'), the second portion of the zip-code (Z1.2'), and the second primer specific portion (U2).

In Step 1 of FIG. 25, the ligation products or primary extension products are optionally initially amplified using a universal oligonucleotide primer set, i.e., a first oligonucleotide primer (U1) having the same sequence as the 5' universal primer-specific portion, and a second oligonucleotide primer (U2) that is complementary to the 3' universal primer-specific portion. The amplified ligation product or amplified primary extension products formed from the primary universal PCR step are subject to a secondary PCR step (FIG. 25, Step 2) using a secondary primer set that includes a first secondary oligonucleotide primer having (a) a nucleotide sequence that is the same as the second primer-specific portion of the first oligonucleotide probe (A1), (b) a capture oligonucleotide portion (Z1) that is complementary to adjacently positioned first and second zip-code portions of an oligonucleotide probe set, (c) a quencher molecule (Q) and a detectable label (F) separated by said capture oligonucleotide portion. The second secondary oligonucleotide primer (U2) of the primer set has the same nucleotide sequence as the second primary oligonucleotide primer of the primary PCR (i.e., it is complementary to the 3' universal primer-specific portion of the ligation product). The quencher molecule of the first secondary primer can serve as a polymerase blocker to block polymerase extension of the bottom strand. Alternatively, a polymerase blocker such as HEG (hexethylene glycol), THF (tetrahydrofuran), Sp-18, or any other blocker known in the art that is sufficient to stop polymerase extension can be positioned proximal to the quencher moiety. The double stranded DNA products (shown in FIG. 25, Step 3) are denatured and the temperature decreased to allow dual hairpin formation with stems between Z1.1' and Z1.2' (stem formed by hybridization between T1 and T1') and between the capture oligonucleotide portion (Z1) and Z1.1'/Z1.2' (FIG. 25, Step 4). Signal is generated by 5' nuclease activity of polymerase when it extends a "digesting primer" complementary to the 5' universal primer-specific portion. Primer extension cleaves the detectable label (F) or the quencher molecule (Q) from the capture oligonucleotide releasing the detectable label (F) from the quencher molecule (Q), enabling detection (FIG. 25, Step 5). As soon as polymerase has traversed Z1.2', the short stem between Z1.2 and Z1.1' falls apart and polymerase continues extending until it comes to the polymerase blocker to create a dsDNA product similar to that in step 1, but lacking the fluorescent D1 signal.

An alternative approach to utilizing the zipcode/capture oligonucleotide sequences for detection involves the UniTaq approach. The UniTaq system is fully described in U.S. Patent Application Publication No. 2011/0212846 to Spier, which is hereby incorporated by reference in its entirety. The UniTaq system involves the use of two to three short (1-10 nucleotides) unique "tag" sequences, where at least one of the unique tag sequences (Ai) is present in the first oligonucleotide probe, and the second and third unique tag portions (Bi and Ci) are in the second oligonucleotide probe sequence. In the case of primary extension products formed in a methylation sensitive restriction enzyme-extension process, the second and third unique tag portions (Bi and Ci) are in the second oligonucleotide primer sequence. The resulting ligation product or primary extension products of the present invention will contain the Ai sequence—target specific sequences—Bi sequence—Ci sequence. The essence of the UniTaq approach is that both oligonucleotide probes of a ligation probe set need to be correct in order to get a positive signal, which allows for highly multiplexed nucleic acid detection. For example, and as described herein, this is achieved by requiring hybridization of two parts, i.e., two of the tags, to each other.

In one embodiment of the present invention, the UniTaq tag portions of an oligonucleotide probe set or probe/primer set are "allele-specific" and used to identify and distinguish individual ligated product sequences in a sample. In accordance with this embodiment, the UniTaq portions for each different ligation product or primary extension product are different. In an alternative embodiment, where the goal is to simply detect the presence of a methylated target nucleic acid molecule, the same UniTaq tag portions can be used to detect different ligation products or primary extension products. In either embodiment, incorporation of the UniTaq tags portions into one of the oligonucleotide probes of a probe set allows for highly multiplexed detection of various target sequences simultaneously.

Figure 26A:
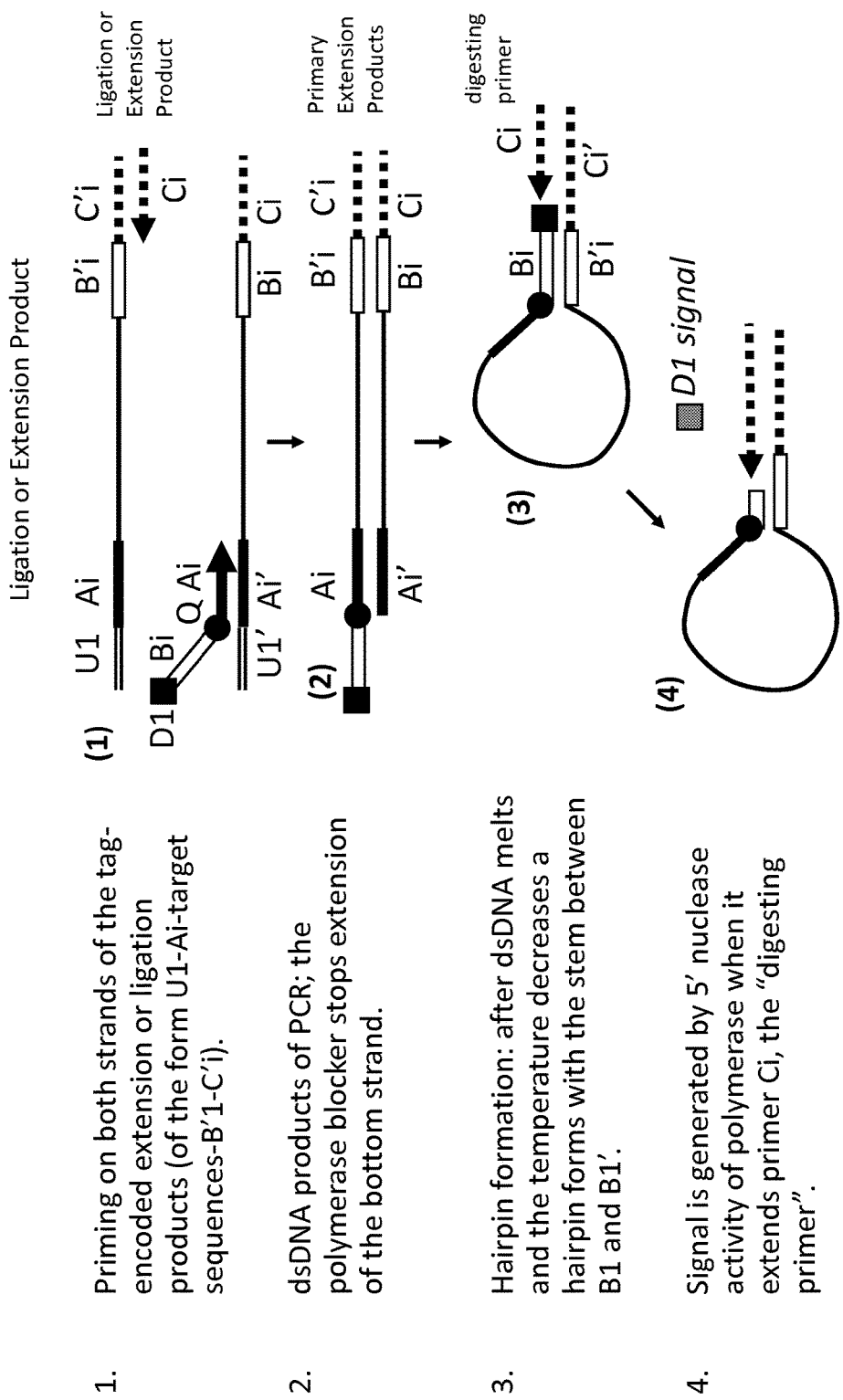
FIGS. 26A-26C show three examples for PCR detection of the ligation or extension products of the present invention using UniTaq mediate hairpin formation (FIG. 26A), UniTaq 5' nuclease probes (FIG. 26B), and UniTaq circle detection (FIG. 26C).
Figures 26B, 26C:
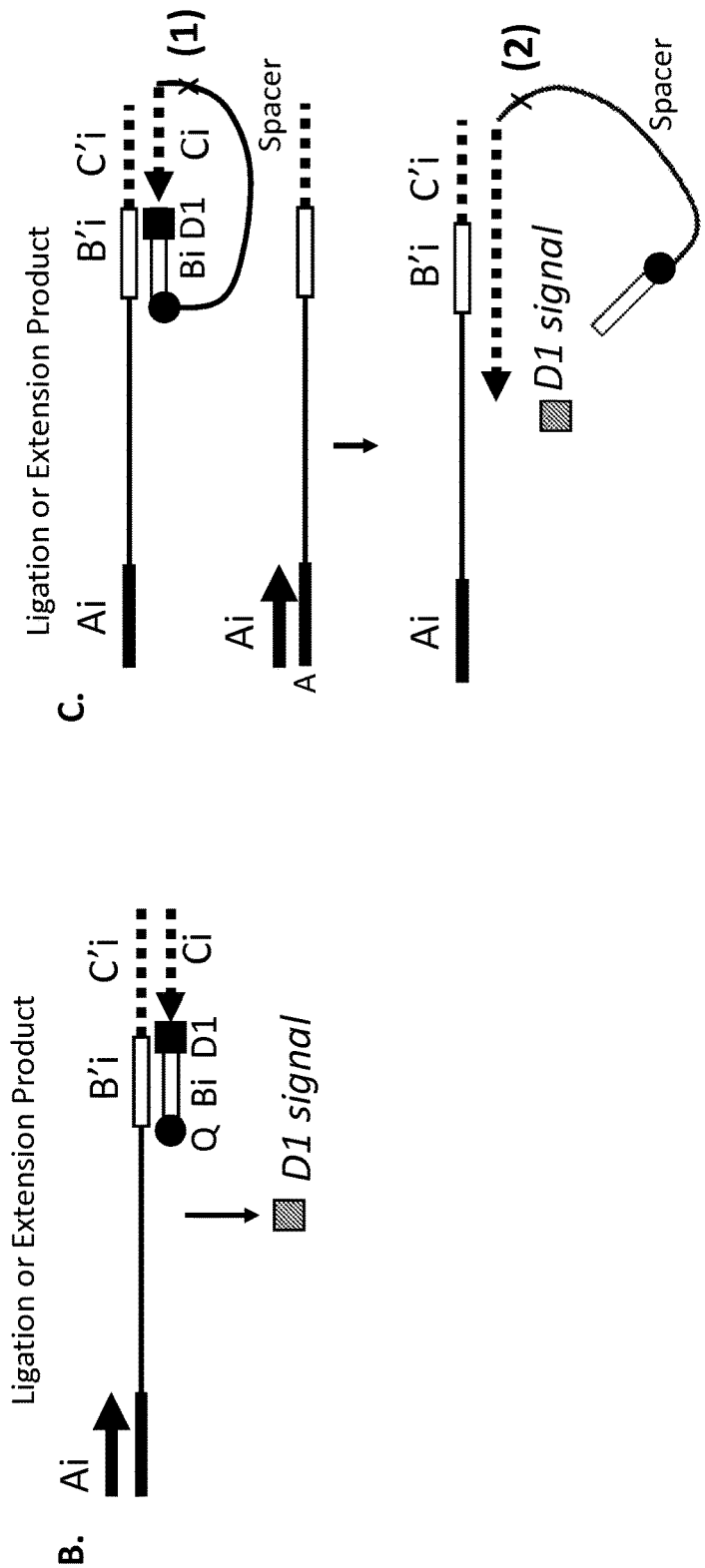
Figure 27:
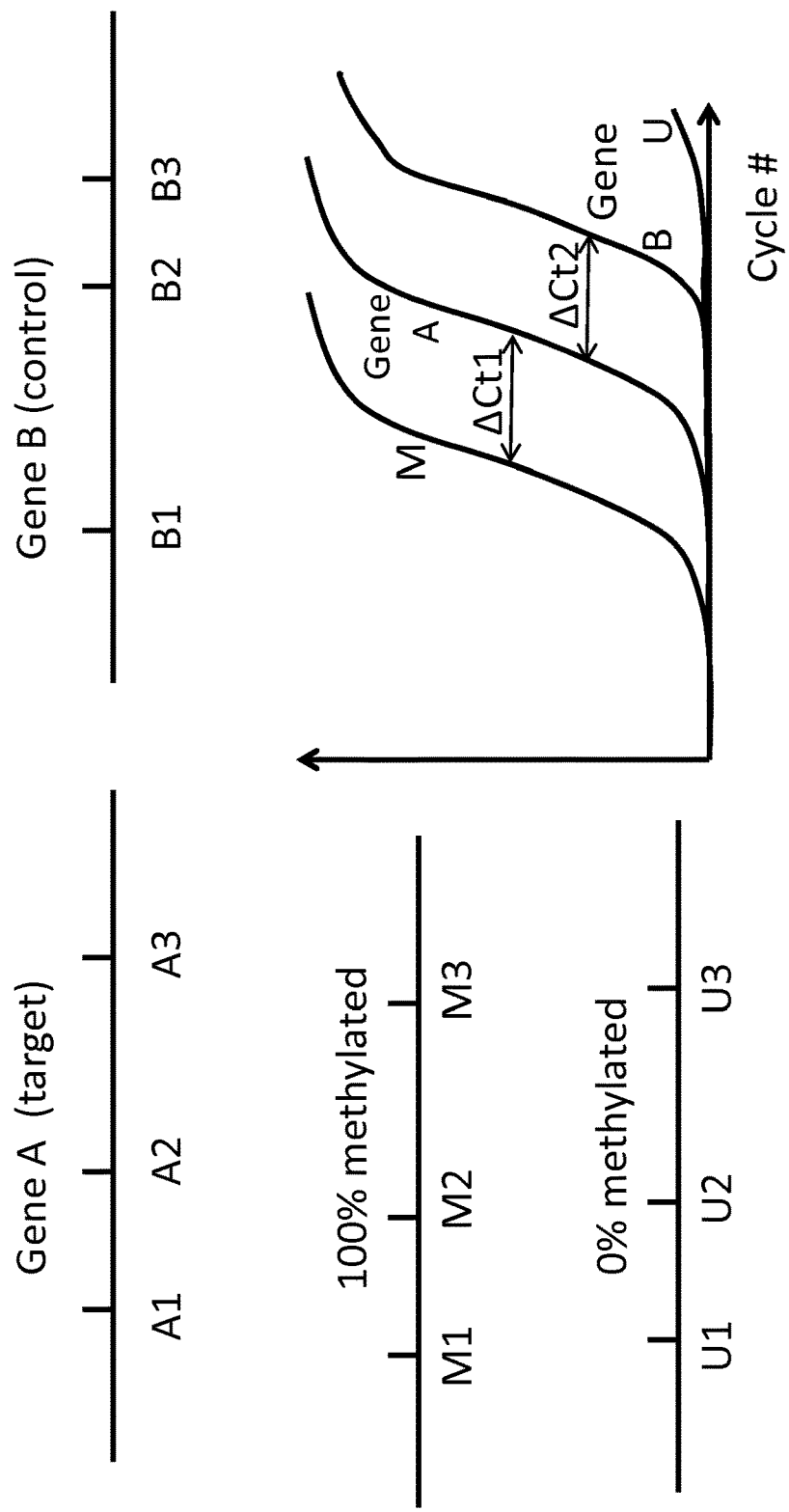
FIG. 27 shows how to combine signal from several methylation sites and normalizing against a control gene. There may be several target and several control genes. Signal "M" is from fully methylated template. Signal "Gene A" is from methylation level of gene A. Signal "Gene B" is from methylation level of gene B (control). Signal "U" is from unmethylated template. ΔCt1 is used to estimate percentage methylation relative to 100% methylated; ΔCt2 measures differential methylation between the two genes. As described herein, using a mixture of amplification incompetent oligonucleotide probes with amplification competent oligonucleotide probes at a ratio of 99:1 will provide a control signal that represents 1% of starting total input DNA template. In this manner, low levels of methylated DNA in an excess of unmethylated DNA can be accurately quantified.

FIGS. 26A-26C show various ways in which the UniTaq tag system can be incorporated into the various methylation sensitive restriction enzyme reaction processes of the present invention. In the first approach, shown in FIG. 26A, the ligation product (or extension products thereof) or primary extension products containing Ai (a first primer-specific portion), B'i (a UniTaq detection portion), and C'i (a second primer-specific portion) are primed on both strands using a first oligonucleotide primer having the same nucleotide sequence as Ai, and a second oligonucleotide primer that is complementary to C'i (i.e., Ci). The first oligonucleotide primer also includes a UniTaq detection probe (Bi) that has a detectable label D1 on one end and a quencher molecule (Q) on the other end (D1-Bi-Q-Ai). Optionally positioned proximal to the quencher is a polymerase blocking unit, e.g., HEG, THF, Sp-18, or any other blocker known in the art that is sufficient to stop polymerase extension. A polymerase blocker may not be required if the 5'-tail that folds into a stem has one or more bases at the 5' end that are not complementary to the middle universal tag sequence, so that the hairpin formed by the opposite strand of DNA (with the 3'-end at the end of the stem) is not extendable during PCR. One can also design a small hairpin into the 5' portion of the primer 100, so that the dye and the quencher are brought closer together, similar to "Sunrise" primers and probes to improve quenching and decrease background fluorescence. For example, see U.S. Pat. Nos. 5,866,336 and 6,270,967, which are hereby incorporated by reference in their entirety.

PCR amplification results in double stranded product (FIG. 26A, Step 2). In this example, a polymerase blocking unit prevents a polymerase from copying the 5' portion (Bi) of the first universal primer, such that the bottom strand of product cannot form a hairpin when it becomes single-stranded. Formation of such a hairpin would result in the 3' end of the stem annealing to the amplicon such that polymerase extension of this 3' end would terminate the PCR reaction.

The double stranded PCR products are melted (e.g., by raising the temperature to approximately 95° C. to separate the upper strand from the lower strand, and when the temperature is subsequently decreased, the upper strand of product forms a hairpin having a stem between 5' portion (Bi) of the first oligonucleotide primer and portion B'i at the opposite end of the strand (FIG. 26A, Step 3). Also during this step, the second oligonucleotide primer anneals to the 5'-primer specific portion (C'i). Intra-molecular hairpin formation occurs rapidly and is driven by thermodynamics: the free energy is determined by stem length, GC-content and loop length. It is important that the melting temperature (Tm) of the hairpin be significantly higher (e.g., approximately 10° C. or higher) than the Tm of the second oligonucleotide primer. This way, when the temperature is decreased, nearly 100% of the molecules will form the hairpin before the second universal primer anneals and is extended. Upon extension of the second universal primer in step 4, 5' nuclease activity of the polymerase cleaves the detectable label D1 or the quencher molecule from the 5' end of the amplicon, thereby increasing the distance between the label and the quencher or FRET dye and permitting detection of the label. A wide variety fluorescent dyes are known in the art and commercially available, e.g., FAM fluorescent dye, TET™ fluorescent dye, JOE™ fluorescent dye, VIC® fluorescent dye, HEX™ fluorescent dye, CY3™ fluorescent dye, TAMRA™ fluorescent dye, TexasRed® fluorescent dye, CY5™ fluorescent dye, and ROX™ fluorescent dye. Similarly, suitable quencher molecules, e.g., MGB-NFQ, BHQ®-[0123] quencher, ZEN® quencher from INTEGRATED DNA TECHNOLOGIES®, are well known to those skilled in the art.

In the approach shown in FIG. 26B, a traditional Taqman™ assay is used to detect the ligation product or primary extension product. This method involves providing a UniTaq detection probe (Bi) that is complementary to the UniTaq detection portion (B'i). The UniTaq detection probe comprises a quencher molecule (Q) and a detectable label (D1) that are separated from each other. The UniTaq detection probe hybridizes to its complementary UniTaq detection portion on the ligation product or primary extension product at the same time the second oligonucleotide primer (Ci) hybridizes to the 5' C'i primer-specific portion of the ligation product during PCR amplification. Extension of the second oligonucleotide primer generates a signal by 5' exonuclease cleavage of D1 and separation of D1 from the quencher.

A further example detection format involving the formation of a universal circle is schematically illustrated in FIG. 26C. As above, the ligation product or primary extension product in FIG. 26C contains Ai (a first primer-specific portion), target-specific portions, B'i (a UniTaq detection portion), and C'i (a second primer-specific portion). The ligation product or primary extension product is amplified using a first oligonucleotide primer (Ai) that has the same nucleotide sequence as the Ai primer specific portion of the ligation product, and a second oligonucleotide primer that includes (i) primer portion (Ci) that is complementary to the 5' C'i primer specific portion of the ligation product, (ii) a spacer region containing a polymerase blocker (x), (iii) a quencher molecule (Q), (iv) a UniTaq detection probe (Bi), and (v) a detectable label (D1) that is quenched when in close proximity to the quencher molecule. During PCR, the primer portion of the second oligonucleotide primer (Ci) anneals to primer-specific portion of the ligation product while the UniTaq detection probe (Bi) hybridizes to its complementary UniTaq detection portion of the ligation product (FIG. 26C, Step 1). In this example, extension of the second oligonucleotide primer (FIG. 26C, Step 2) cleaves the hybridized UniTaq detection probe (Bi) thereby releasing the detectable label. The release of the detectable label from the quencher molecule generates a detectable signal.

The challenge to developing reliable diagnostic and screening tests based on changes in DNA methylation, is to distinguish those markers emanating from the tumor or fetus that are indicative of disease (i.e. early cancer) vs. presence of the same markers emanating from normal tissue. There is also a need to balance the number of markers examined and the cost of the test, with the specificity and sensitivity of the assay. This is a challenge that needs to address the biological variation in diseases such as cancer. In many cases the assay should serve as a screening tool, requiring the availability of secondary diagnostic follow-up (i.e. colonoscopy, amniocentesis).

Compounding the biological problem is the need to reliably detect changes in DNA methylation in a very small number of initial cells (i.e. from CTCs), or when the cancer or fetus-specific signal is in the presence of a majority of nucleic acid emanating from normal cells.

Finally, there is the technical challenge to distinguish true signal resulting from detecting the desired disease-specific nucleic acid methylation marker, vs. false signal generated from normal nucleic acids present in the sample, vs. false signal generated in the absence of the disease-specific nucleic acid methylation marker.

The methods of the present invention described herein provide solutions to these challenges. These solutions share some common themes highlighted below.

The first theme is multiplexing. PCR works best when primer concentration is relatively high, from 50 nM to 500 nM, limiting multiplexing. Further, the more PCR primer pairs added, the chances of amplifying incorrect products or creating primer-dimers increase exponentially. In contrast, for LDR probes, low concentrations on the order of 4 nM to 20 nM are used, and probe-dimers are limited by the requirement for adjacent hybridization on the target to allow for a ligation event. Use of low concentrations of gene-specific PCR primers or LDR probes with universal primer sequence "tails" allows for subsequent addition of higher concentrations of universal primers to achieve proportional amplification of the initial PCR or LDR products. Herein, the traditional LDR approach is flipped by using oligonucleotide adapters as templates to capture and append specific tags to very low-abundance single-stranded target fragments.

The second theme relates to fluctuations in signal due to low input target nucleic acids. Often, the target nucleic acid originated from a few cells, either captured as CTCs, or from tumor cells that underwent apoptosis and released their DNA as small fragments (140 to 160 bp) in the serum. Under such conditions, it is preferable to perform some level of proportional amplification to avoid missing the signal altogether or reporting inaccurate copy number due to Poisson distribution when distributing small numbers of starting molecules into individual wells (for real-time, or digital PCR quantification). As long as these initial universal amplifications are kept at a reasonable level (approximately 8 to 20 cycles), the risk of carryover contamination during opening of the tube and distributing amplicons for subsequent detection/quantification (using real-time, or droplet PCR) is minimized. If needed, carryover signal may be eliminated by standard uracil incorporation during the universal amplification step, and using UNG and AP endonuclease in the pre-amplification workup procedure. Alternatively, carryover signal may be avoided altogether by performing multiple steps in a closed system, such as plastic microfabricated "lab on a chip" devices.

The third theme is target-independent signal. This would arise from either polymerase or ligase reactions that occur in the absence of the correct target. Some of this signal may be minimized by judicious primer design. For ligation reactions, the 5'→3' nuclease activity of polymerase may be used to liberate the 5' phosphate of the downstream ligation primer (only when hybridized to the target), so it is suitable for ligation. In the present invention, the specificity of methyl sensitive and methyl insensitive restriction endonucleases is used to generate ligation competent 5' phosphate and 3' OH groups at defined positions in the target.

The fourth theme is either suppressed (reduced) amplification or incorrect (false) amplification due to unused primers in the reaction. One approach to eliminate such unused primers is to capture genomic DNA on a solid support, allow ligation primers to hybridize and ligate, and then remove primers or products that are not hybridized to the genomic DNA on a solid support. Another approach is to eliminate oligonucleotide template adapter strands, either by using uracil DNA glycosylase to digest uracil-containing artificial template, or by using the 5'→3' nuclease activity of polymerase to digest the template strand of a ligated product. Still another approach is to design the upstream hairpin oligonucleotide adapter so in the absence of ligation it extends on itself and will not amplify further. Still another approach is to design the downstream hairpin oligonucleotide adapter to comprise a 5' flap that is cleaved off by the 5'→3' nuclease activity of polymerase when hybridized to the cut fragment, but uncut flap hybridizes back to a complementary region on the adapter such that it inhibits subsequent priming of an unligated oligonucleotide. Still another approach is to incorporate a blocking group within the adapter oligonucleotide that interferes with extension of the 3' end. Still another approach is to use a blocking group that prevents extension of an unligated upstream hairpinned adapter past the blocking group and therefore avoid generating an amplification competent artificial template, but said blocking group does not interfere with the 5'→3' nuclease activity of polymerase to digest the template strand of a ligated product. Still another approach is to use universal primer designs on either PCR or oligonucleotide adapter primers, which are slightly shorter than Universal primers. This allows initial universal amplification at a lower cycling temperature (i.e. 55° C. annealing) followed by higher cycling temperature (i.e. 65° C. annealing) such that the universal primers bind preferentially to the desired product (compared to composite PCR or oligonucleotide adapter primers binding to incorrect products).

The methods of the present invention described herein are capable of detecting and quantifying one or more low abundance target nucleic acid molecules that have one or more methylated residues and/or one or more unmethylated residues. As used herein "low abundance target nucleic acid molecule" refers to a target nucleic acid molecule that is present at levels as low as 1% to 0.01% of the sample. In other words, a low abundance nucleic acid molecule with one or more methylated residues or one or more unmethylated residues can be distinguished from a 100 to 10,000-fold excess of nucleic acid molecules in the sample having a similar nucleotide sequence as the low abundance nucleic acid molecules but without the one or more methylated residues or with one or more methylated residues, respectively. In some embodiments of the present invention, the copy number of one or more low abundance target nucleotide sequences are quantified relative to the copy number from an excess of nucleic acid molecules in the sample having a similar nucleotide sequence as the low abundance nucleic acid molecules. In other embodiments of the present invention, the one or more low abundance target nucleotide sequences are quantified in the sample. This quantitation can be absolute or relative to other nucleotide sequences in the sample. In other embodiments of the present invention, the relative copy number of one or more target nucleotide sequences are quantified.

The low abundance target nucleic acid molecules to be detected can be present in any biological sample, including, without limitation, tissue, cells, serum, blood, plasma, amniotic fluid, sputum, urine, bodily fluids, bodily secretions, bodily excretions, cell-free circulating nucleic acids, cell-free circulating fetal nucleic acids in pregnant woman, circulating tumor cells, tumor, tumor biopsy, and exosomes.

With regard to early cancer detection, the methods of the present invention are suitable for high sensitivity methylation marker detection for promoter hypermethylation (when present at 1% to 0.01%) in methyl enriched DNA, or even total serum DNA, e.g., promoter hypermethylation in p16 and other tumor suppressor genes, CpG "islands" also, Sept9, Vimentin, etc. This approach also enables high sensitivity unmethylated marker detection for promoter hypomethylation (when present at 1% to 0.1%) in total serum DNA. The methods of the present invention are also suitable for high sensitivity unmethylated marker detection, for example, promoter hypomethylation when present at 1% to 0.1% in total serum DNA. For example, the method is useful for detecting promoter hypomethylation in potential oncogenes, CpG "shoreline" regions also, loss of methylation in Alu or other repeat sequences.

The presence and absence of methylation in certain genetic regions has prenatal diagnostic and prognostic applications. For example, aberrant methylation on regions on chromosomes 13, 18, 21, X, and Y can be used to diagnose Down Syndrome (Patsalis et al., "A New Non-Invasive Prenatal Diagnosis of Down Syndrome through Epigenetic Markers and Real-Time qPCR," *Exp. Opin. Biol. Ther.* 12(Suppl. 1): S155-S161 (2012), which is hereby incorporated by reference in its entirety). Because fetal DNA and maternal DNA are differentially methylated, cell-free fetal DNA in maternal plasma can provide a source of fetal DNA, which can be obtained non-invasively and utilized to assess the methylation state of the aforementioned chromosomes. Since cell-free fetal DNA only accounts for 3-6% of total DNA in maternal circulation during the first trimester, the highly sensitive methods of the present invention are particularly suitable for use in these types of non-invasive prenatal diagnostic assays. The present invention allows for non-invasive prenatal detection of chromosomal aneuploidies in fetal DNA by using digital PCR to quantify methylation in chromosomal regions that are unmethylated in normal serum, and/or by using digital PCR to quantify methylation in chromosomal regions that are methylated in DNA isolated from normal serum.

PROPHETIC EXAMPLES

The following examples are provided to illustrate prophetic embodiments of the present invention but they are by no means intended to limit its scope Prophetic Example 1—High Sensitivity Methylation Marker Detection for Promoter Hypermethylation (When Present at 1% to 0.01%) in Methyl Enriched DNA, or Total Plasma DNA Promoter methylation plays an important role in regulating gene expression. Promoters for genes often have regions of high CpG content known as "CpG Islands". When genes, such as tumor suppressor genes, with promoter CpG islands are turned off, this is usually accompanied with methylation of most CpG sequences within the promoter and 1$^{st}$ exon regions. There have been two traditional approaches to detecting methylation changes.

The first takes advantage of methyl-sensitive restriction enzymes, wherein genomic DNA is cleaved when unmethylated, and this is followed by a PCR amplification using primers that flank the site(s). If the DNA was methylated, it should amplify, if unmethylated, it should not amplify. This technique has the disadvantage that digestions do not always go to completion, and further, it is not accurate for finding low levels of methylated DNA when the majority of the same sequence is unmethylated, as would be the case with plasma detection.

The second approach is known as "Methyl-specific PCR" and is based on bisulfite treatment of DNA, which converts unmethylated C's to U's. If the base is methylated, then it is not converted. Methyl-specific PCR is based on using primers and Taqman probes that are specific for the resultant converted sequence if it were methylated, but not unmethylated. Methyl-specific PCR has the advantage of being able to detect very low levels of methylated DNA. A further improvement of this technique employs a blocking oligonucleotide that hybridizes to the sequence for bisulfite-converted unmethylated DNA, thus enriching for amplification of bisulfite-converted methylated DNA. The disadvantage is that bisulfite treatment destroys from 50% to 90% of the original DNA integrity by nicking it. When starting with DNA from the plasma (with average length of about 160 bases), this can be a significant problem. Further, converting C's to U's reduces the complexity of the sequence from 4 bases to 3 bases. Thus, non-specific amplifications can occur. This usually necessitates a nested-PCR approach, this runs the risk of carryover contamination and is generally not ideal for multiplexed amplifications.

BstUI is a thermophilic enzyme that recognizes the 4 base sequence CG^CG, cleaving in the middle to generate blunt end sites (see U.S. Pat. No. 7,358,048 to Barany et al., which is hereby incorporated by reference in its entirety). Similar thermophilic isoschizomers include Bsh1236I, BspFNI, BstFNI, FnuDII, and ThaI A mesophilic isoschizomer (AccII) has also been reported. The recognition site is often found in CpG islands and provides tandem CpG's where either none, one, or both may be methylated. BstUI nicks double-stranded template DNA on the unmethylated top strand, when there is a single methylated CpG on the bottom strand. However, BstUI does not nick double-stranded template DNA on the unmethylated top strand, when both CpG's on the bottom strand are methylated. The enzyme Hpy99I (recognition sequence CGWCG^) may have similar properties to BstUI. (HpaII also does not nick double-stranded template DNA on the unmethylated top strand, when its single CpG on the bottom strand is methylated.)

In contrast, an enzyme such as HinP1I (recognition sequence G^CGC, cleaves with a 2-base 5' overhang), nicks double-stranded template DNA on the unmethylated top strand, when the CpG on the bottom strand is methylated. The enzymes AciI=(recognition sequence, C^cCGC and G^CGG) and HpyCH4IV (recognition sequence, A^CGT) may have similar properties to HinP1I.

Overview of First Approach: Nuclease-Ligation-Methylation Sensitive Restriction Enzyme Digestion.

This approach depends on the fidelity of three enzymes: (i) the restriction activity of BstUI (ii) the polymerase 5'→3' nuclease or flap cleavage enzyme in discriminating a match from mismatch on the 5' side of the downstream probe, and (iii) the ligase in discriminating a match from mismatch on the 3' side of the upstream probe. Isolated genomic DNA, or methyl enriched DNA is treated with the methyl sensitive enzyme BstUI. Hybridization of two probes to the target allows for cleavage of the flap by polymerase, and ligation by ligase only if the second base of recognition sequence is unchanged. Once a ligation event has taken place, fresh BstUI is added to cleave any products that were not fully methylated (i.e. 5' C*GC*G 3') in the original genomic DNA. Those products that are not cleaved will be amplified in a subsequent PCR amplification step, and thus this is the key discriminatory step.

By insisting on having an endonuclease generate the 5' phosphate, this avoids false signal, and should get rid of any non-specific ligation signal as well. Thus, any rare fragment of genomic DNA that was single-stranded after purification, or did not get cleaved will not form a productive substrate for subsequent PCR amplifications, as the product has non-genomic sequences on both sides.

To summarize the levels of discrimination of the above approach for detection of low-abundance methylation v1 (See FIGS. 2A-2I):

1. Use of methylation sensitive BstUI restriction enzymes to cleave double-stranded target when not methylated.
2. Use of 5'-3' nuclease activity of polymerase or Fen nuclease on downstream probe.
3. Use of 3' ligation fidelity of thermostable ligase on upstream probe.
4. Reuse of methylation sensitive BstUI restriction enzymes to cleave double-stranded target when original genomic DNA was not methylated.
5. Use of sequences on the 5' end of downstream probes, such that when they are not cleaved, form hairpins at lower temperature and extend on themselves to form products that do not amplify.

An advantage of this approach is that even if the target is partially methylated, and BstUI nicks the site, the probes may religate and amplify nevertheless. Probes may be designed to contain methyl groups not at the junction to prevent nicking the probe strand at an incorrect position should the probe hybridize across one or more adjacent BstUI sequence that are not being tested for methylation status.

A disadvantage of this approach is that in the unlikely chance that the BstUI site is mutated on one of the outside bases then some ligation would occur even with a mismatch (not at the ligation junction), and since the site was mutated, it would not be recleaved by BstUI. However, it would give a very high signal, which would immediately be flagged as a false positive.

An alternative approach (see below), using coupled matched upstream and downstream probe is also presented.

There are two variations to consider. In the first variation, (shown in FIGS. 3A-3I), the coupled primers are designed to form hairpins at lower temperature and extend on themselves to form products that do not amplify.

To summarize the levels of discrimination of the first approach using coupled primers for detection of each BstUI methylated site (See FIGS. 3A-3I):

1. Use of methylation sensitive BstUI restriction enzymes to cleave double-stranded target when not methylated.
2. Use of 5'-3' nuclease activity of polymerase or Fen nuclease on downstream probe.
3. Use of 3' ligation fidelity of thermostable ligase on upstream probe.
4. Reuse of methylation sensitive BstUI restriction enzymes to cleave double-stranded target when original genomic DNA was not methylated.

5. Use of lower probe concentrations to minimize target-independent events.
6. Use of sequences on the coupled primers, such that when they are not ligated, form hairpins at lower temperature and extend on themselves to form products that do not amplify.

In the second variation (see FIGS. 3J-3P), the coupled primers are ligated to form a closed circle on the target, and unligated coupled primers (as well as input template DNA) are removed by exonuclease digestion.

To summarize the levels of discrimination of the first approach using coupled primers for detection of each BstUI methylated site:
1. Use of methylation sensitive BstUI restriction enzymes to cleave double-stranded target when not methylated.
2. Use of 5'-3' nuclease activity of polymerase or Fen nuclease on downstream probe.
3. Use of 3' ligation fidelity of thermostable ligase on upstream probe.
4. Reuse of methylation sensitive BstUI restriction enzymes to cleave double-stranded target when original genomic DNA was not methylated.
5. Use of lower probe concentrations to minimize target-independent events.
6. Use of exonucleases to destroy unligated probe and target.

As a control for the total amount of DNA present (not shown), one can choose a nearby target region that is methylated in normal DNA from the plasma or serum, and/or in an imprinted gene where at least one chromosome is always methylated. The upstream oligonucleotide probe that is ligated to the downstream probe is a mixture of two oligos: (i) An oligonucleotide present at 1 in 100 with the correct UniTaq specific sequence, and (ii) an oligonucleotide present at 99 in 100 with a sequence that does not contain the correct UniTaq specific sequence and optionally has about 6-10 bases complementary to its 3' end. The ligation product containing the UniTaq sequences amplifies and will give a signal equivalent to 1 in 100 of the original template. The majority ligation product lacks the universal sequence on the 5' end, and does not amplify exponentially. Unligated upstream probe will form a hairpin back on itself, and extend its own 3' sequence on itself, taking it out of contention for becoming part of another PCR amplicon.

As a control for the total amount of DNA present, this approach may also be used with coupled probes, again on a target region as described above. One uses a mixture of two oligonucleotides: (i) An oligonucleotide present at 1 in 100 with the correct UniTaq and/or other tag sequence, and (ii) an oligonucleotide present at 99 in 100 with a sequence that either lacks or has incorrect tag sequences. The ligation product containing the UniTaq and/or tag sequences amplifies and will give a signal equivalent to 1 in 100 of the original template. The majority of ligation product either lacks or has incorrect tag sequences, and does not amplify exponentially Detailed Protocol for Highly Sensitive Detection of Methylation Marker (when Present at 1% to 0.01%):

Optional Step 1: Cleave isolated genomic DNA, or methyl enriched DNA with the methyl sensitive enzyme BstUI. Preferably, two or three sites per promoter are chosen for determining methylation status. This step also would destroy any carryover contamination PCR amplicon (which would not be methylated)

Step 2: Denature genomic DNA from plasma (94° C. 1 minute) in the presence of upstream LDR probes (5' Universal Primer U1, followed by UniTaq Ai, followed by target-specific sequence, and the G base at the 3' end), downstream LDR probe (5' of 20 base extra overhang, where 6-10 bases are complementary to 3' end of Univ.Primer U2' sequence, followed by target-specific sequence—UniTaq Bi'-Univ.Primer U2'), Taq polymerase, and thermostable ligase (preferably from strain AK16D). Perform one or more LDR reactions.

Step 3: Add hot start dNTP's Universal Primer U1, Universal Primer U2, and BstUI. Incubate at 55° C. (allows BstUI to cleave unmethylated ligation products, and activates dNTPs) to allow unligated downstream probes to self-hairpin to the 6-10 bases that are complementary to 3' end, which extends to create longer hairpins that render these downstream probe refractory to further amplification. Then, allow PCR amplification to proceed for 8-20 cycles. In one variation, the universal primer tails U1 and U2 on the LDR compound probes are slightly shorter than Universal primers U1 and U2. This allows initial universal amplification at a lower cycling temperature (i.e. 55° C. annealing) followed by higher cycling temperature (i.e. 65° C. annealing) such that the universal primers U1 and U2 bind preferentially to the desired product (compared to composite LDR probe binding to incorrect products). Further the universal primers U1 and U2 contain a short sequence in common (i.e. 6-10 bases) to avoid primer dimer formation. These conditions amplify fragments of the sequence:
Univ.Primer U1-UniTaq Ai-Upstream Target-CGCG-Downstream Target-UniTaq Bi'-Univ.Primer U2'

Step 4: Open tube, dilute 10- to 100-fold and distribute aliquots to Taqman wells, each well containing the following primers: Universal Primer U2 and UniTaq specific primers of the format F1-UniTaq Bi-Q-UniTaq Ai. (where F1 is a fluorescent dye that is quenched by Quencher Q). Under these conditions, the following product will form:
F1-UniTaq Bi-Q-UniTaq Ai-Upstream Target-CGCG-Downstream Target-UniTaq Bi'-Univ.Primer U2'

This will hairpin, such that the UniTaq Bi sequence pairs with the UniTaq Bi' sequence. When Universal Primer U2 binds to the Univ.Primer U2' sequence, the 5'→3' exonuclease activity of polymerase digests the UniTaq Bi sequence, liberating the F1 fluorescent dye.

The above scheme may be performed using zipcode array or traditional Taqman detection. For example, the upstream probe need only contain a 5' Univ.Primer U1 followed by a zipcode sequence followed by target-specific upstream sequence. The downstream probe need only contain 5' of 20 base extra overhang, where 6-10 bases are complementary to 3' end of Univ.Primer U2' sequence, followed by target-specific downstream sequence—Univ.Primer U2'. The resultant product would be:
Univ.Primer U1Pm-Zipcode Zi-Upstream Target-CGCG-Downstream Target-Univ.Primer U2'

For detection using universal (zipcode) arrays, the Univ.Primer U2 would contain a reporter label, i.e. a fluorescent group, while the Univ.Primer U1 would contain a 5' phosphate, and amplification would continue for a total of about 30 to 40 cycles. This would allow for use of lambda exonuclease to digest the second strand, rendering the fluorescently labeled product single-stranded and suitable for hybridization on a universal (zipcode) array.

For detection using Taqman assays, after the 8-20 cycles of universal amplification, the sample would be diluted 10- to 100-fold and unique primers would be added that overlap with some or all of the unique zipcode sequence for each product. The Taqman probe would be for either the junction sequence of both zipcode and target DNA, or just the target DNA (without overlap of the unique primer in either case).

The second primer would still be the Univ.Primer U2, although for added specificity, it can also include some genome-specific bases (without overlap to the Taqman probe).

In addition, the above constructs can include unique sequence (ranging from 0 to 10 bases) internal to the Universal primers (Unique Ai, Unique Bi), represented as follows.
Univ.Primer U1-Unique Ai-Zipcode Zi-Upstream Target-CGCG-Downstream Target-Unique Bi-Univ.Primer U2'

For detection using Zipcode Taqman assays, after the 8-20 cycles of universal amplification, the sample would be diluted 10- to 100-fold and unique primers would be added that overlap with the Unique Ai the Unique Bi sequence for each product. The Taqman probe would be to the zipcode sequence.

The essence of the UniTaq approach is that both primers of a ligation event need to be correct in order to get a positive signal. This is currently achieved by requiring hybridization of two parts to each other (in the example above, F1-UniTaq Bi-Q region hybridizes to UniTaq BI' sequence). However, there are alternative approaches, using either zipcode arrays or zipcode Taqman assays.

One approach is to have the zipcode sequence split into two parts, which may be brought in proximity to each other using a short region of complementary sequence on both sides of the split parts. In the preferred embodiment, this short complementary region is from 5 to 8 bases. This allows for transient hairpin formation at the short region when the two sections are on the same single strand of DNA, which is stabilized by hybridizing both halves of the zipcode sequence to a full length complementary zipcode sequence on an array, or alternatively as part of a Taqman assay.

This approach would use upstream probes that contain a 5' Univ.Primer U1 followed by a first half zipcode sequence Zi.1 and a short sequence Ti followed by the upstream target. The downstream probes contain a 5' downstream target region, a short sequence Ti' followed by second half of zipcode sequence Zi.2 Univ.Primer U2'. The resultant product would be:
Univ.Primer U1-$1^{st}$ ½ Zipcode Zi.1-Short Ti-Upstream Target-CGCG-Downstream Target-Short Ti'-$2^{nd}$ ½ Zipcode Zi.2-Univ.Primer U2'

When the Short Ti transiently hybridizes to Short Ti', the $1^{st}$ ½ A Zipcode Zi sequence is brought in proximity to the $2^{nd}$ ½ Zipcode Zi, and the transient hybridization may be stabilized when hybridizing both Zipcode Zi half sequences to the full-length Zipcode Zi' sequence on a zipcode array.

When using a single primer containing the fluorescent group and quencher, the design may be similar to that used with UniTaq. For example the starting sequence would be of the form:
Univ.Primer U1-UniTaq Ai-$1^{st}$ ½ A Zipcode Zi.1-Short Ti-Upstream Target-CGCG-Downstream Target-Short Ti'-$2^{nd}$ ½ Zipcode Zi.2-Univ.Primer U2'

This would allow use of the F1-Zipcode Zi-Unique Ai and the common universal U2 primers for amplification (see FIG. 25.)

In addition, the above constructs can include unique sequence (ranging from 0 to 10 bases) internal to the Universal primers (Unique Ai, Unique Bi), represented as follows.
Univ.Primer U1-Unique Ai-$1^{st}$ ½ Zipcode Zi.1-Short Ti-Upstream Target-CGCG-Downstream Target-Short Ti'-$2^{nd}$ ½ Zipcode Zi.2-Unique Bi-Univ.Primer U2'

For detection using Zipcode Taqman assays, after the 8-20 cycles of universal amplification, the sample would be diluted 10- to 100-fold and unique primers would be added that overlap with the Unique Ai the Unique Bi sequence for each product. The Taqman probe would be to the full length zipcode sequence (see FIG. 24).

Since each junction sequence between the zipcode identifier and target sequence is unique, the products of the initial universal amplification may also be identified and quantified using next-generation sequencing.

Detailed Protocol for Highly Sensitive Detection of Methylation Marker (When Present at 1% to 0.01%):

An alternative approach to this problem is to use LDR probes that are coupled to each other through their non-ligating ends. This allows use of lower primer concentrations. Further, it provides a simple way to remove both upstream and downstream unligated probes from undergoing post-ligation reactions.

Optional Step 1: Cleave isolated genomic DNA, or methyl enriched DNA with the methyl sensitive enzyme BstUI. Preferably, two or three sites per promoter are chosen for determining methylation status. This step also would destroy any carryover contamination PCR amplicon (which would not be methylated).

Step 2: Denature genomic DNA from plasma (94° C. 1 minute) in the presence of coupled probes, comprising of upstream LDR probe portions (5' Univ.Primer U1-UniTaq Ai, followed by upstream target-specific sequence with a G base at the 3' end), coupled to the matched downstream LDR probe portions (5' G base or flap containing same G base followed by downstream target-specific sequence—UniTaq BI'-Univ.Primer U2'—and 6-10 bases target specific sequence complementary to the free 3' end of the upstream primer sequence portion), Taq polymerase, and thermostable ligase (preferably from strain AK16D). The above probe may be rewritten as (5' Flap containing G base followed by downstream target-specific sequence—UniTaq BI'-Univ.Primer U2'—and 6-10 bases target specific sequence complementary to the free 3' end of the upstream primer sequence portion, followed by an optional spacer, coupled to Univ.Primer U1-UniTaq Ai, followed by upstream target-specific sequence with a G base at the 3' end.) In this variation, the coupled probe can contain additional bases or just spacer, and optionally contain a region that polymerase does not copy through.

Step 3: Add hot start dNTP's Universal Primer U1, and Universal Primer U2, and BstUI. Incubate at 55° C. (allows BstUI to cleave unmethylated ligation products, and activates dNTPs) to allow unligated coupled probes to self-hairpin to the 6-10 bases that are complementary to 3' end, which extends to create longer hairpins that render these coupled probes refractory to further amplification. Then, allow PCR amplification to proceed for 8-20 cycles. In one variation, the universal primer tails U1 and U2 on the LDR compound probes are slightly shorter than Universal primers U1 and U2. This allows initial universal amplification at a lower cycling temperature (i.e. 55° C. annealing) followed by higher cycling temperature (i.e. 65° C. annealing) such that the universal primers U1 and U2 bind preferentially to the desired product (compared to composite LDR probes binding to incorrect products). Further the universal primers U1 and U2 contain a short sequence in common (i.e. 6-10 bases) to avoid primer dimer formation. These conditions amplify fragments of the sequence:
Univ.Primer U1-UniTaq Ai-Upstream Target-CGCG-Downstream Target-UniTaq Bi'-Univ.Primer U2'

Step 4: Open tube, dilute 10- to 100-fold and distribute aliquots to Taqman wells, each well containing the following primers: Universal Primer U2 and UniTaq specific primers of the format F1-UniTaq Bi-Q-UniTaq Ai. (where F1 is a fluorescent dye that is quenched by Quencher Q). Under these conditions, the following product will form:
F1-UniTaq Bi-Q-UniTaq Ai-Upstream Target-CGCG-Downstream Target-UniTaq Bi'-Univ.Primer U2'

This will hairpin, such that the UniTaq Bi sequence pairs with the UniTaq Bi' sequence. When Universal Primer U2 binds to the Univ.Primer U2' sequence, the 5'→3' exonuclease activity of polymerase digests the UniTaq Bi sequence, liberating the F1 fluorescent dye.

In a variation of the above, the matched downstream LDR probe portions, i.e. 5' G base or flap containing same G base followed by target-specific sequence—UniTaq BI'—do not include 6-10 bases of target specific sequence complementary to the free 3' end of the upstream primer sequence portion. This primer may be rewritten as (5' Flap containing G base followed by downstream target-specific sequence—UniTaq BI'-Univ.Primer U2', followed by an optional cleavable base, coupled to Univ.Primer U1-UniTaq Ai, followed by upstream target-specific sequence with a G base at the 3' end.) In this version, the connecting region contains an internal sequence that does not inhibit exonuclease digestion, but may be cleaved after an exonuclease digestion step, and prior to a polymerase amplification step. An example of such a sequence is use of a uracil base, which may be subsequently cleaved with uracil DNA glycosylase. In this example, after the ligation step, both Exonuclease I and Exonuclease III are added to digest all unligated coupled probe, as well as all input target DNA. After heat-killing the exonucleases, uracil DNA glycosylase is added to linearize the ligated primers for subsequent PCR amplification.

In both of the above variations, the coupled probes may be synthesized without one or both Univ.Primer U1 and/or Univ.Primer U2' sequences, or portions thereof, thus requiring the need for one or two bridge primers (Universal Primer U1-UniTaq Ai and Universal Primer U2-UniTaq Bi) during the universal PCR amplification step.

In both of the above variations, the coupled probes may be synthesized without (i) a spacer that polymerase does not copy through, or without (ii) an internal sequence that does not inhibit exonuclease digestion, but may be cleaved in a subsequent step. These modifications are designed to linearize the initial circular ligation product and/or prevent polymerase containing 5'→3' exonuclease activity from destroying its own extension product when PCR amplifying using either the universal primer U2, or the secondary oligonucleotide primer set that hybridize to the primary coupled oligonucleotide probes (or complements thereof). The problem may also be solved by using, when possible, a polymerase lacking the 5'-3' exonuclease activity during the initial universal primer amplification step, or by using secondary oligonucleotide primers complementary to the circular ligation product that contain modifications on the 5' end to render them refractory to the 5'→3' exonuclease activity of polymerase. Such 5' modifications include use of thiophosphate in the backbone linkage and/or use of 2'-O-methyl nucleotide analogues.

Highly sensitive methylation detection may be performed using Zipcode array, Zipcode Taqman or traditional Taqman detection as described above.

This approach would use upstream LDR probes (5' Zipcode Zi, followed by target-specific sequence with a G base at the 3' end), coupled to the matched downstream LDR primers (5' G base followed by target-specific sequence—Univ.Primer U2'—and 6-10 bases target specific sequence complementary to the free 3' end of the upstream primer sequence). After universal PCR amplification, these conditions amplify fragments of the sequence:
Univ.Primer U1-Zipcode Zi-Upstream Target-CGCG-Downstream Target-Univ.Primer U2'

For detection using universal (zipcode) arrays, the Univ.Primer U2 would contain a reporter label, i.e. a fluorescent group, while the Univ.Primer U1 would contain a 5' phosphate, and amplification would continue for a total of about 30 to 40 cycles. This would allow for use of lambda exonuclease to digest the second strand, rendering the fluorescently labeled product single-stranded and suitable for hybridization on a universal (zipcode) array.

Highly sensitive methylation detection may be performed using split Zipcode sequences as described supra.

This approach would use upstream LDR probes (5' Universal Primer U1, a first half zipcode sequence Zi.1 and a short sequence Ti, followed by target-specific sequence with a G base at the 3' end), coupled to the matched downstream LDR probes (5' G base followed by target-specific sequence—the complement of the short sequence Ti', a second half zipcode sequence Zi.2-Univ.Primer U2'—and 6-10 bases target specific sequence complementary to the free 3' end of the upstream primer sequence). After universal PCR amplification, these conditions amplify fragments of the sequence:
Univ.Primer U1-$1^{st}$ ½ Zipcode Zi.1-Short Ti-Upstream Target-CGCG-Downstream Target-Short Ti'-$2^{nd}$ ½ Zipcode Zi.2-Univ.Primer U2'

When the Short Ti transiently hybridizes to Short Ti', the $1^{st}$ ½ Zipcode Zi.1 sequence is brought in proximity to the $2^{nd}$ ½ Zipcode Zi.2, and the transient hybridization may be stabilized when hybridizing both Zipcode Zi half sequences to the full-length Zipcode Zi' sequence on a zipcode array.

In addition, the above constructs can include unique sequence (ranging from 0 to 10 bases) internal to the Universal primers (Unique Ai, Unique Bi), represented as follows.
Univ.Primer U1-Unique Ai-$1^{st}$ ½ Zipcode Zi.1-Short Ti-Upstream Target-CGCG-Downstream Target-Short Ti'-$2^{nd}$ ½ Zipcode Zi.2-Unique Bi-Univ.Primer U2'

For detection using Zipcode Taqman assays, after the 8-20 cycles of universal amplification, the sample would be diluted 10- to 100-fold and unique primers would be added that overlap with the Unique Ai the Unique Bi sequence for each product. The Taqman probe would be to the full-length zipcode sequence.

Since each junction sequence between the target sequences is unique, the products of the initial universal amplification may also be identified and quantified using next-generation sequencing.

Overview of Second Approach—Methylation Sensitive Restriction Enzyme Digestion-Ligation:

This approach depends on the fidelity of two enzymes: (i) the restriction activity of BstUI, and (ii) the ligase in discriminating a match from mismatch on the 3' side of the upstream primer. Isolated genomic DNA, or methyl enriched DNA is treated with the methyl sensitive enzyme BstUI. Hybridization of two probes to a hemi-methylated target (i.e. 5' CGC*G 3') allows for cleavage of the flap by fresh BstUI, followed by ligation with ligase. Optional use of methylated C*G on 3' end prevents recleavage with BstUI. If the target was not methylated, BstUI will cleave both strands, and thermostable ligase will not reseal these fragments. Those products that are not cleaved will be amplified in a subsequent PCR amplification step, and thus this is the key discriminatory step.

By insisting on having the restriction endonuclease generate the 5' phosphate, this avoids false signal, and should get rid of any non-specific ligation signal as well. Thus, any rare fragment of genomic DNA that was single-stranded after purification, or did not get cleaved will not form a productive substrate for subsequent PCR amplifications, as the product has non-genomic sequences on both sides.

To summarize the levels of discrimination of the above approach for detection of low-abundance methylation (see FIGS. 5A-5H):
1. Use of methylation sensitive BstUI restriction enzymes to cleave double-stranded target when not methylated.
2. Use of methylation sensitive BstUI restriction enzymes to nick double-stranded target on downstream probe when original genomic DNA was hemi-methylated.
3. Use of 3' ligation fidelity of thermostable ligase on upstream probe.
4. Reuse of methylation sensitive BstUI restriction enzymes to cleave double-stranded target when original genomic DNA was not methylated.
5. Use of sequences on the 5' end of downstream probe, such that when they are not cleaved, form hairpins at lower temperature and extend on themselves to form products that do not amplify.

An advantage of this second approach is that if the target is missing the BstUI site, the downstream probe will not be nicked, so the 5' phosphate is not unmasked, so no ligation takes place, and consequently no false amplification can take place.

A disadvantage of this second approach is a high percentage of the given BstUI site is fully methylated, then there will be less signal since fully methylated target strand would inhibit BstUI nicking of the downstream primer.

An alternative approach (see below), using coupled matched upstream and downstream probes is also presented.

There are two variations to consider. In the first variation (shown in FIGS. 6A-6H), the coupled probes are designed to form hairpins at lower temperature and extend on themselves to form products that do not amplify.

To summarize the levels of discrimination of the first variation using coupled primers for detection of each BstUI methylated site:
1. Use of methylation sensitive BstUI restriction enzymes to cleave double-stranded target when not methylated.
2. Use of methylation sensitive BstUI restriction enzymes to nick double-stranded target on downstream probe when original genomic DNA was hemi-methylated.
3. Use of 3' ligation fidelity of thermostable ligase on upstream probe.
4. Reuse of methylation sensitive BstUI restriction enzymes to cleave double-stranded target when original genomic DNA was not methylated.
5. Use of lower probe concentrations to minimize target-independent events.
6. Use of sequences on the coupled probes, such that when they are not ligated, form hairpins at lower temperature and extend on themselves to form products that do not amplify.

In the second variation (FIGS. 6I-6N), the coupled probes are ligated to form a closed circle on the target, and unligated coupled probes (as well as input template DNA) are removed by exonuclease digestion.

To summarize the levels of discrimination of the first variation using coupled primers for detection of each BstUI methylated site:
1. Use of methylation sensitive BstUI restriction enzymes to cleave double-stranded target when not methylated.
2. Use of methylation sensitive BstUI restriction enzymes to nick double-stranded target on downstream probe when original genomic DNA was hemi-methylated.
3. Use of 3' ligation fidelity of thermostable ligase on upstream probe.
4. Reuse of methylation sensitive BstUI restriction enzymes to cleave double-stranded target when original genomic DNA was not methylated.
5. Use of lower probe concentrations to minimize target-independent events.
6. Use of exonucleases to destroy unligated probe and target.

As a control for the total amount of DNA present, one can choose a nearby target region that is methylated in normal DNA from the plasma or serum, and/or in an imprinted gene where at least one chromosome is always methylated. The upstream oligonucleotide probe that is ligated to the downstream probe is a mixture of two oligos: (i) An oligonucleotide present at 1 in 100 with the correct UniTaq specific sequence, and (ii) an oligonucleotide present at 99 in 100 with a sequence that does not contain the correct UniTaq specific sequence and optionally has about 6-10 bases complementary to its 3' end. The ligation product containing the UniTaq sequences amplifies and will give a signal equivalent to 1 in 100 of the original template. The majority ligation product lacks the universal sequence on the 5' end, and does not amplify exponentially. Unligated upstream probe will form a hairpin back on itself, and extend its own 3' sequence on itself, taking it out of contention for becoming part of another PCR amplicon.

As a control for the total amount of DNA present, this approach may also be used with coupled probes, again on a target region as described above. One uses a mixture of two oligonucleotides: (i) An oligonucleotide present at 1 in 100 with the correct UniTaq and/or other tag sequence, and (ii) an oligonucleotide present at 99 in 100 with a sequence that either lacks or has incorrect tag sequences. The ligation product containing the UniTaq and/or tag sequences amplifies and will give a signal equivalent to 1 in 100 of the original template. The majority of ligation product either lacks or has incorrect tag sequences, and does not amplify exponentially.

Detailed Protocol for Highly Sensitive Detection of Methylation Earker (when Present at 1% to 0.01%):

Optional Step 1: Cleave isolated genomic DNA, or methyl enriched DNA with the methyl sensitive enzyme BstUI. Preferably, two or three sites per promoter are chosen for determining methylation status. This step also would destroy any carryover contamination PCR amplicon (which would not be methylated).

Step 2: Denature genomic DNA from plasma (94° C. 1 minute) in the presence of upstream LDR probes (5' Universal Primer U1, followed by UniTaq Ai, followed by target-specific sequence, and CpG bases at the 3' end), downstream LDR probes (5' of 20 base extra overhang, where 6-10 bases are complementary to 3' end of Univ.Primer U2' sequence, the BstUI sequence, followed by target-specific sequence—UniTaq Bi'-Univ.Primer U2') and allow probes to hybridize to target. Add BstUI and thermostable ligase (preferably from strain AK16D). Perform one or more LDR reactions. Optional use of methylated C*G on 3' end prevents recleavage with BstUI.

Step 3: Add Taq polymerase, dNTP's, Universal Primer U1, and Universal Primer U2. Activate polymerase. Incubate at 55° C. to allow unligated downstream probes to self-hairpin to the 6-10 bases that are complementary to 3' end, which extends to create longer hairpins that render these downstream probes refractory to further amplification. Then, allow PCR amplification to proceed for 8-20 cycles. In one variation, the universal primer tails U1 and U2 on the LDR compound primers are slightly shorter than Universal primers U1 and U2. This allows initial universal amplification at a lower cycling temperature (i.e. 55° C. annealing) followed by higher cycling temperature (i.e. 65° C. annealing) such that the universal primers U1 and U2 bind preferentially to the desired product (compared to composite LDR primers binding to incorrect products). Further the universal primers U1 and U2 contain a short sequence in common (i.e. 6-10 bases) to avoid primer dimer formation. These conditions amplify fragments of the sequence:
Univ.Primer U1-UniTaq Ai-Upstream Target-CGCG-Downstream Target-UniTaq Bi'-Univ.Primer U2'

Step 4: Open tube, dilute 10- to 100-fold and distribute aliquots to Taqman wells, each well containing the following primers: Universal Primer U2 and UniTaq specific primers of the format F1-UniTaq Bi-Q-UniTaq Ai. (where F1 is a fluorescent dye that is quenched by Quencher Q). Under these conditions, the following product will form:
F1-UniTaq Bi-Q-UniTaq Ai-Upstream Target-CGCG-Downstream Target-UniTaq Bi'-Univ.Primer U2'

This will hairpin, such that the UniTaq Bi sequence pairs with the UniTaq Bi' sequence. When Universal Primer U2 binds to the Univ.Primer U2' sequence, the 5'→3' exonuclease activity of polymerase digests the UniTaq Bi sequence, liberating the F1 fluorescent dye.

Highly sensitive methylation detection may be performed using Zipcode array, Zipcode Taqman or traditional Taqman detection as described supra. This approach would use upstream LDR probes (5' Universal Primer U1, followed by Zipcode Zi, followed by target-specific sequence with a G base at the 3' end), and downstream LDR probes (5' of 20 base extra overhang, where 6-10 bases are complementary to 3' end of Univ.Primer U2' sequence, the BstUI sequence, followed by target-specific sequence—Univ.Primer U2'). After universal PCR amplification, these conditions amplify fragments of the sequence:
Univ.Primer U1-Zipcode Zi-Upstream Target-CGCG-Downstream Target-Univ.Primer U2'

For detection using universal (zipcode) arrays, the Univ.Primer U2 would contain a reporter label, i.e. a fluorescent group, while the Univ.Primer U1 would contain a 5' phosphate, and amplification would continue for a total of about 30 to 40 cycles. This would allow for use of lambda exonuclease to digest the second strand, rendering the fluorescently labeled product single-stranded and suitable for hybridization on a universal (zipcode) array.

Highly sensitive methylation detection may be performed using split Zipcode sequences as described supra. This approach would use upstream LDR probes (5' Universal Primer U1, a first half zipcode sequence Zi.1 and a short sequence Ti, followed by target-specific sequence with CpG bases at the 3' end), and downstream LDR probes (5' of 20 base extra overhang, where 6-10 bases are complementary to 3' end of Univ.Primer U2' sequence, followed by the BstUI sequence, followed by target-specific sequence—the complement of the short sequence Ti', a second half zipcode sequence Zi.2-Univ.Primer U2'). After universal PCR amplification, these conditions amplify fragments of the sequence:
Univ.Primer U1-$1^{st}$ ½ Zipcode Zi.1-Short Ti-Upstream Target-CGCG-Downstream Target-Short Ti'-$2^{nd}$ ½ Zipcode Zi.2-Univ.Primer U2'

When the Short Ti transiently hybridizes to Short Ti', the $1^{st}$ ½ Zipcode Zi.1 sequence is brought in proximity to the $2^{nd}$ ½ Zipcode Zi.2, and the transient hybridization may be stabilized when hybridizing both Zipcode Zi half sequences to the full-length Zipcode Zi' sequence on a zipcode array.

In addition, the above constructs can include unique sequence (ranging from 0 to 10 bases) internal to the Universal primers (Unique Ai, Unique Bi), represented as follows.
Univ.Primer U1-Unique Ai-$1^{st}$ ½ Zipcode Zi.1-Short Ti-Upstream Target-CGCG-Downstream Target-Short Ti'-$2^{nd}$ ½ Zipcode Zi.2-Unique Bi-Univ.Primer U2'

For detection using Zipcode Taqman assays, after the 8-20 cycles of universal amplification, the sample would be diluted 10- to 100-fold and unique primers would be added that overlap with the Unique Ai the Unique Bi sequence for each product. The Taqman probe would be to the full length zipcode sequence.

Since each junction sequence between the target sequences is unique, the products of the initial universal amplification may also be identified and quantified using next-generation sequencing.

Detailed Protocol for Highly Sensitive Detection of Methylation Marker (when Present at 1% to 0.01%):

An alternative approach to this problem is to use LDR probes that are coupled to each other through their non-ligating ends. This allows use of lower probe concentrations. Further, it provides a simple way to remove both upstream and downstream unligated probers from undergoing post-ligation reactions.

Optional step 1: Cleave isolated genomic DNA, or methyl enriched DNA with the methyl sensitive enzyme BstUI. Preferably, two or three sites per promoter are chosen for determining methylation status. This step also would destroy any carryover contamination PCR amplicon (which would not be methylated).

Step 2: Denature genomic DNA from plasma (94° C. 1 minute) in the presence of coupled probes, comprising of upstream LDR probe portions (5' Univ.Primer U1-UniTaq Ai, followed by target-specific sequence with CpG bases at the 3' end), coupled to the matched downstream LDR probe portions (5' region containing the BstUI sequence, followed by target-specific sequence—UniTaq BI'-Univ.Primer U2'—and 6-10 bases target specific sequence complementary to the free 3' end of the upstream primer sequence portion), and allow probers to hybridize to target. Add BstUI and thermostable ligase (preferably from strain AK16D). The above probe may be rewritten as (5' region containing the BstUI sequence, followed by downstream target-specific sequence—UniTaq BI'-Univ.Primer U2'—and 6-10 bases target specific sequence complementary to the free 3' end of the upstream primer sequence portion, followed by an optional spacer, coupled to Univ.Primer U1-UniTaq Ai, followed by upstream target-specific sequence with a CpG dinucleotide at the 3' end.) Perform one or more LDR reactions. Optional use of methylated C*G dinucleotide on 3' end prevents recleavage with BstUI. In this variation, the coupled probe can contain additional bases or just spacer, and optionally contain a region that polymerase does not copy through.

Step 3: Add Taq polymerase, dNTP's, Universal Primer U1, and Universal Primer U2. Activate polymerase. Incubate at 55° C. to allow unligated coupled probers to self-hairpin to the 6-10 bases that are complementary to 3' end, which extends to create longer hairpins that render these coupled probes refractory to further amplification. Then, allow PCR amplification to proceed for 8-20 cycles. In one variation, the universal primer tails U1 and U2 on the LDR compound probes are slightly shorter than Universal primers U1 and U2. This allows initial universal amplification at a lower cycling temperature (i.e. 55° C. annealing) followed by higher cycling temperature (i.e. 65° C. annealing) such that the universal primers U1 and U2 bind preferentially to the desired product (compared to composite LDR probes binding to incorrect products). Further the universal primers U1 and U2 contain a short sequence in common (i.e. 6-10 bases) to avoid primer dimer formation. These conditions amplify fragments of the sequence:
Univ.Primer U1-UniTaq Ai-Upstream Target-CGCG-Downstream Target-UniTaq Bi'-Univ.Primer U2'

Step 4: Open tube, dilute 10- to 100-fold and distribute aliquots to Taqman wells, each well containing the following primers: Universal Primer U2 and UniTaq specific primers of the format F1-UniTaq Bi-Q-UniTaq Ai. (where F1 is a fluorescent dye that is quenched by Quencher Q). Under these conditions, the following product will form:
F1-UniTaq Bi-Q-UniTaq Ai-Upstream Target-CGCG-Downstream Target-UniTaq Bi'-Univ.Primer U2'

This will hairpin, such that the UniTaq Bi sequence pairs with the UniTaq Bi' sequence. When Universal Primer U2 binds to the Univ.Primer U2' sequence, the 5'→3' exonuclease activity of polymerase digests the UniTaq Bi sequence, liberating the F1 fluorescent dye.

In a variation of the above, the matched downstream LDR probe portions, i.e. 5' G base or flap containing same G base followed by target-specific sequence—UniTaq BI'—do not include 6-10 bases of target specific sequence complementary to the free 3' end of the upstream primer sequence portion. This probe may be rewritten as (5' region containing the BstUI sequence, followed by downstream target-specific sequence—UniTaq BI'-Univ.Primer U2', followed by an optional cleavable base, coupled to Univ.Primer U1-UniTaq Ai, followed by upstream target-specific sequence with a CpG dinucleotide at the 3' end). Optional use of methylated C*G dinucleotide on 3' end prevents recleavage with BstUI. In this version, the connecting region contains an internal sequence that does not inhibit exonuclease digestion, but may be cleaved after an exonuclease digestion step, and prior to a polymerase amplification step. An example of such a sequence is use of a uracil base, which may be subsequently cleaved with uracil DNA glycosylase. In this example, after the ligation step, both Exonuclease I and Exonuclease III are added to digest all unligated coupled probe, as well as all input target DNA. After heat-killing the exonucleases, uracil DNA glycosylase is added to linearize the ligated primers for subsequent PCR amplification.

In both of the above variation, the coupled primers may be synthesized without one or both Univ.Primer U1 and/or Univ.Primer U2' sequences, or portions thereof, thus requiring the need for one or two bridge primers (Universal Primer U1-UniTaq Ai and Universal Primer U2-UniTaq Bi) during the universal PCR amplification step.

In both of the above variations, the coupled probes may be synthesized without (i) a spacer that polymerase does not copy through, or without (ii) an internal sequence that does not inhibit exonuclease digestion, but may be cleaved in a subsequent step. These modifications are designed to linearize the initial circular ligation product and/or prevent polymerase containing 5'→3' exonuclease activity from destroying its own extension product when PCR amplifying using either the universal primer U2, or the secondary oligonucleotide primer set that hybridize to the primary coupled oligonucleotide probes (or complements thereof). The problem may also be solved by using, when possible, a polymerase lacking the 5'-3' exonuclease activity during the initial universal primer amplification step, or by using secondary oligonucleotide primers complementary to the circular ligation product that contain modifications on the 5' end to render them refractory to the 5'→3' exonuclease activity of polymerase. Such 5' modifications include use of thiophosphate in the backbone linkage and/or use of 2'-O-methyl nucleotide analogues.

Highly sensitive methylation detection may be performed using Zipcode array, Zipcode Taqman or traditional Taqman detection as described supra. This approach would use upstream LDR primers (5' Zipcode Zi, followed by target-specific sequence with C*G bases at the 3' end), coupled to the matched downstream LDR primers (5' region containing the BstUI sequence, followed by target-specific sequence—Univ.Primer U2'—and 6-10 bases target specific sequence complementary to the free 3' end of the upstream primer sequence). After universal PCR amplification, these conditions amplify fragments of the sequence:
Univ.Primer U1-Zipcode Zi-Upstream Target-CGCG-Downstream Target-Univ.Primer U2'

For detection using universal (zipcode) arrays, the Univ.Primer U2 would contain a reporter label, i.e. a fluorescent group, while the Univ.Primer U1 would contain a 5' phosphate, and amplification would continue for a total of about 30 to 40 cycles. This would allow for use of lambda exonuclease to digest the second strand, rendering the fluorescently labeled product single-stranded and suitable for hybridization on a universal (zipcode) array.

Highly sensitive methylation detection may be performed using split Zipcode sequences as described supra. This approach would use upstream LDR probes (5' Universal Primer U1, a first half zipcode sequence Zi.1 and a short sequence Ti, followed by target-specific sequence with C*G bases at the 3' end), coupled to the matched downstream LDR primers (5' region containing the BstUI sequence, followed by target-specific sequence—the complement of the short sequence Ti', a second half zipcode sequence Zi.2-Univ.Primer U2'—and 6-10 bases target specific sequence complementary to the free 3' end of the upstream primer sequence). After universal PCR amplification, these conditions amplify fragments of the sequence:
Univ.Primer U1-$1^{st}$ ½ Zipcode Zi.1-Short Ti-Upstream Target-CGCG-Downstream Target-Short Ti'-$2^{nd}$ ½ Zipcode Zi.2-Univ.Primer U2'

When the Short Ti transiently hybridizes to Short Ti', the $1^{st}$ ½ Zipcode Zi.1 sequence is brought in proximity to the $2^{nd}$ ½ Zipcode Zi.2, and the transient hybridization may be stabilized when hybridizing both Zipcode Zi half sequences to the full-length Zipcode Zi' sequence on a zipcode array.

In addition, the above constructs can include unique sequence (ranging from 0 to 10 bases) internal to the Universal primers (Unique Ai, Unique Bi), represented as follows.
Univ.Primer U1-Unique Ai-$1^{st}$ ½ Zipcode Zi-Short Ci-Upstream Target-CGCG-Downstream Target-Short Ci'-$2^{nd}$ ½ Zipcode Zi-Unique Bi-Univ.Primer U2'

For detection using Zipcode Taqman assays, after the 8-20 cycles of universal amplification, the sample would be diluted 10- to 100-fold and unique primers would be added that overlap with the Unique Ai the Unique Bi sequence for each product. The Taqman probe would be to the full-length zipcode sequence.

Since each junction sequence between the target sequences is unique, the products of the initial universal amplification may also be identified and quantified using next-generation sequencing.

The same principles on the BstUI site may also be applied to other restriction endonucleases that nick the unmethylated strand of a duplex where the genomic target strand is methylated. Below are some examples of enzymes that may meet this requirement.

AciI=3.5 base cutter, C^CGC and G^CGG
HinP1I=4 base, G^CGC
HpyCH4IV=4 base, A^CGT FIGS. 7A-7H are similar to FIGS. 5A-5H, except using the HinP1I restriction enzyme. The other difference is that HinP1I is a mesophilic restriction enzyme. So it becomes thermally inactivated during the process of heating the hybridized probe target complex to about 60° C. for the ligation step. Thus, this approach is not amenable to multiple cycles of ligation. On the other hand, use of a mesophilic restriction enzyme obviates the need to modify the upstream probe on the 3' end so that the ligation product is resistant to re-nicking. The other difference is that BstUI gives a blunt cleavage of unmethylated target, while HinP1I leaves a 2 base 5' overhang. However, thermostable ligase will not ligate either blunt end or the two-base overhang.

FIGS. 8A-8H are similar to FIGS. 6A-6H, except using the HinP1I restriction enzyme. Again, since the enzyme is mesophilic, it is inactivated during the step of warming the reaction for optimal ligation conditions.

In both examples illustrated here, the downstream probe contains a restriction site that is nicked to liberate a ligation competent 5' end. However, the probes could also be designed so that a cleavable restriction site is on the 3' end (that is blocked or mismatched), liberating a ligation competent free 3'-OH. Finally, it is recognized that both probes may be ligation incompetent, and the reactive groups are liberated sequentially using the same enzyme on methylated genomic DNA.

Overview of Third Approach: Methylation Sensitive Restriction Enzyme Digestion-Ligation Reaction:

This approach depends on the activity of three enzymes: (i) the restriction activity of HinP1I, (ii) the extension activity of polymerase and (iii) the sealing activity of ligase. Isolated genomic DNA, or methyl enriched DNA is treated with the methyl sensitive enzyme HinP1I. Hybridization of two probes to a target containing adjacent methylated HinP1I sequence (i.e. 5' GC*GC 3') allows for cleavage of the 3' hairpin of the first probe and the 5' flap of the second probe by HinP1I. The liberated 3'OH of the upstream primer is extended by polymerase lacking 5'-3' nuclease or strand displacing activity, followed by ligation to the downstream primer with ligase. Unligated probes form hairpins via hybridization between complementary regions, and are extended by polymerase to occlude binding of, and subsequent extension or amplification by, the secondary primers.

By insisting on having the restriction endonuclease generate both the 3'OH and the 5' phosphate, this avoids false signal, and should get rid of any non-specific ligation signal as well. Thus, any rare fragment of genomic DNA that was single-stranded after purification, or did not get cleaved will not form a productive substrate for subsequent PCR amplifications, as the product has non-genomic sequences on both sides.

To summarize the levels of discrimination of the above approach for detection of low-abundance methylation (see FIGS. 9A-9F):

1. Use of methylation sensitive HinP1I restriction enzymes to cleave double-stranded target when not methylated.
2. Use of methylation sensitive HinP1I restriction enzymes to nick double-stranded target on both upstream and downstream probes when original genomic DNA was methylated.
3. Use of 3' ligation fidelity of thermostable ligase on upstream probe.
4. Reuse of methylation sensitive HinP1I restriction enzymes to cleave double-stranded target when original genomic DNA was not methylated.
5. Use of sequences on the 3' end of upstream probe and the 5' end of downstream probe, such that when they are not cleaved, form hairpins at lower temperature and extend on themselves to form products that do not amplify.

An advantage of this approach is that if the target is missing either HinP1I site or alternatively either one is not methylated, the upstream probe will not be nicked, preventing polymerase from extending the liberated 3' OH, or the downstream probe will not be nicked, so the 5' phosphate is not unmasked, so no ligation takes place, and consequently no false amplification can take place.

An alternative approach (see below), using coupled matched upstream and downstream probes is also presented. There are two variations to consider. In the first variation, (shown in FIGS. 10A-10F), the coupled probes are designed to form hairpins at lower temperature and extend on themselves to form products that do not amplify.

To summarize the levels of discrimination of the first variation using coupled primers for detection of each HinP1I methylated site:

1. Use of methylation sensitive HinP1I restriction enzymes to cleave double-stranded target when not methylated.
2. Use of methylation sensitive HinP1I restriction enzymes to nick double-stranded target on both upstream and downstream probes when original genomic DNA was methylated.
3. Use of 3' ligation fidelity of thermostable ligase on upstream probe.
4. Reuse of methylation sensitive HinP1I restriction enzymes to cleave double-stranded target when original genomic DNA was not methylated.
5. Use of lower probe concentrations to minimize target-independent events.
6. Use of sequences on the coupled probes, such that when they are not ligated, form hairpins at lower temperature and extend on themselves to form products that do not amplify.

In the second variation (FIGS. 10G-10J), the coupled probes are ligated to form a closed circle on the target, and unligated coupled primers (as well as input template DNA) are removed by exonuclease digestion.

To summarize the levels of discrimination of the second variation using coupled primers for detection of each HinP1I methylated site:

1. Use of methylation sensitive HinP1I restriction enzymes to cleave double-stranded target when not methylated.
2. Use of methylation sensitive HinP1I restriction enzymes to nick double-stranded target on both upstream and downstream probes when original genomic DNA was methylated.
3. Use of 3' ligation fidelity of thermostable ligase on upstream probe.
4. Reuse of methylation sensitive HinP1I restriction enzymes to cleave double-stranded target when original genomic DNA was not methylated.
5. Use of lower probe concentrations to minimize target-independent events.
6. Use of exonucleases to destroy unligated probes and target As a control for the total amount of DNA present (see FIGS. 11A-11F), one can choose a nearby target region that is methylated in normal DNA from the plasma or serum, and/or in an imprinted gene where at least one chromosome is always methylated. The upstream oligonucleotide probe that is ligated to the downstream probe is a mixture of two oligos: (i) An oligonucleotide present at 1 in 100 with the correct UniTaq specific sequence, and (ii) an oligonucleotide present at 99 in 100 with a sequence that does not contain the correct UniTaq specific sequence and optionally has about 6-10 bases complementary to its 3' end. The ligation product containing the UniTaq sequences amplifies and will give a signal equivalent to 1 in 100 of the original template. The majority ligation product lacks the universal sequence on the 5' end, and does not amplify exponentially. Unligated upstream probe will form a hairpin back on itself, and extend its own 3' sequence on itself, taking it out of contention for becoming part of another PCR amplicon.

As a control for the total amount of DNA present, this approach may also be used with coupled probes, again on a target region as described above. One uses a mixture of two oligonucleotides: (i) An oligonucleotide present at 1 in 100 with the correct UniTaq and/or other tag sequence, and (ii) an oligonucleotide present at 99 in 100 with a sequence that either lacks or has incorrect tag sequences. The ligation product containing the UniTaq and/or tag sequences amplifies and will give a signal equivalent to 1 in 100 of the original template. The majority of ligation product either lacks or has incorrect tag sequences, and does not amplify exponentially.

Detailed Protocol for Highly Sensitive Detection of Methylation Marker (when Present at 1% to 0.01%):

Optional Step 1: Cleave isolated genomic DNA, or methyl enriched DNA with the methyl sensitive enzyme HinP1I. Preferably, two or three sites per promoter are chosen for determining methylation status. This step also would destroy any carryover contamination PCR amplicon (which would not be methylated).

Step 2: Denature genomic DNA from plasma (94° C. 1 minute) in the presence of upstream LDR probes (5' Universal Primer U1, followed by UniTaq Ai, followed by target-specific sequence, the HinP1I sequence and a small hairpin at the 3' end), downstream LDR probes (5' of 20 base extra overhang, where 6-10 bases are complementary to 3' end of Univ.Primer U2' sequence, the HinP1I sequence, followed by target-specific sequence—UniTaq Bi'—Univ.Primer U2') and allow probes to hybridize to target. Add HinP1I, dNTPs thermostable polymerase that preferably lacks 5'-3' exonuclease or strand displacement activity and thermostable ligase (preferably from strain AK16D). After cleavage with HinP1I at 37° C., raise temperature to denature endonuclease while allowing polymerase to extend and ligase to covalently seal the two free ends.

Step 3: Add Universal Primer U1, Universal Primer U2, and optional Taq Polymerase. Incubate at 55° C. to allow both unligated upstream and downstream probes to self-hairpin to the 6-10 bases that are complementary to 3' end, which extends to create longer hairpins that render these downstream probe refractory to further amplification. Then allow PCR amplification to proceed for 8-20 cycles. In one variation, the universal primer tails U1 and U2 on the LDR compound probes are slightly shorter than Universal primers U1 and U2. This allows initial universal amplification at a lower cycling temperature (i.e. 55° C. annealing) followed by higher cycling temperature (i.e. 65° C. annealing) such that the universal primers U1 and U2 bind preferentially to the desired product (compared to composite LDR probes binding to incorrect products). Further the universal primers U1 and U2 contain a short sequence in common (i.e. 6-10 bases) to avoid primer dimer formation. These conditions amplify fragments of the sequence:

Univ.Primer U1-UniTaq Ai-Upstream Target-GCGC-Downstream Target-UniTaq Bi'-Univ.Primer U2'

Step 4: Open tube, dilute 10- to 100-fold and distribute aliquots to Taqman wells, each well containing the following primers: Universal Primer U2 and UniTaq specific primers of the format F1-UniTaq Bi-Q-UniTaq Ai (where F1 is a fluorescent dye that is quenched by Quencher Q). Under these conditions, the following product will form:

F1-UniTaq Bi-Q-UniTaq Ai-Upstream Target-GCGC-Downstream Target-UniTaq Bi'-Univ.Primer U2'

This will hairpin, such that the UniTaq Bi sequence pairs with the UniTaq Bi' sequence. When Universal Primer U2 binds to the Univ.Primer U2' sequence, the 5'→3' exonuclease activity of polymerase digests the UniTaq Bi sequence, liberating the F1 fluorescent dye.

Highly sensitive methylation detection may be performed using Zipcode array, Zipcode Taqman or traditional Taqman detection as described supra. This approach would use upstream LDR probes (5' Universal Primer U1, followed by Zipcode Zi, followed by target-specific sequence, followed by the HinP1I sequence and a small hairpin at the 3' end), and downstream LDR probes (5' of 20 base extra overhang, where 6-10 bases are complementary to 3' end of Univ.Primer U2' sequence, the HinP1I sequence, followed by target-specific sequence—Univ.Primer U2'). After universal PCR amplification, these conditions amplify fragments of the sequence:

Univ.Primer U1-Zipcode Zi-Upstream Target-GCGC-Downstream Target-Univ.Primer U2'

For detection using universal (zipcode) arrays, the Univ.Primer U2 would contain a reporter label, i.e. a fluorescent group, while the Univ.Primer U1 would contain a 5' phosphate, and amplification would continue for a total of about 30 to 40 cycles. This would allow for use of lambda exonuclease to digest the second strand, rendering the fluorescently labeled product single-stranded and suitable for hybridization on a universal (zipcode) array.

Highly sensitive methylation detection may be performed using split Zipcode sequences as described supra. This approach would use upstream LDR probes (5' Universal Primer U1, a first half zipcode sequence Zi.1 and a short sequence Ti, followed by target-specific sequence, followed by the HinP1I sequence and a small hairpin at the 3' end), and downstream LDR primers (5' of 20 base extra overhang, where 6-10 bases are complementary to 3' end of Univ.Primer U2' sequence, followed by the HinP1I sequence, followed by target-specific sequence—the complement of the short sequence Ti', a second half zipcode sequence Zi.2-Univ.Primer U2'). After universal PCR amplification, these conditions amplify fragments of the sequence:

Univ.Primer U1-$1^{st}$ ½ Zipcode Zi.1-Short Ti-Upstream Target-GCGC-Downstream Target-Short Ti'-$2^{nd}$ ½ Zipcode Zi.2-Univ.Primer U2'

When the Short Ti transiently hybridizes to Short Ti', the $1^{st}$ ½ Zipcode Zi.1 sequence is brought in proximity to the $2^{nd}$ ½ Zipcode Zi.2, and the transient hybridization may be stabilized when hybridizing both Zipcode Zi half sequences to the full-length Zipcode Zi' sequence on a zipcode array.

In addition, the above constructs can include unique sequence (ranging from 0 to 10 bases) internal to the Universal primers (Unique Ai, Unique Bi), represented as follows.

Univ.Primer U1-Unique Ai-1$^{st}$ ½ Zipcode Zi.1-Short Ti-Upstream Target-GCGC-Downstream Target-Short Ti'-2$^{nd}$ ½ Zipcode Zi.2-Unique Bi-Univ.Primer U2'

For detection using Zipcode Taqman assays, after the 8-20 cycles of universal amplification, the sample would be diluted 10- to 100-fold and unique primers would be added that overlap with the Unique Ai the Unique Bi sequence for each product. The Taqman probe would be to the full-length zipcode sequence.

Since each junction sequence between the target sequences is unique, the products of the initial universal amplification may also be identified and quantified using next-generation sequencing.

Detailed Protocol for Highly Sensitive Detection of Methylation Marker (when Present at 1% to 0.01%):

An alternative approach is to use LDR probes that are coupled to each other through their non-ligating ends. This allows use of lower primer concentrations. Further, it provides a simple way to remove both upstream and downstream unligated probes from undergoing post-ligation reactions.

Optional Step 1: Cleave isolated genomic DNA, or methyl enriched DNA with the methyl sensitive enzyme HinP1I. Preferably, two or three sites per promoter are chosen for determining methylation status. This step also would destroy any carryover contamination PCR amplicon (which would not be methylated).

Step 2: Denature genomic DNA from plasma (94° C. 1 minute) in the presence of coupled probes, comprising of upstream LDR probe portions (5' Univ.Primer U1-UniTaq Ai, followed by target-specific sequence, the HinP1I sequence, followed by one or more bases that mismatch to the target at the 3' end), coupled to the matched downstream LDR probe portions (5' region containing the HinP1I sequence, followed by target-specific sequence—UniTaq BI'-Univ.Primer U2'—and 6-10 bases sequence complementary to the free 3' end of the uncleaved upstream primer sequence portion, and optionally 6-10 bases target specific sequence complementary to the 3' end liberated after HinP1I cleavage), and allow probes to hybridize to target. The above probe may be rewritten as (5' region containing the HinP1I sequence, followed by downstream target-specific sequence—UniTaq BI'-Univ.Primer U2'—and 6-10 bases sequence complementary to the free 3' end of the uncleaved upstream primer sequence portion, and optionally 6-10 bases target specific sequence complementary to the 3' end liberated after HinP1I cleavage, followed by an optional spacer, coupled to Univ.Primer U1-UniTaq Ai, followed by upstream target-specific sequence, the HinP1I sequence, followed by one or more bases that mismatch to the target at the 3' end.) Add HinP1I, dNTPs, thermostable polymerase that preferably lacks 5'-3' exonuclease or strand displacement activity, and thermostable ligase (preferably from strain AK16D). After cleavage with HinP1I at 37° C., raise temperature to denature endonuclease while allowing polymerase to extend and ligase to covalently seal the two free ends. In this variation, the coupled probe can contain additional bases or just spacer, and optionally contain a region that polymerase does not copy through.

Step 3: Add Universal Primer U1, Universal Primer U2, and optional Taq Polymerase. Incubate at 55° C. to allow unligated coupled probes to self-hairpin to the 6-10 bases that are complementary to 3' end, which extends to create longer hairpins that render these coupled probes refractory to further amplification. Allow PCR amplification to proceed for 8-20 cycles. In one variation, the universal primer tails U1 and U2 on the LDR compound probes are slightly shorter than Universal primers U1 and U2. This allows initial universal amplification at a lower cycling temperature (i.e. 55° C. annealing) followed by higher cycling temperature (i.e. 65° C. annealing) such that the universal primers U1 and U2 bind preferentially to the desired product (compared to composite LDR probes binding to incorrect products). Further the universal primers U1 and U2 contain a short sequence in common (i.e. 6-10 bases) to avoid primer dimer formation. These conditions amplify fragments of the sequence:

Univ.Primer U1-UniTaq Ai-Upstream Target-GCGC-Downstream Target-UniTaq Bi-Univ.Primer U2'

Step 4: Open tube, dilute 10- to 100-fold and distribute aliquots to Taqman wells, each well containing the following primers: Universal Primer U2 and UniTaq specific primers of the format F1-UniTaq Bi-Q-UniTaq Ai (where F1 is a fluorescent dye that is quenched by Quencher Q). Under these conditions, the following product will form:

F1-UniTaq Bi-Q-UniTaq Ai-Upstream Target-GCGC-Downstream Target-UniTaq Bi'-Univ.Primer U2'

This will hairpin, such that the UniTaq Bi sequence pairs with the UniTaq Bi' sequence. When Universal Primer U2 binds to the Univ.Primer U2' sequence, the 5'→3' exonuclease activity of polymerase digests the UniTaq Bi sequence, liberating the F1 fluorescent dye.

In a variation of the above, the matched downstream LDR primer portions, i.e. 5' G base or flap containing same G base followed by target-specific sequence—UniTaq BI'—do not include 6-10 bases of target specific sequence complementary to the free 3' end of the upstream primer sequence portion. This primer may be rewritten as (5' region containing the HinP1I sequence, followed by downstream target-specific sequence—UniTaq BI'-Univ.Primer U2', followed by an optional cleavable base, coupled to Univ.Primer U1-UniTaq Ai, followed by upstream target-specific sequence, the HinP1I sequence, followed by one or more bases that mismatch to the target at the 3' end). In this version, the connecting region contains an internal sequence that does not inhibit exonuclease digestion, but may be cleaved after an exonuclease digestion step, and prior to a polymerase amplification step. An example of such a sequence is use of a uracil base, which may be subsequently cleaved with uracil DNA glycosylase. In this example, after the ligation step, both Exonuclease I and Exonuclease III are added to digest all unligated coupled probes, as well as all input target DNA. After heat-killing the exonucleases, uracil DNA glycosylase is added to linearize the ligated primers for subsequent PCR amplification.

In both of the above variation, the coupled probes may be synthesized without one or both Univ.Primer U1 and/or Univ.Primer U2' sequences, or portions thereof, thus requiring the need for one or two bridge primers (Universal Primer U1-UniTaq Ai and Universal Primer U2-UniTaq Bi) during the universal PCR amplification step.

In both of the above variations, the coupled probes may be synthesized without (i) a spacer that polymerase does not copy through, or without (ii) an internal sequence that does not inhibit exonuclease digestion, but may be cleaved in a subsequent step. These modifications are designed to linearize the initial circular ligation product and/or prevent polymerase containing 5'→3' exonuclease activity from destroying its own extension product when PCR amplifying using either the universal primer U2, or the secondary oligonucleotide primer set that hybridize to the primary coupled oligonucleotide probes (or complements thereof). The problem may also be solved by using, when possible, a polymerase lacking the 5'-3' exonuclease activity during the initial universal primer amplification step, or by using secondary oligonucleotide primers complementary to the circular ligation product that contain modifications on the 5' end to render them refractory to the 5'→3' exonuclease activity of polymerase. Such 5' modifications include use of thiophosphate in the backbone linkage and/or use of 2'-O-methyl nucleotide analogues.

Highly sensitive methylation detection may be performed using Zipcode array, Zipcode Taqman or traditional Taqman detection as described supra. This approach would use upstream LDR probes (5' Zipcode Zi, followed by target-specific sequence with C*G bases at the 3' end), coupled to the matched downstream LDR probes (5' region containing the BstUI sequence, followed by target-specific sequence—Univ.Primer U2'—and 6-10 bases target specific sequence complementary to the free 3' end of the upstream primer sequence). After universal PCR amplification, these conditions amplify fragments of the sequence:
Univ.Primer U1-Zipcode Zi-Upstream Target-GCGC-Downstream Target-Univ.Primer U2'

For detection using universal (zipcode) arrays, the Univ.Primer U2 would contain a reporter label, i.e. a fluorescent group, while the Univ.Primer U1 would contain a 5' phosphate, and amplification would continue for a total of about 30 to 40 cycles. This would allow for use of lambda exonuclease to digest the second strand, rendering the fluorescently labeled product single-stranded and suitable for hybridization on a universal (zipcode) array.

Highly sensitive methylation detection may be performed using split Zipcode sequences as described supra. This approach would use upstream LDR probes (5' Universal Primer U1, a first half zipcode sequence Zi.1 and a short sequence Ti, followed by target-specific sequence with C*G bases at the 3' end), coupled to the matched downstream LDR probe (5' region containing the BstUI sequence, followed by target-specific sequence—the complement of the short sequence Ti', a second half zipcode sequence Zi.2-Univ.Primer U2'—and 6-10 bases target specific sequence complementary to the free 3' end of the upstream primer sequence). After universal PCR amplification, these conditions amplify fragments of the sequence:
Univ.Primer U1-$1^{st}$ ½ Zipcode Zi.1-Short Ti-Upstream Target-GCGC-Downstream Target-Short Ti'-$2^{nd}$ ½ Zipcode Zi.2-Univ.Primer U2'

When the Short Ti transiently hybridizes to Short Ti', the $1^{st}$ ½ Zipcode Zi.1 sequence is brought in proximity to the $2^{nd}$ ½ Zipcode Zi.2, and the transient hybridization may be stabilized when hybridizing both Zipcode Zi half sequences to the full-length Zipcode Zi' sequence on a zipcode array.

In addition, the above constructs can include unique sequence (ranging from 0 to 10 bases) internal to the Universal primers (Unique Ai, Unique Bi), represented as follows.
Univ.Primer U1-Unique Ai-$1^{st}$ ½ Zipcode Zi.1-Short Ti-Upstream Target-GCGC-Downstream Target-Short Ti'-$2^{nd}$ ½ Zipcode Zi.2-Unique Bi-Univ.Primer U2'

For detection using Zipcode Taqman assays, after the 8-20 cycles of universal amplification, the sample would be diluted 10- to 100-fold and unique primers would be added that overlap with the Unique Ai the Unique Bi sequence for each product. The Taqman probe would be to the full-length zipcode sequence.

Since each junction sequence between the target sequences is unique, the products of the initial universal amplification may also be identified and quantified using next-generation sequencing.

Overview of Fourth Approach: Methylation Sensitive Restriction Enzyme Digestion-Extension.

This approach depends on the activity of two enzymes: (i) the restriction activity of HinP1I, and (ii) the extension activity of polymerase. Isolated genomic DNA, or methyl enriched DNA is treated with the methyl sensitive enzyme HinP1I. Hybridization of two probes to a target containing adjacent methylated HinP1I sequence (i.e. 5' GC*GC 3') allows for cleavage of the 3' hairpin of both the first and second probes by HinP1I. The liberated 3'OH of the upstream probe is extended by polymerase, optionally with either 5'-3' nuclease or strand displacing activity. Uncleaved probes form hairpins and are extended by polymerase to occlude binding of, and subsequent extension or amplification by, the secondary primers.

By insisting on having the restriction endonuclease generate the first probe 3'H, this avoids false signal. Thus, any rare fragment of genomic DNA that was single-stranded after purification, or did not get cleaved will not form a productive substrate for subsequent PCR amplifications, as the product has non-genomic sequences on both sides.

To summarize the levels of discrimination of the above approach for detection of low-abundance methylation (see FIGS. 18A-18G):
1. Use of methylation sensitive HinP1I restriction enzymes to cleave double-stranded target when not methylated.
2. Use of methylation sensitive HinP1I restriction enzymes to nick double-stranded target on both upstream and downstream probe when original genomic DNA was methylated.
3. Use of 3' extension activity of polymerase.
4. Reuse of methylation sensitive HinP1I restriction enzymes to cleave double-stranded target when original genomic DNA was not methylated.
5. Use of sequences on the 3' end of upstream and downstream probes, such that when they are not cleaved, form hairpins at lower temperature and extend on themselves to form products that do not amplify.

An advantage of this approach is that if the target is missing either HinP1I site or alternatively either one is not methylated, the upstream probe will not be nicked, preventing polymerase from extending the liberated 3' OH, and consequently no false amplification can take place.

The current design really only depends on nicking the upstream probe. It will work with only one HinP1I site methylated in the original genomic DNA. It will also work with more than one HinP1I site methylated in the original genomic DNA, however it will not be able to distinguish if there was a mutation in the downstream HinP1I site rendering it refractory to cleavage (but not methylated).

Other variations would limit amplification if downstream sequences contain mutations. For example, when using polymerase that lacks the 5'-3' nuclease activity, designing the upstream probe 3' fragment and both 3' and 5' fragments of the downstream probe such that they easily denature from the target after cleavage by HinP1I will allow the polymerase to extend in a single cycle. It must be rapid enough to avoid being inhibited by a second downstream probe hybridizing. However, this approach would only change the initial yield of product, since eventually such products would amplify when even full-length downstream probe would denature during the PCR cycling steps.

As a control for the total amount of DNA present (see FIGS. 19A-19G), one can choose a nearby target region that is methylated in normal DNA from the plasma or serum, and/or in an imprinted gene where at least one chromosome is always methylated. The upstream oligonucleotide probe is a mixture of two oligos: (i) An oligonucleotide present at 1 in 100 with the correct UniTaq specific sequence, and (ii) an oligonucleotide present at 99 in 100 with a sequence that does not contain the correct UniTaq specific sequence and optionally has about 6-10 bases complementary to its 3' end. The extension product containing the UniTaq sequences amplifies and will give a signal equivalent to 1 in 100 of the original template. The majority extension product lacks the universal sequence on the 5' end, and does not amplify exponentially. Uncleaved probes have 3' hairpin that extends its own 3' sequence on itself, taking it out of contention for becoming part of another PCR amplicon.

As a control for the total amount of DNA present, this approach may also be used with coupled probes, again on a target region as described above. One uses a mixture of two oligonucleotides: (i) An oligonucleotide present at 1 in 100 with the correct UniTaq and/or other tag sequence, and (ii) an oligonucleotide present at 99 in 100 with a sequence that either lacks or has incorrect tag sequences. The extension product containing the UniTaq and/or tag sequences amplifies and will give a signal equivalent to 1 in 100 of the original template. The majority of ligation product either lacks or has incorrect tag sequences, and does not amplify exponentially.

Detailed Protocol for Highly Sensitive Detection of Methylation Marker (when Present at 1% to 0.01%):

Optional Step 1: Cleave isolated genomic DNA, or methyl enriched DNA with the methyl sensitive enzyme HinP1I. Preferably, two or three sites per promoter are chosen for determining methylation status. This step also would destroy any carryover contamination PCR amplicon (which would not be methylated)

Step 2: Denature genomic DNA from plasma (94° C. 1 minute) in the presence of upstream probe (5' Universal Primer U1, followed by UniTaq Ai, followed by target-specific sequence, the HinP1I sequence and a small hairpin at the 3' end), downstream probes (target-specific sequence, the HinP1I sequence and a small hairpin at the 3' end) and allow probes to hybridize to target.

Step 3: Add downstream PCR primer (5' Universal Primer U2, followed by UniTaq Bi, followed by target-specific sequence), Universal Primer U1, and Universal Primer U2, HinP1I, hot-start dNTPs, thermostable polymerase that optionally has 5'-3' exonuclease or strand displacement activity. After cleavage with HinP1I at 37° C., raise temperature to 55° C. to denature endonuclease, activate dNTPs while allowing polymerase to extend.

Continue to incubate at 55° C. to allow both uncleaved upstream and downstream probes to self-hairpin, which extend to create longer hairpins that render these probes refractory to further amplification. Allow PCR amplification to proceed for 8-20 cycles. In one variation, the universal primer tails U1 and U2 on the probes are slightly shorter than Universal primers U1 and U2. This allows initial universal amplification at a lower cycling temperature (i.e. 55° C. annealing) followed by higher cycling temperature (i.e. 65° C. annealing) such that the universal primers U1 and U2 bind preferentially to the desired product. Further the universal primers U1 and U2 contain a short sequence in common (i.e. 6-10 bases) to avoid primer dimer formation. In an optional variation to minimize target independent amplifications, the downstream PCR primers contain a susceptible base and a blocked 3' end, which is liberated by an enzyme that cleaves the susceptible base when the primer is hybridized to its target. For example, the susceptible base may be an RNA nucleotide, with the cleavage enzyme being an RNaseH (See Dobosy et al. *BMC Biotechnology* 11:80 (2011), which is hereby incorporated by reference in its entirety). These conditions amplify products of the sequence:

Univ.Primer U1-UniTaq Ai-Upstream Target-GCGC-Middle Target-GCGC-Downstream Target-UniTaq Bi'-Univ.Primer U2'

Step 4: Open tube, dilute 10- to 100-fold and distribute aliquots to Taqman wells, each well containing the following primers: Universal Primer U2 and UniTaq specific primers of the format F1-UniTaq Bi-Q-UniTaq Ai (where F1 is a fluorescent dye that is quenched by Quencher Q). Under these conditions, the following product will form:

F1-UniTaq Bi-Q-UniTaq Ai-Upstream Target-GCGC-Middle Target-GCGC-Downstream Target-UniTaq Bi'-Univ.Primer U2'

This will hairpin, such that the UniTaq Bi sequence pairs with the UniTaq Bi' sequence. When Universal Primer U2 binds to the Univ.Primer U2' sequence, the 5'→3' exonuclease activity of polymerase digests the UniTaq Bi sequence, liberating the F1 fluorescent dye.

Highly sensitive methylation detection may be performed using Zipcode array, Zipcode Taqman or traditional Taqman detection as described supra. This approach would use upstream PCR primers (5' Universal Primer U1, followed by Zipcode Zi, followed by target-specific sequence, followed by the HinP1I sequence and a small hairpin at the 3' end), and downstream PCR primers (5' Univ.Primer U2, followed by target-specific sequence). After universal PCR amplification, these conditions amplify fragments of the sequence:

Univ.Primer U1-Zipcode Zi-Upstream Target-GCGC-Middle Target-GCGC-Downstream Target-Univ.Primer U2'

For detection using universal (zipcode) arrays, the Univ.Primer U2 would contain a reporter label, i.e. a fluorescent group, while the Univ.Primer U1 would contain a 5' phosphate, and amplification would continue for a total of about 30 to 40 cycles. This would allow for use of lambda exonuclease to digest the second strand, rendering the fluorescently labeled product single-stranded and suitable for hybridization on a universal (zipcode) array.

Highly sensitive methylation detection may be performed using split Zipcode sequences as described supra.

This approach would use upstream PCR primers (5' Universal Primer U1, a first half zipcode sequence Zi.1 and a short sequence Ti, followed by target-specific sequence, followed by the HinP1I sequence and a small hairpin at the 3' end), and downstream PCR primers (5' Univ.Primer U2, (the complement of) a second half zipcode sequence Zi.2, the short sequence Ti', followed by target-specific downstream sequence). After universal PCR amplification, these conditions amplify fragments of the sequence:

Univ.Primer U1-$1^{st}$ ½ Zipcode Zi.1-Short Ti-Upstream Target-GCGC-Middle Target-GCGC-Downstream Target-Short Ti'-$2^{nd}$ ½ Zipcode Zi.2-Univ.Primer U2'

When the Short Ti transiently hybridizes to Short Ti', the $1^{st}$ ½ Zipcode Zi.1 sequence is brought in proximity to the $2^{nd}$ ½ Zipcode Zi.2, and the transient hybridization may be stabilized when hybridizing both Zipcode Zi half sequences to the full-length Zipcode Zi' sequence on a zipcode array.

In addition, the above constructs can include unique sequence (ranging from 0 to 10 bases) internal to the Universal primers (Unique Ai, Unique Bi), represented as follows.

Univ.Primer U1-Unique Ai-$1^{st}$ ½ Zipcode Zi.1-Short Ti-Upstream Target-GCGC-Middle Target-GCGC-Downstream Target-Short Ti'-$2^{nd}$ ½ Zipcode Zi.2-Unique Bi-Univ.Primer U2'

For detection using Zipcode Taqman assays, after the 8-20 cycles of universal amplification, the sample would be diluted 10- to 100-fold and unique primers would be added that overlap with the Unique Ai the Unique Bi sequence for each product. The Taqman probe would be to the full-length zipcode sequence.

Since each junction sequence between the target sequences is unique, the products of the initial universal amplification may also be identified and quantified using next-generation sequencing.

The above protocol may also be used to detect hemi-methylated BstUI sites as illustrated in FIGS. 20A-20G.

Under these conditions, the BstUI enzyme would not be heat inactivated by incubating at 65° C. or even 80° C., and consequently the conditions that heat inactivate BstUI (95° C.) would also denature the cleaved primers prior to extension.

To circumvent this potential difficulty, dNTP's may be used which when incorporated into the DNA generated through polymerase extension, make the initial BstUI site refractory to cleavage. These include incorporation of 5-methyl-dCTP, or using dCTP containing a thiophosphate in the alpha position. Either of these modified nucleotides inhibits BstUI cleavage of the extended product, or the extended hairpinned primers.

In the optional variation to minimize target independent amplifications, the downstream target-specific sequence containing PCR primers contain the susceptible unmethylated BstUI sequence and a blocked 3' end, which is liberated by BstUI when the primer is hybridized to the extended thiophosphate containing target (allowing for nicking of the primer strand, but not the extended copy of the target strand).

For each promoter region, there will be one, two, or three positions of interrogation, such that when the signal appears (Ct value indicating relative quantity of methylated or unmethylated sequence) as well as total signal strength (i.e. =1, 2, or 3 sites methylated or unmethylated for that promoter). To expand on this concept a bit further, the UniTaq reaction provides two types of signal, the Ct value and the end point, or total signal strength. During the universal amplification step, the Universal Primer U2 is used in all the amplicons, and should be in excess, while each UniTaq specific primer F1-UniTaq Bi-Q-UniTaq Ai can be used to provide a specific signal strength. For example, consider that the scale is 1,000 FU (fluorescent units). By titrating both fluorescently labeled (F1-UniTaq Bi-Q-UniTaq Ai) and unlabeled primers (UniTaq Bi-Q-UniTaq Ai) of the same sequence, the end signal strength can be calibrated to a particular level, for example, 100 FU. Consider the following 3 Gene Promoter Methylation, DNA quantification control, and unmethylated DNA controls, with an instrument that can detect 5 fluorescent signals, F1, F2, F3, F4, and F5 respectively. The potential products would be:

Gene 1 Promoter Methylation
F1-UniTaq B1-Q-UniTaq A1-Target DNA-UniTaq B1'-Univ.Primer U2'
F1-UniTaq B2-Q-UniTaq A2-Target DNA-UniTaq B2'-Univ.Primer U2'
F1-UniTaq B3-Q-UniTaq A3-Target DNA-UniTaq B3'-Univ.Primer U2'

Gene 2 Promoter Methylation
F2-UniTaq B4-Q-UniTaq A4-Target DNA-UniTaq B4'-Univ.Primer U2'
F2-UniTaq B5-Q-UniTaq A5-Target DNA-UniTaq B5'-Univ.Primer U2'
F2-UniTaq B6-Q-UniTaq A6-Target DNA-UniTaq B6'-Univ.Primer U2'

Gene 3 Promoter Methylation
F3-UniTaq B7-Q-UniTaq A7-Target DNA-UniTaq B7'-Univ.Primer U2'
F3-UniTaq B8-Q-UniTaq A8-Target DNA-UniTaq B8'-Univ.Primer U2'
F3-UniTaq B9-Q-UniTaq A9-Target DNA-UniTaq B9'-Univ.Primer U2'

DNA Quantification Control (1:100)
F4-UniTaq B10-Q-UniTaq A10-Target DNA-UniTaq B10'-Univ.Primer U2'

Unmethylated DNA Control
F5-UniTaq B11-Q-UniTaq A11-Target DNA-UniTaq B11'-Univ.Primer U2'

(Products without fluorescent labels are not shown for clarity. For each fluorescent product, in the next round of amplification, the Fluorescent group is cleaved off to create signal.)

In this example, a promoter is considered methylated if ⅔ or 3/3 signals are positive. Consider the following results after 45 cycles:
F1, Ct=31.5, final FU=220
F2, Ct=38.5, final FU=90
F3, Ct>45
F4, Ct=28.5, final FU=110
F5, Ct>45

The above result suggests that Gene 1 Promoter (F1 signal) is fully methylated in ⅔ of the fragments interrogated. With a ΔCt value of 3 compared to the 1:100 control, the methylated DNA is present at 1/800, or about 0.12%. This would be consistent with cfDNA arising from a tumor. The Gene 2 Promoter (F2) on the other hand gave some signal, suggesting that ⅓ fragments was methylated, but with a ΔCt value of 10 compared to the 1:100 control, the methylated DNA is present at 1/102,400, or about 0.0009%. This is probably at the limit of genome equivalents interrogated in the plasma sample, and thus most likely represents stochastic methylation due to aging. The Gene 3 Promoter and the unmethylated controls gave no signal.

Prophetic Example 2—Accurate Quantification of Tumor-Specific mRNA Isolated from Exosomes or Circulating Tumor Cells See first and second approaches above. When isolating DNA from circulating tumor cells, the total amount may be quite low. Therefore, it may be prudent to use more than one LDR probe set for a given promoter methylation region, and have the readout in digital PCR. Proceed with Steps 1-3 as described for the first approach above, then:

Step 4: Open tube, dilute 10- to 100-fold and distribute aliquots to wells for digital PCR, each well containing the following primers: Universal Primer U2 and UniTaq specific primers of the format F1-UniTaq Bi-Q-UniTaq Ai. (where F1 is a fluorescent dye that is quenched by Quencher Q). Each well contains a set of ligation products for a given promoter region, as well as for a control region. Under these conditions, the following product will form, after the digital PCR:

F1-UniTaq Bi-Q-UniTaq Ai-Target Region-UniTaq Bi'-Univ.Primer U2'

This will hairpin such that the UniTaq Bi sequence pairs with the UniTaq Bi' sequence. When Universal Primer U2 binds to the Univ.Primer U2' sequence, the 5'→3' exonuclease activity of polymerase digests the UniTaq Bi sequence, liberating the F1 fluorescent dye. The total droplets with fluorescent signal for the target region are compared with the total droplets with fluorescent signal for the control region to determine relative methylation levels.

Prophetic Example 3—Aneuploidy Through Counting Fetal-Specific Promoter Methylation Copy Number (e.g., Trisomy 21)

Overview: Recent work has shown that fetal DNA as a percentage of maternal DNA in the plasma is at approximately 6%, 20%, and 26% in the $1^{st}$, $2^{nd}$, and $3^{rd}$ trimester respectively. Due to how DNA is degraded, maternal DNA is usually about 160 bases and still associated with the H1 histone, while fetal DNA is about 140 bases and not associated with histone. Depending on the clinical need, and where the knowledge will provide the best care, tests may be developed with sufficient sensitivity to detect fetal DNA in the appropriate trimester.

See the first approach as described in Prophetic Example 1 as well as Prophetic Example 2. Given the requirement to distinguish fetal-specific promoter methylation increasing from approximately 6% of DNA when fetal chromosome 21 is diploid to 9% of DNA when fetal chromosome 21 is triploid (under the assumption that the maternal DNA at those promoters is unmethylated), it would probably be wisest to use digital PCR in the last step Although the invention has been described in detail for the purpose of illustration, it is understood that such details are solely for that purpose and variations can be made therein by those skilled in the art without departing from the spirit and scope of the invention which is defined by the following claims.

What is claimed is:

1. A method for identifying, in a sample, one or more target nucleic acid molecules differing from other nucleic acid molecules in the sample by one or more methylated residues, said method comprising:

providing a sample containing one or more target nucleic acid molecules potentially containing one or more methylated residues within at least one methylation sensitive restriction enzyme recognition sequence;

providing one or more oligonucleotide probe sets, each probe set comprising (a) a first oligonucleotide probe having a target-specific portion, and (b) a second oligonucleotide probe having a target specific portion, wherein the first and second oligonucleotide probes of a probe set are configured to hybridize adjacent to one another on the target nucleic acid molecule with a junction between the first and second oligonucleotide probes, and wherein, in a probe set, the target specific portion of the second oligonucleotide probe has an overlapping identical nucleotide at the junction with the first oligonucleotide probe;

contacting the sample and the one or more oligonucleotide probe sets under conditions effective for first and second oligonucleotide probes of a probe set to hybridize at adjacent positions in a base specific manner to their corresponding target nucleic acid molecule, if present in the sample, wherein upon hybridization the overlapping identical nucleotide of the second oligonucleotide probe forms a flap at the junction comprising the overlapping identical nucleotide;

cleaving the overlapping identical nucleotide of the second oligonucleotide probe with an enzyme having 5' nuclease activity, thereby liberating a 5' phosphate on the second oligonucleotide probe;

ligating first and second oligonucleotide probes of the one or more oligonucleotide probe sets together at the junction to form a ligation product hybridized to its complementary target nucleic acid molecule, wherein said ligation product and its hybridized target nucleic acid molecule comprise at least one methylation sensitive restriction enzyme recognition sequence;

blending at least one methylation sensitive restriction enzyme with the hybridized ligation products to form a methylation sensitive restriction enzyme reaction mixture;

subjecting the methylation sensitive restriction enzyme reaction mixture to conditions suitable for cleavage of the ligation product and its hybridized target nucleic acid molecule if said target nucleic acid molecule does not contain one or more methylated residues within the at least one methylation sensitive restriction enzyme recognition sequence, wherein said cleavage will not occur if said target nucleic acid molecule contains one or more methylated residues within the at least one methylation sensitive restriction enzyme recognition sequence;

detecting and distinguishing uncleaved ligation products in the sample; and identifying the presence of one or more target nucleic acid molecules differing from other nucleic acid molecules in the sample by one or more methylated residues based on said detecting.

2. The method of claim 1 further comprising:

subjecting the one or more target nucleic acid molecules in the sample to at least one methylation sensitive restriction enzyme digestion reaction to remove unmethylated target nucleic acid molecules from the sample prior to said contacting.

3. The method of claim 1, wherein the first oligonucleotide probe of the probe set comprises a removable 3' blocking group that prevents extension and/or ligation, said method further comprising:

removing the 3' blocking group of the first oligonucleotide probe using a suitable cleaving enzyme, wherein said removing liberates a 3' OH on the first oligonucleotide probe suitable for extension and/or ligation.

4. The method of claim 1, wherein said detecting comprises:

sequencing the ligation products in the sample.

5. The method of claim 1, wherein the first oligonucleotide probe of a probe set further comprises a 5' primer-specific portion and the second oligonucleotide probe in the probe set further comprises a 3' primer-specific portion, wherein each ligated product comprises the 5' primer-specific portion, the target-specific portions, and the 3' primer-specific portion.

6. The method of claim 5 further comprising:

providing one or more oligonucleotide primer sets, each set comprising (a) a first oligonucleotide primer comprising the same nucleotide sequence as the 5' primer-specific portion of the ligated product and (b) a second oligonucleotide primer comprising a nucleotide sequence that is complementary to the 3' primer-specific portion of the ligated product;

blending the uncleaved ligated products, the one or more oligonucleotide primer sets, and a DNA polymerase after said subjecting to form a polymerase chain reaction mixture; and subjecting the polymerase chain reaction mixture to one or more polymerase chain reaction cycles comprising a denaturation treatment, a hybridization treatment, and an extension treatment thereby forming primary extension products of the uncleaved ligation products, whereby said detecting involves detection of said primary extension products.

7. The method of claim 6 further comprising:

occluding unligated oligonucleotide probes from the sample comprising ligated products prior to said subjecting to prevent unligated oligonucleotide probe extension or amplification.

8. The method of claim 7, wherein the second oligonucleotide probe further comprises a nucleotide flap that is 5' to the target specific portion, wherein at least a portion of the nucleotide flap is complementary to at least a portion of the 3' primer-specific portion of the second oligonucleotide probe, and wherein, in the absence of cleavage, complementary regions of the nucleotide flap and the 3' primer-specific portion of unligated second oligonucleotide probes hybridize to each other to form hairpinned second oligonucleotide probes.

9. The method of claim 8 further comprising:

extending the 3' primer-specific portion of the hairpinned second oligonucleotide probe during said subjecting to form an extended hairpinned second oligonucleotide probe that cannot hybridize to the second oligonucleotide primer.

10. The method of claim 7, wherein the first oligonucleotide probe further comprises a hairpin that is 3' to the target specific portion.

11. The method of claim 10 further comprising:

extending the 3' primer-specific portion of the hairpinned first oligonucleotide probe during said subjecting to form an extended hairpinned first oligonucleotide probe that cannot hybridize to and extend on the target or other extension products.

12. The method of claim 1, wherein the first and second oligonucleotide probes of the one or more oligonucleotide probe sets further comprise a first and second tag portion, respectively, wherein the first and second tag portions of an oligonucleotide probe set are complementary to each other, and wherein the first and second tag portions for each different oligonucleotide probe set have different nucleotide sequences, said method further comprising:

subjecting the sample, after said ligating, to conditions effective for the first and second tag portions of a particular ligated product to hybridize, thereby forming hairpinned ligated products; and removing unligated oligonucleotide probes from the sample after said subjecting.

13. The method of claim 1, wherein the one or more oligonucleotide probe sets further comprise a third oligonucleotide probe having a target-specific target portion, wherein the second and third oligonucleotide probes of a probe set are configured to hybridize on the target nucleic acid molecule, and wherein, in a probe set, the target specific portion of the third oligonucleotide probe has one or more nucleotide bases that are removed during said cleaving or nicking to allow ligation between the second and third oligonucleotide probes at the junction to form a ligated product comprising the first, second, and third oligonucleotide probes of a probe set.

14. The method of claim 1, wherein the sample is selected from the group consisting of tissue, cells, serum, blood, plasma, amniotic fluid, sputum, urine, bodily fluids, bodily secretions, bodily excretions, cell-free circulating nucleic acids, cell-free circulating fetal nucleic acids in pregnant woman, circulating tumor cells, tumor, tumor biopsy, and exosomes.

15. The method of claim 1, wherein the one or more target nucleic acid molecules are low abundance nucleic acid molecules comprising one or more methylated nucleotide bases.

16. The method of claim 1, wherein the one or more target nucleic acid molecules are quantified.

17. The method of claim 1, further comprising:

diagnosing or prognosing a disease state based on said identifying.

18. The method of claim 1, further comprising:

distinguishing a genotype or disease predisposition based on said identifying.

* * * * *